(12) United States Patent
Davis et al.

(10) Patent No.: US 7,427,605 B2
(45) Date of Patent: Sep. 23, 2008

(54) INHIBITORS OF RIBONUCLEOTIDE REDUCTASE SUBUNIT 2 AND USES THEREOF

(75) Inventors: Mark E. Davis, Pasadena, CA (US); Jeremy D. Heidel, Pasadena, CA (US); John J. Rossi, Altaloma, CA (US)

(73) Assignee: Calando Pharmaceuticals, Inc., Pasadena, CA (US)

( * ) Notice: Subject to any disclaimer, the term of this patent is extended or adjusted under 35 U.S.C. 154(b) by 68 days.

(21) Appl. No.: 11/396,365

(22) Filed: Mar. 31, 2006

(65) Prior Publication Data

US 2006/0263435 A1 Nov. 23, 2006

Related U.S. Application Data

(60) Provisional application No. 60/742,100, filed on Dec. 2, 2005, provisional application No. 60/695,931, filed on Jun. 30, 2005, provisional application No. 60/667,362, filed on Mar. 31, 2005.

(51) Int. Cl.
*A61K 31/70* (2006.01)
*A61K 31/715* (2006.01)
*C07H 21/04* (2006.01)

(52) U.S. Cl. ............................ 514/44; 536/24.5; 514/58
(58) Field of Classification Search ........................ None
See application file for complete search history.

(56) References Cited

U.S. PATENT DOCUMENTS

| 4,945,195 A | 7/1990 | Ipcinski |
| 5,998,383 A * | 12/1999 | Wright et al. .................. 514/44 |
| 6,030,942 A | 2/2000 | Cooperman et al. |
| 7,056,704 B2 * | 6/2006 | Tuschl et al. ................. 435/91.1 |
| 7,098,030 B2 * | 8/2006 | Rozema et al. ................ 514/44 |

FOREIGN PATENT DOCUMENTS

WO WO02/24864 3/2002

OTHER PUBLICATIONS

Cerqueria et al., 2005, Overview of ribonucleotide reductase inhibitors: an appealing target in anti-tumour therapy, Curr. Med. Chem. 12:1283.
Database EMBL, Aug. 12, 2002, XP0024007222, database accession No. BQ670934.
Duxbury et al., 2004, Retrovirally mediated RNA interference targeting the M2 subunit of ribonucleotide reductase: A novel therapeutic strategy in pancreatic cancer, Surgery 136:261-269.
Duxbury et al., 2004, RNA interference targeting the M2 subunit of ribonucleotide reductase enhances pancreatic adenocarcinoma chemosensitivity to gemcitabine, Oncogene 28:1539-1548.
Kim et al., 2002, Database EMBL, XP002407223, Database accession No. BM754277.
Kittler et al., 2004, An endoribonuclease-prepared siRNA screen in human cells identifies genes essential for cell division, Nature 432:1036-1040.
Lin et al., 2004, Stable suppression of the R2 subunit of ribonucleotide reductase by R2-targeted short interference RNA sensitizes p53(-/-) HCT-116 colon cancer cells to DNA-damaging agents and ribonucleotide reductase inhibitors, J. Biol. Chem. 279:27030.
Zhou et al., 2003, The human ribonucleotide reductase subunit hRRM2 complements p53R2 in response to UV-induced DNA repair in cells with mutant p53, Cancer Res. 63:6583-6594.

* cited by examiner

*Primary Examiner*—Richard Schnizer
(74) *Attorney, Agent, or Firm*—Ropes & Gray LLP

(57) ABSTRACT

The present application relates to inhibitors of ribonucleotide reductase subunit 2 (R2), and methods and compositions related to the R2 inhibitors. In certain embodiments, the R2 inhibitors include nucleic acids, such as for example siRNAs.

14 Claims, 45 Drawing Sheets

5' CCCAGGCGCAGCCAATGGGAAGGGTCGGAGGCATGGCACAGCCAATGGGAAGGGCCGGGGCACCAAAGCC
AATGGGAAGGGCCGGGAGCGCGCGGCGCGGGAGATTTAAAGGCTGCTGGAGTGAGGGGTCGCCCGTGCAC
CCTGTCCCAGCCGTCCTGTCCTGGCTGCTCGCTCTGCTTCGCTGCGCCTCCACTATGCTCTCCCTCCGTG
TCCCGCTCGCGCCCATCACGGACCCGCAGCAGCTGCAGCTCTCGCCGCTGAAGGGGCTCAGCTTGGTCGA
CAAGGAGAACACGCCGCCGGCCCTGAGCGGGACCCGCGTCCTGGCCAGCAAGACCGCGAGGAGGATCTTC
CAGGAGCCCACGGAGCCGAAAACTAAAGCAGCTGCCCCCGGCGTGGAGGATGAGCCGCTGCTGAGAGAAA
ACCCCCGCCGCTTTGTCATCTTCCCCATCGAGTACCATGATATCTGGCAGATGTATAAGAAGGCAGAGGC
TTCCTTTTGGACCGCCGAGGAGGTTGACCTCTCCAAGGACATTCAGCACTGGGAATCCTGAAACCCGAG
GAGAGATATTTTATATCCCATGTTCTGGCTTTCTTTGCAGCAAGCGATGGCATAGTAAATGAAAACTTGG
TGGAGCGATTTAGCCAAGAAGTTCAGATTACAGAAGCCCGCTGTTTCTATGGCTTCCAAATTGCCATGGA
AAACATACATTCTGAAATGTATAGTCTTCTTATTGACACTTACATAAAAGATCCCAAAGAAAGGGAATTT
CTCTTCAATGCCATTGAAACGATGCCTTGTGTCAAGAAGAAGGCAGACTGGGCCTTGCGCTGGATTGGGG
ACAAAGAGGCTACCTATGGTGAACGTGTTGTAGCCTTTGCTGCAGTGGAAGGCATTTTCTTTTCCGGTTC
TTTTGCGTCGATATTCTGGCTCAAGAAACGAGGACTGATGCCTGGCCTCACATTTTCTAATGAACTTATT
AGCAGAGATGAGGGTTTACACTGTGATTTTGCTTGCCTGATGTTCAAACACCTGGTACACAAACCATCGG
AGGAGAGAGTAAGAGAAATAATTATCAATGCTGTTCGGATAGAACAGGAGTTCCTCACTGAGGCCTTGCC
TGTGAAGCTCATTGGGATGAATTGCACTCTAATGAAGCAATACATTGAGTTTGTGGCAGACAGACTTATG
CTGGAACTGGGTTTTAGCAAGGTTTTCAGAGTAGAGAACCCATTTGACTTTATGGAGAATATTTCACTGG
AAGGAAAGACTAACTTCTTTGAGAAGAGAGTAGGCGAGTATCAGAGGATGGGAGTGATGTCAAGTCCAAC
AGAGAATTCTTTTACCTTGGATGCTGACTTCTAAATGAACTGAAGATGTGCCCTTACTTGGCTGATTTTT
TTTTTCCATCTCATAAGAAAAATCAGCTGAAGTGTTACCAACTAGCCACACCATGAATTGTCCGTAATGT
TCATTAACAGCATCTTTAAAACTGTGTAGCTACCTCACAACCAGTCCTGTCTGTTTATAGTGCTGGTAGT
ATCACCTTTTGCCAGAAGGCCTGGCTGGCTGTGACTTACCATAGCAGTGACAATGGCAGTCTTGGCTTTA
AAGTGAGGGGTGACCCTTTAGTGAGCTTAGCACAGCGGGATTAAACAGTCCTTTAACCAGCACAGCCAGT
TAAAAGATGCAGCCTCACTGCTTAACGCAGATTTTAATGTTTACTTAAATATAAACCTGGCACTTTACA
AACAAATAAACATTGTTTTGTACTCACGGCGGCGATAATAGCTTGATTTATTTGGTTTCTACACCAAATA
CATTCTCCTGACCACTAATGGGAGCCAATTCACAATTCACTAAGTGACTAAAGTAAGTTAAACTTGTGTA
GACTAAGCATGTAATTTTTAAGTTTTATTTTAATGAATTAAAATATTTGTTAACCAACTTTAAAGTCAGT
CCTGTGTATACCTAGATATTAGTCAGTTGGTGCCAGATAGAAGACAGGTTGTGTTTTATCCTGTGGCTT
GTGTAGTGTCCTGGGATTCTCTGCCCCCTCTGAGTAGAGTGTTGTGGGATAAAGGAATCTCTCAGGGCAA
GGAGCTTCTTAAGTTAAATCACTAGAAATTTAGGGGTGATCTGGGCCTTCATATGTGTGAGAAGCCGTTT
CATTTTATTTCTCACTGTATTTTCCTCAACGTCTGGTTGATGAGAAAAATTCTTGAAGAGTTTTCATAT
GTGGGAGCTAAGGTAGTATTGTAAAATTTCAAGTCATCCTTAAACAAAATGATCCACCTAAGATCTTGCC
CCTGTTAAGTGGTGAAATCAACTAGAGGTGGTTCCTACAAGTTGTTCATTCTAGTTTTGTTTGGTGTAAG
TAGGTTGTGTGAGTTAATTCATTTATATTTACTATGTCTGTTAAATCAGAAATTTTTTATTATCTATGTT
CTTCTAGATTTTACCTGTAGTTCATAAAAAAAAAAAAAAAAAAAAAAAAAA 3'

TTAGAAGTCCCAGTCGGTGTCGGTGGTGGGTTGGTGGGTGCCCATTACGTATGAGCTTCCGGAGCCGGAGAAAAAGT
CGTGGTTGTCGCCTGCACCGGGGTCGAGAGCTGCGGCACGGCCGGGTTCACCTGGCAGGTGTCACGATCGAATGCA
GGCTGGTATGCCAGGTTGGGTAGCGCCTTGTTGGCGTTGTAACGCATGTAGGGCAAAACGTCGTCGGTCCAGCCCAA
CTCGTCGTACAAGTCGTGGGCATAGTCGATCTCGTTCGCGTAGAGCGTGTGCAGCAGCTCGCAGGTGTATTCGCGGT
GGTCGGCCCGCTCGGCGTCGGTCAGGTCGGCCAAACCTCGTTGACATTTGTAGCCGATGTAGTAGCCGTGGACGGCT
TCATCTCGGATGATCAGCCGGATCAGATCGGCGGTGTTGGTGAGCTTACCCCGCGACGACCAGTACATGGGCAGGTA
GAAGCCGGAGTAGAACAGGAAGGACTCCAGCATTACCGACGATGCTTTGCGCTTGAGCGCGTCGTCACCGCGGTAGT
AGTCGACGATGATCTGCGCTTTTCGCTGCAGGTAAGGGTTCTGTTCCGACCAGTCGAAGGCATCGTCGATCTGCTTG
GTCGAGCACAGGGTCGAGAAGATCGAGCTGTAGCTCTTGGCGTGCACTGACTCCATGAACGCCATGTTGGTCAGGAC
CGCCTCTTCGTGGGGGGTGACCGCGTCGTCGATCATGGCCACTGCTCCCACCGTCGCCTGCGCGGTGTCGAGCAGGG
TCAAGCCGGTGAACACCCGGATCGTCGTCTGCTGCTCGGTGGAACTCAACGTTTGCCAAGATGCCAGGTCGTTGGAG
AGCGGAATCTTTTCCGGCAACCAAAAGTTACCGGTCAAACGTTCCCAGACCTGCAAATCTTTAGCATCGAGCAACCG
GTTCCAATTGATTGCGTGCACCCGCTCAACGAGCTTGCCGGTCAT

B

ATGTCCAAGTTGTTGTACGTGCGTGATCATGAGGGCTTTGCCTGCCTAACGGTCGAAACCCACCGCAACCGCTGGTT
CGCGGCTCACATTGTCCTCACCAAGGACTGCGGGTGTCTCAAGCTACTCAATGAGAGGGACTTGGAGTTTTACAAGT
TCCTCTTTACGTTCCTGGCCATGGCCGAGAAGCTTGTGAACTTTAACATTGATGAACTGGTCACCAGCTTCGAGAGC
CACGACATTGATCACTACTACACCGAGCAGAAGGCCATGGAGAACGTCCACGGGGAGACTTATGCTAACATTTTAAA
CATGCTCTTTGATGGGGACAGGGCGGCGATGAACGCCTACGCAGAGGCCATCATGGCCGACGAGGCCCTGCAAGCCA
AGATTTCCTGGCTCCGTGACAAGGTGGCGGCCGCCGTCACCCTGCCGGAGAAGATTCTTGTGTTCCTGCTGATTGAA
GGCATCTTCTTCATTAGCTCCTTCTACAGCATAGCCCTGCTGCGGGTCCGGGCCTAATGCCTGGCATCTGCCTGGC
CAATAACTACATAAGTAGGGATGAGCTGCTCCACACCCGCGCTGCCTCCCTGTTATACAATAGCATGACAGCCAAGG
CTGACCGACCAAGGGCCACCTGGATCCAGGAGCTGTTTCGCACTGCGGTGGAGGTAGAGACTGCCTTCATCGAGGCT
CGTGGAGAGGGGGTTACCTTGGTGGATGTGCGAGCCATAAAGCAGTTTCTGGAGGCCACGGCCGATCGCATCCTGGG
TGACATTGGTCAGGCTCCCTTGTATGGCACACCACCCCCAAGGACTGCCCGCTCACCTACATGACTAGCATCAAGC
AAACTAATTTCTTTGAGCAAGAGAGTTCCGATTACACCATGCTGGTGGTAGATGACCTTTGA

FIGURE 2

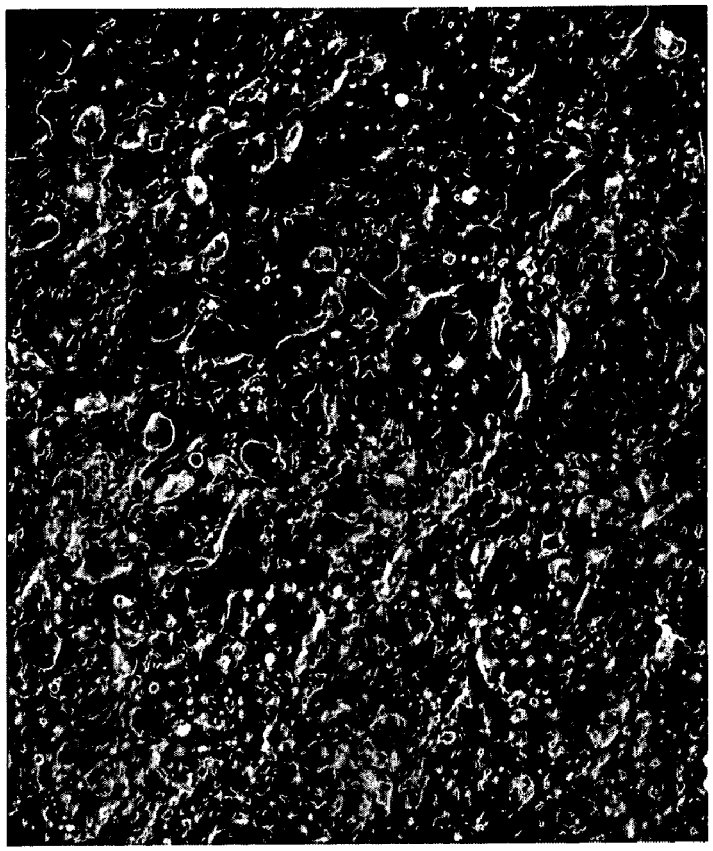
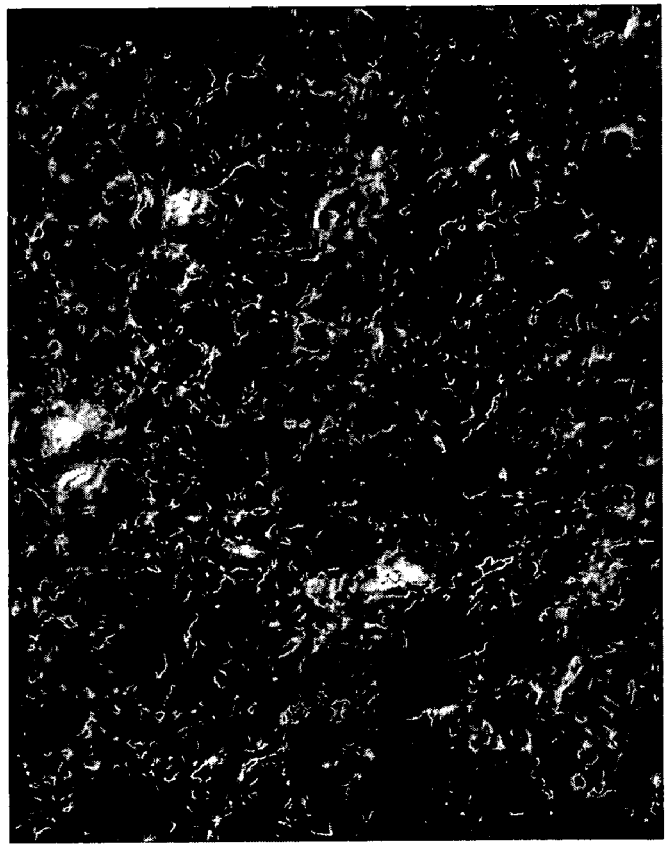
FIGURE 25

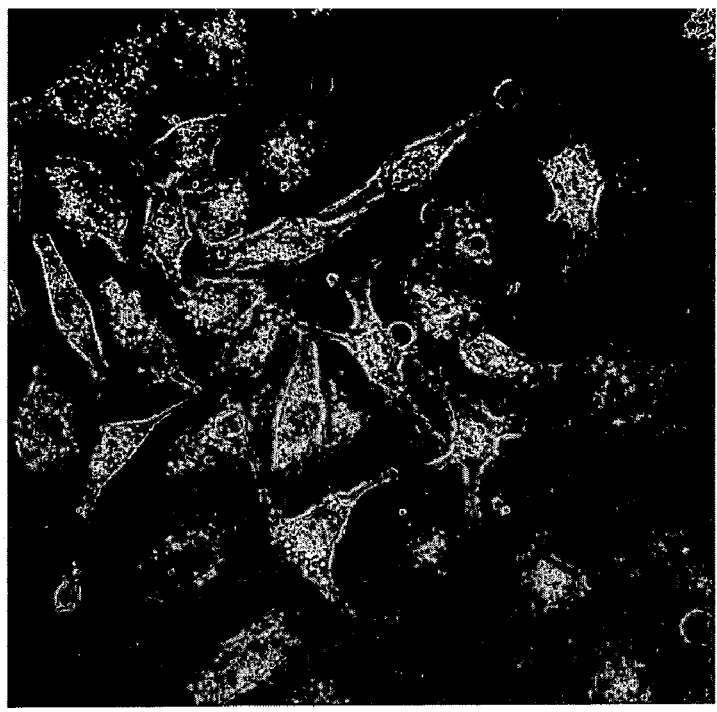
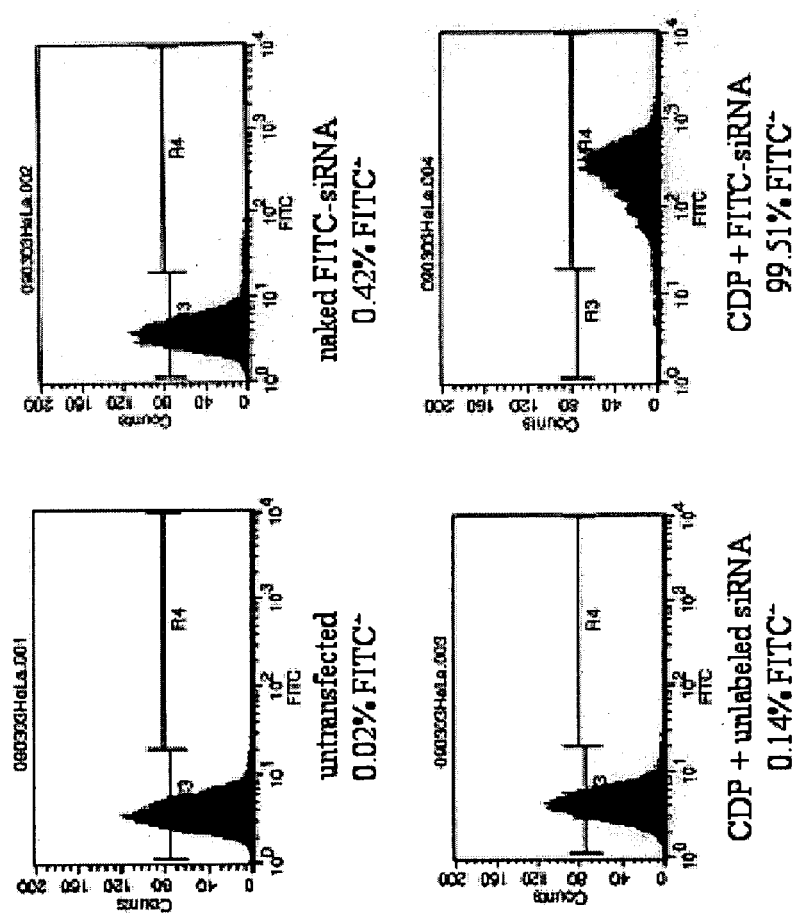
FIGURE 40

US 7,427,605 B2

INHIBITORS OF RIBONUCLEOTIDE REDUCTASE SUBUNIT 2 AND USES THEREOF

RELATED APPLICATIONS

This application claims the benefit of U.S. Provisional Application Nos. 60/667,362, filed Mar. 31, 2005, 60/695,931, filed Jun. 30, 2005, and 60/742,100, filed Dec. 2, 2005, which applications are hereby incorporated by reference in their entireties.

BACKGROUND

Ribonucleotide reductase (RNR) catalyzes the reaction that produces 2'-deoxyribonucleotides from their corresponding ribonucleoside 5'-diphosphates. This reaction is a rate-limiting step in the pathway for the production of 2'-deoxyribonucleoside 5'-triphosphates, and it is necessary for DNA replication. Human RNR consists of two subunits, R1 and R2, and the expression of both proteins is required for enzymatic activity. R1 and R2 are encoded by different genes on separate chromosomes, and most importantly, their mRNAs are differentially expressed throughout the cell cycle. The R1 protein is stable through the entire cell cycle while R2 is only expressed during the late G1/early S phase when DNA replication occurs (Engstrom et al., 1985).

Inhibition of R2 has been an objective for anticancer and antiviral therapeutics. However, novel targeted inhibitors of R2 for treatment of cell proliferative disorders, such as cancer or pathogen infections, would be desirable.

BRIEF DESCRIPTION OF THE APPLICATION

Accordingly, the present application provides R2 inhibitors, and their related methods and compositions that can achieve inhibition of R2 in target cells. In particular, target cells include those cells undergoing unwanted proliferation such as cancer or tumor cells, cells undergoing excessive growth and/or proliferation associated with certain diseases or conditions (e.g., T cells in autoimmune diseases or rejection of transplants), and pathogens. The R2 inhibitors of the application may inhibit R2 by decreasing R2 expression or a biological function of R2 (e.g., an enzymatic activity of R2).

An R2 inhibitor can be a nucleic acid, a small molecule, a peptide including an antibody, a peptide derivative, or a peptidomimetic.

Certain embodiments relate to R2 inhibitors that are nucleic acids. The application provides isolated nucleic acids comprising at least a portion that hybridizes to an R2 transcript under certain conditions (e.g., physiological or intracellular) and decreases the expression of target gene in a cell. The target gene transcript may be any pre-splicing transcript (i.e., including introns), post-splicing transcript, as well as any splice variant. In certain embodiments, the target gene transcript has a sequence set forth in any of SEQ ID NOs:1-3. Examples of categories of nucleic acids include, for example, RNAi constructs and catalytic nucleic acid constructs. A nucleic acid may be single or double stranded. A double stranded nucleic acid may also include regions of overhang or non-complementarity, where one or the other of the strands is single stranded. A single stranded nucleic acid may include regions of self-complementarity, meaning that the compound forms a so-called "hairpin" or "stem-loop" structure, with a region of double helical structure. A nucleic acid may comprise a nucleotide sequence that is complementary to a region consisting of no more than 1000, no more than 500, no more than 250, no more than 100 or no more than 50 nucleotides of the target gene nucleic acid sequence such as any of those designated by SEQ ID NOs: 1-3 (FIGS. 1-2), or any homologs (e.g., orthologs and paralogs) or variants thereof. The region of complementarity will preferably be at least 8 nucleotides, and optionally at least 10, 15, 20, 21, 22, 23, 24, 25, 26, 27, 28, 29, or 30 nucleotides. A region of complementarity may fall within an intron, a coding sequence or a non-coding sequence of the target gene transcript. Generally, a nucleic acid will have a length of about 8 to about 500 nucleotides or base pairs in length, and optionally the length will be about 14 to about 50 nucleotides. A nucleic acid may be a DNA, RNA or RNA:DNA hybrid. Any one strand may include a mixture of DNA and RNA, as well as modified forms that cannot readily be classified as either DNA or RNA. Likewise, a double stranded nucleic acid may be DNA:DNA, DNA:RNA, or RNA:RNA, and any one strand may also include a mixture of DNA and RNA, as well as modified forms that cannot readily be classified as either DNA or RNA. A nucleic acid may include any of a variety of modifications, including one or modifications to the backbone (the sugar-phosphate portion in a natural nucleic acid, including internucleotide linkages) or the base portion (the purine or pyrimidine portion of a natural nucleic acid). A nucleic acid will preferably have a length of about 15 to about 30 nucleotides and will often contain one or more modifications to improve characteristics such as stability in the serum, in a cell or in a place where the nucleic acid is likely to be delivered, such as the stomach in the case of orally delivered nucleic acids and the lung for inhaled nucleic acids. In the case of a RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 30 nucleotides in length and optionally about 21 to 27 nucleotides in length. Catalytic or enzymatic nucleic acids may be ribozymes or DNA enzymes and may also contain modified forms. Nucleic acids herein may inhibit expression of the target R2 gene by about 50%, 75%, 90% or more when contacted with cells under physiological conditions and at a concentration where a nonsense or sense control has little or no effect. Preferred concentrations for testing the effect of nucleic acids are 1, 5, or 10 micromolar. Nucleic acids herein may also be tested for effects on cellular phenotypes. In the case of certain cancer cell lines, cell death or decreased rate of expansion may be measured upon administration of the targeted nucleic acids. Preferably, cell expansion will be inhibited by greater than 50% at an experimentally meaningful concentration of the nucleic acid.

In certain aspects, the application provides pharmaceutical compositions comprising any of the various R2 inhibitors, e.g., nucleic acids targeting an R2 gene (or targeted nucleic acids). A pharmaceutical composition will generally include a pharmaceutically acceptable carrier. A pharmaceutical composition may comprise a nucleic acid that hybridizes to the target gene transcript under physiological conditions and decreases the expression of the target gene in a cell.

In certain aspects, the application provides methods for inhibiting expression of an R2 gene in a cell. The method may comprise contacting the cell with an effective amount of a nucleic acid that hybridizes to the target R2 transcript under physiological conditions and decreases the expression of target gene in a cell. Any of the nucleic acids targeting R2 disclosed may be used in such a method. The cell may be a tumor or cancerous cell, a pathogen cell, or a normal cell. In certain embodiments, the normal cell undergoes unwanted proliferation that leads to a certain disease or condition in a patient.

In certain aspects, the application provides methods for reducing the growth rate of a tumor in a subject, comprising administering an amount of an R2 inhibitor herein sufficient to reduce the growth rate of the tumor. In certain aspects, the application provides methods for treating a patient suffering from a cancer, comprising administering to the patient an R2 inhibitor herein. The R2 inhibitor may be a nucleic acid, for example, an RNAi nucleic acid or a catalytic nucleic acid, and may be formulated with a pharmaceutically acceptable carrier. Optionally, the tumor will comprise one or more cancer cells expressing the gene that the nucleic acid targets. The target R2 gene may be overexpressed relative to a non-cancerous cell from a comparable tissue. The tumor may also be a metastatic tumor. Such treatment may be combined with at least one additional anti-cancer chemotherapeutic agent that inhibits cancer cells in an additive or synergistic manner with the nucleic acid. The nucleic acid and the additional anticancer agent(s) may be formulated in advance as a combination formulation, or may be formulated independently and administered in such a manner (e.g., timing, dosage) so as to achieve the combined effect.

In certain aspects, the application provides for the use of a nucleic acid in the manufacture of a medicament for the treatment of, e.g., cancer or infection by a pathogen.

In certain aspects, the application provides methods for treating a patient suffering from a cancer, comprising: (a) identifying in the patient a tumor having a plurality of cancer cells that express the gene of interest; and (b) administering to the patient, as appropriate, a nucleic acid targeting the gene of interest. A method may include, as a diagnostic part, identifying in the patient a tumor having a plurality of cancer cells having a gene amplification of the target gene. Gene amplifications may be detected in a variety of ways, including, for example, fluorescent in situ hybridization (FISH) or representational oligonucleotide microarray analysis (ROMA).

In certain aspects, the application provides methods and compositions for removing or reducing a pathogen from a patient infected or an object contaminated by the pathogen.

Another aspect of the present application provides a packaged pharmaceutical. Such packaged pharmaceutical comprises: (i) a therapeutically effective amount of an inhibitor disclosed herein that targets an R2 gene; and (ii) instructions and/or a label for administration of the R2 inhibitor for the treatment of patients having tumors that express the R2 gene.

Another aspect of the present application provides a packaged disinfectant. The packaged disinfectant can be specific against one or more infectious agents such as pathogens. Such packaged disinfectant comprises: (i) an effective amount of an R2 inhibitor that targets an R2 gene in the infectious agent; and (ii) instructions and/or label for administration of the R2 inhibitor for removing or reducing the quantity of the infectious agent.

BRIEF DESCRIPTION OF THE DRAWINGS

FIG. 1 shows the cDNA sequence for human ribonucleotide reductase M2 (GenBank Accession No. NM_001034) (SEQ ID NO: 1). The three 11-base stretches underlined and in bold correspond to the core target sequences as represented by SEQ ID NOs: 4-6.

FIG. 2 shows the cDNA sequences for Ribonucleotide Reductase Small Subunit of *Mycobacterium tuberculosis* H37Rv (FIG. 2A) (SEQ ID NO: 2) and for Ribonucleotide Reductase Small Subunit of Human Herpes Virus4 (FIG. 2B) (SEQ ID NO: 3).

FIG. 7A shows a western blot of hRRM2 Protein Levels from HeLa cells treated with a variety of siRNAs as indicated. FIG. 7B shows the results of western blot experiments using lysates from a variety of cell types transfected with siRNAs targeted to the A, B and C sites, a control siRNA and an antisense olgiodeoxynucleotide against hRRM2 (GTI-2040).

FIGS. 9A, 9B and 9C illustrate the results of tiling experiments carried out at target sites A, B and C, respectively. For each target site, eight or more different 21mer sequences adjacent (+ or −) to each of the three originally identified target sites (tiling) were synthesized and compared at three doses each (10 nM, 1 nM and 0.2 nM). FIG. 9D illustrates the experimental design of the tiling experiments.

FIG. 16A shows a summary plot of fusion gene expression over 17 days. FIG. 16B shows representative images taken at 2 days post injection.

FIG. 23(a) shows the size distribution for model bead Gal-50. FIG. 23(b) shows the size distribution for a formulated siRNA particle formed by self-assembly with a linear, cyclodextrin-containing polycation and a galactose-containing, PEG-based modifier.

FIG. 25 shows liver sections from mice subjected to tail-vein injections of particles of different sizes. The left panel shows that Gal-140 beads (having a diameter of 140 nm) are largely absent from the liver section (FIG. 25A). The right panel shows that Gal-50 beads (having a diameter of 50 nm) are present in the liver section (FIG. 25B).

FIG. 31A shows a schematic representation of cyclodextrin-containing polyplex surface modification. FIG. 31B shows a schematic of inclusion complex formation with adamantane (AD)-PEG conjugates (2nd component of system) and β-cyclodextrin. The ligand (L) is for interactions with cell surface receptors. Modified particles can be well-defined and stable to conditions used for in vitro transfections as well as in vivo studies.

FIG. 40 shows that CDP delivers siRNA to cells in culture. FIG. 40A shows FACS analysis of naked and CDP formulated FITC-labeled siRNA in HeLa cells (100 nM siRNA was exposed to HeLa cells for 2 hours). FIG. 40B shows a confocal image of the CDP delivery of FITC-labeled siRNA in HeLa cells (100 nM siRNA was exposed to HeLa cells for 4 hours).

FIG. 42A shows components of the delivery system. FIG. 42B shows assembly of the untargeted and targeted particles.

FIG. 45A shows inhibition of tumor growth with established TC-71 tumors using three daily injections (days 34, 35, 36) of 50 μg siRNA for EWS-FLI1 in Tf-containing particles. FIG. 45B shows PCR data from tumors after two daily injections showing sequence specific inhibition of EWS-FLI1-mRNA.

DETAILED DESCRIPTION OF THE APPLICATION

Overview

Figure 3:
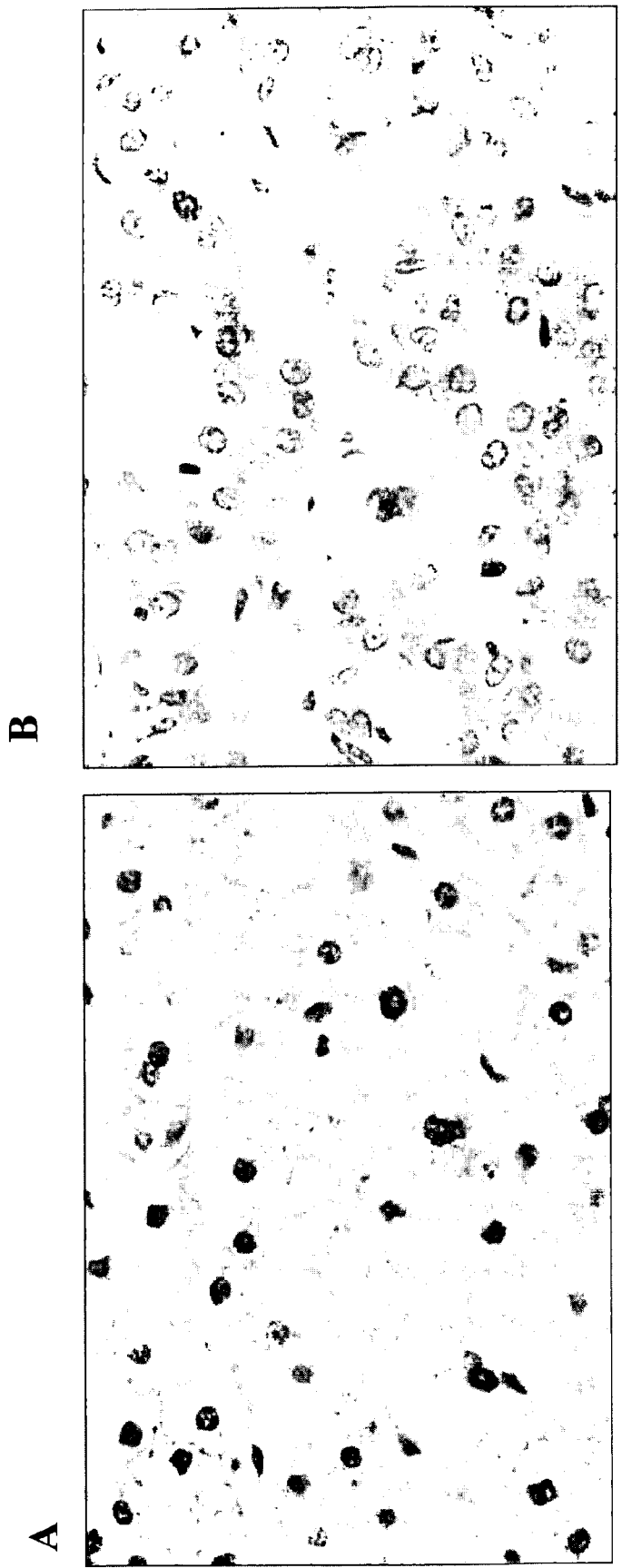
FIG. 3 shows an immunohistochemical staining of R2 in normal human liver tissue (FIG. 3A) and hepatocellular carcinoma (HCC) tissue (FIG. 3B). The images were taken at 400× magnification. R2 expression is detectably upregulated in HCC liver tissue. Freshly excised human HCC tissue were fixed in 4% paraformaldehyde, embedded in paraffin, and 2- to 5-μm sections were cut. After being deparaffinized and rehydrated through graded alcohols, slides underwent microwave antigen retrieval (Antigen Unmasking Solution; Vector Laboratories, Burlingame, Calif.) and were labeled with mouse anti-human anti-RRM2 antibody (1:40 dilution, Covance, Philadelphia, Pa.) and secondary antibody using mouse IgM (with 1:400 diluted, Vector Laboratories). Images were captured using a cooled charge-coupled device camera (Magnafire; Olympus, Melville, NY) and imported into Adobe Phostoshop (Adobe Systems, Mountain View, Calif.) as TIFF files and printed on a Xerox Phaser 860DP printer. Hematoxylin and Eosin (H & E) staining was performed using a standard protocol.

The R2 subunit of the ribonucleotide reductase (RNR) is a desirable therapeutic target because R2 espression is regulated throughout the cell cycle, R2 appears to be an essential gene (Kittler et al. (2004) Nature 432: 1036-1040), and the structure of the R2 protein has been described (Cerqueria et al. (2005) Curr. Med. Chem. 12:1283). In contrast to the R1 subunit of RNR which is in excess at a relatively constant level throughout the cell cycle, R2 synthesis starts in early S phase, and slowly accumulates in the cell up to late mitosis when it is rapidly degraded. Expression of R2 has been detected in various human tissues and tumor cell lines (Zhou et al. (2003) Cancer Research 63:6583-6594). In certain tissues, R2 expression is below detectable level in the normal cells of such tissues but becomes detectable or increased in the abnormal (e.g., tumor or cancerous) cells of such tissues. For example, R2 expression is almost undetectable by western blot or immunostaining in normal liver cells, but can be detected in hepatocyte carcinoma (FIG. 3). Accordingly, inhibition of R2 may be useful for treating diseases or disorders associated with cell proliferation, including, for example, cancer, pathogen infections, etc.

Inhibition of R2 may be achieved by inhibiting a biological activity of R2 in a cell, such as its enzymatic activity. Alternatively, inhibition of R2 may be achieved by inhibiting expression of an R2 gene in a cell. Small molecules and nucleic acids are available to down-regulate R2 activity and/or expression. Examples include dimerization inhibitors that are peptides or peptide derivatives (e.g., U.S. Pat. No. 6,030,942, or the pentapeptide Val Val Asn Asp Leu (SEQ ID NO: 117) as described in U.S. Pat. No. 4,845,195), catalytic inhibitors (e.g., free radical scavengers or iron chelators), antisense molecules (e.g., GTI-2040, Lorus Therapeutics, Inc.), siRNA molecules as described in Lin et al. (2003) J. Biol. Chem. 279:27030 and Duxbury et al. (2004) Oncogene 28:1539. Nevertheless, novel and improved R2 inhibitors remain desirable as new tools to down-regulate R2.

Nucleic Acid R2 Inhibitors

In certain aspects, the application provides nucleic acid inhibitors of an R2 gene and methods for inhibiting or reducing the activity of an R2 gene or protein, for example, by reducing or down-regulating expression of the R2 gene. By "inhibit" or "reduce," it is meant that the expression of the gene, or level of nucleic acids or equivalent nucleic acids encoding one or more proteins or protein subunits is reduced below that observed in the absence of the nucleic acid agents of the application.

As used herein, the term "nucleic acid" or "nucleic acid agent" refers to any nucleic acid-based compound that contains nucleotides and has a desired effect on an R2 gene. The nucleic acids can be single-, double-, or multiple-stranded, and can comprise modified or unmodified nucleotides or non-nucleotides or various mixtures, and combinations thereof. Examples of nucleic acid agents of the application include, but are not limited to, dsRNA, siRNA, and enzymatic nucleic acids.

In certain embodiments, the application provides nucleic acid inhibitors that are targeted to an R2 gene or mRNA from one or more species, including eukaryotes or prokaryotes. In certain embodiments, the nucleic acid inhibitors may be designed such that they specifically inhibit expression of an R2 gene or mRNA sequence from certain species but do not inhibit expression of an R2 gene or mRNA from other species. For example, a nucleic acid inhibitor useful for treatment of a pathogen infection may be designed such that it specifically inhibits R2 gene or mRNA expression in the pathogen but does not inhibit expression of the R2 gene or mRNA of the host. A nucleic acid inhibitor useful for treatment of a bacterial infection may inhibit expression of prokaryotic R2 gene or mRNA expression but does not inhibit eukaryotic R2 gene or mRNA expression. Examples of R2 cDNA sequences from several species are shown in FIGS. 1 and 2.

In certain embodiments, the application provides nucleic acid inhibitors of an R2 gene that are targeted to one or more specific regions within an R2 gene. Exemplary regions within the human R2 gene include the core target regions shown below in Table 1 (see also FIG. 1). A core target sequence generally refers to a portion of the target R2 gene or corresponding mRNA, which effectively inhibit R2 expression upon sequence specific binding by an inhibitor nucleic acid, such as, for example, a dsRNA, an siRNA, or an enzymatic nucleic acid. Generally, a nucleic acid inhibitor can hybridize under stringent conditions to a region of an R2 protein comprising a core target sequence, or a portion of an R2 gene or mRNA comprising 5, 10, or 20 nucleotides flanking one or both ends of the core target regions within the R2 gene or mRNA sequence, e.g., a core target site +/−5, +/−10 or +/−20 nucleotides at either or both ends. The core target sequences shown in Table 1 were obtained from the human R2 sequence, however, the equivalent regions within R2 sequences from other species, including other eukaryotes such as other mammals, are also contemplated herein.

TABLE 1

Core target sequences of R2.

| Description | Sequence | SEQ ID NO |
|---|---|---|
| RRM2-444 Core | 5' cgaguaccaug 3' | SEQ ID NO: 4 |
| RRM2-632 Core | 5' gauuuagccaa 3' | SEQ ID NO: 5 |
| RRM2-928 Core | 5' aagaaacgagg 3' | SEQ ID NO: 6 | dsRNA and RNAi Constructs

In certain embodiments, the application relates to double stranded RNAs (dsRNA) and RNAi constructs. The term "dsRNA" as used herein refers to a double stranded RNA molecule capable of RNA interference (RNAi), including siRNA (see for example, Bass, 2001, Nature, 411, 428-429; Elbashir et al., 2001, Nature, 411, 494-498; and Kreutzer et al., PCT Publication No. WO 00/44895; Zernicka-Goetz et al., PCT Publication No. WO 01/36646; Fire, PCT Publication No. WO 99/32619; Plaetinck et al., PCT Publication No. WO 00/01846; Mello and Fire, PCT Publication No. WO 01/29058; Deschamps-Depaillette, PCT Publication No. WO 99/07409; and Li et al., PCT Publication No. WO 00/44914). In addition, RNAi is a term initially applied to a phenomenon observed in plants and worms where double-stranded RNA (dsRNA) blocks gene expression in a specific and post-transcriptional manner. RNAi provides a useful method of inhibiting or reducing gene expression in vitro or in vivo.

The term "short interfering RNA," "siRNA," or "short interfering nucleic acid," as used herein, refers to any nucleic acid capable of mediating RNAi or gene silencing when processed appropriately by a cell. For example, the siRNA can be a double-stranded polynucleotide molecule comprising self-complementary sense and antisense regions, wherein the antisense region comprises complementarity to a target gene. The siRNA can be a single-stranded hairpin polynucleotide having self-complementary sense and antisense regions, wherein the antisense region comprises complementarity to a target gene. The siRNA can be a circular single-stranded polynucleotide having two or more loop structures and a stem comprising self-complementary sense and antisense regions, wherein the antisense region comprises complementarity to a target gene, and wherein the circular polynucleotide can be processed either in vivo or in vitro to generate an active siRNA capable of mediating RNAi. The siRNA can also comprise a single stranded polynucleotide having complementarity to a target gene, wherein the single stranded polynucleotide can further comprise a terminal phosphate group, such as a 5'-phosphate (see for example Martinez et al., 2002, Cell., 110, 563-574), or 5',3'-diphosphate. In certain embodiments, the siRNAs are non-enzymatic nucleic acids that bind to a target nucleic acid and alter the activity of the target nucleic acid. Binding and/or activity of the siRNA may be facilitated by interaction with one or more protein or protein complexes, such as the RNA Induced Silencing Complex (or RISC). In certain embodiments, the siRNAs comprise a sequence that is complementary to a target sequence along a single contiguous sequence of one strand of the siRNA molecule.

Optionally, the siRNAs of the application contain a nucleotide sequence that hybridizes under physiologic conditions (e.g., in a cellular environment) to the nucleotide sequence of at least a portion of the mRNA transcript for the gene to be inhibited (the "target" gene). The double-stranded RNA need only be sufficiently similar to natural RNA that it has the ability to mediate RNAi. Thus, the application has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, 96%, 97%, 98%, or 99% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing).

The double-stranded structure of dsRNA may be formed by a single self-complementary RNA strand, two complementary RNA strands, or a DNA strand and a complementary RNA strand. Optionally, RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for inhibition.

As described herein, the subject siRNAs comprise a duplex region about 19-30 nucleotides in length, about 21-27 nucleotides in length, about 21-25 nucleotides in length, or about 21-23 nucleotides in length. The siRNAs are understood to recruit nuclease complexes and guide the complexes to the target gene transcript by pairing to the specific sequences. As a result, the target gene transcript is degraded by the nucleases in the protein complex. In certain embodiments, the siRNA molecules comprise a 3' hydroxyl group. In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 27 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell may mediate transcription in vivo, or cloned RNA polymerase can be used for transcription in vitro. As used herein, dsRNA or siRNA molecules of the application need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an dsRNA or siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the application lack 2'-hydroxy (2'-OH) containing nucleotides. In certain embodiments, the siRNA molecules comprise a phosphorothioate sense strand. In certain embodiments, the siRNA molecules comprise a phosphodiester antisense strand.

In a specific embodiment, at least one strand of the siRNA molecules has a 3' overhang from about 1 to about 10 nucleotides in length, about 1 to 5 nucleotides in length, about 1 to 3 nucleotides in length, or about 2 to 4 nucleotides in length. In certain embodiments, an siRNA may comprise one strand having a 3' overhang and the other strand is blunt-ended at the 3' end (e.g., does not have a 3' overhang). In another embodiment, an siRNA may comprise a 3' overhang on both strands. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA or siRNA is in the form of a hairpin structure (or hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52. Preferably, such hairpin RNAs are engineered in cells or in an animal to ensure continuous and stable suppression of a target gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present application provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

In Exemplary embodiments, the application provides siRNAs directed to a core target sequence as shown above in Table 1, or a region corresponding to a region of an R2 gene or mRNA corresponding to a core target sequence with +/−5, +/−10, or +/−20 nucleotides flanking the core target sequence on one or both sides. The sequences of a variety of exemplary siRNA duplexes are provided below in Tables 2-8.

Table 2. siRNA duplexes directed to target sites A, B and C. Underlined residues represent 3' overhangs.

| Description | Sequence | Strand | SEQ ID NO |
|---|---|---|---|
| siRRM2A (or RRM2-444) | 5' cccaucgagua ccaugaua<u>uc</u> 3'<br>3' <u>ag</u>ggguagcuc auggguacuau 5' | Sense<br>Antisense | SEQ ID NO: 7<br>SEQ ID NO: 8 |
| siRRM2B (or RRM2-632) | 5' ggagcgauuua gccaagaa<u>gu</u> 3'<br>3' <u>ca</u>ccucgcuaa aucgguucuu 5' | Sense<br>Antisense | SEQ ID NO: 9<br>SEQ ID NO: 10 |
| siRRM2C (or RRM2-928) | 5' ggcucaagaaa cgaggacu<u>ga</u> 3'<br>3' <u>ga</u>ccgaguucu uugcuccuga 5' | Sense<br>Antisense | SEQ ID NO: 11<br>SEQ ID NO: 12 |

The corresponding 27mer siRNAs of the three 21mers provided in Table 2 above are also R2 expression. See Kim et al., "Synthetic dsRNA Dicer substrates enhance RNAi potency and efficacy." Nature Biotechnology 23:222-226 (2005); Rose et al., "Functional Polarity is Introduced by Dicer Processing of Short Substrate RNAs." Nucleic Acids Resarch, 33(13):4140-56 (2005). The 'R' 27mer has added bases extending to the right side of the initial target sequence (3' with respect to the target), while the 'L' 27mer has added bases extending to the left side of the initial target sequence (5' with respect to the target). Examples of the 27mer siRNAs are shown in Table 3 below.

Table 3. 27mer siRNAs corresponding to the 21mer siRNAs shown in Table 2 above. UPPERCASE letters denote DNA residues, lowercase letters denote RNA residues, [5'phos] denotes a 5' phosphate, and underlined residues denote 3' overhangs.

| Description | Sequence | Strand | SEQ ID NO |
|---|---|---|---|
| siRRM2A1 (or RRM2-444-27R) | 5' [5'phos]cccau cgaguaccaugauauc ugGC 3'<br>3' <u>ag</u>ggguagcucau gguacuauagaccg 5' | Sense<br>Antisense | SEQ ID NO: 13<br>SEQ ID NO: 14 |
| siRRM2A2" (or "RRM2-444-27L) | 5' aucuuccccaucg aguaccaugaua<u>uc</u> 3'<br>3' TAgaagggguagc ucaugguacuau[5'phos] 5' | Sense<br>Antisense | SEQ ID NO: 15<br>SEQ ID NO: 16 |
| siRRM2B1 (or RRM2-632-27R) | 5' [5'phos]ggagc gauuuagccaagaagu ucAG 3'<br>3' <u>ca</u>ccucgcuaaau cgguucuucaaguc 5' | Sense<br>Antisense | SEQ ID NO: 17<br>SEQ ID NO: 18 |
| siRRM2B2 (or RRM2-632-27L) | 5' cuggguggagcga uuuagccaagaa<u>gu</u> 3'<br>3' GAaccaccucgcu aaaucgguucuu[5'phos] 5' | Sense<br>Antisense | SEQ ID NO: 19<br>SEQ ID NO: 20 |
| siRRM2C1 (or RRM2-928-27R) | 5' [5'phos]ggcuc aagaaacgaggacuga gaTG 3'<br>3' <u>ga</u>ccgaguucuuu gcuccugacucuac 5' | Sense<br>Antisense | SEQ ID NO: 21<br>SEQ ID NO: 22 |
| siRRM2C2 (or RRM2-928-27L) | 5' uauucuggcucaa gaaacgaggacu<u>ga</u> 3'<br>3' ATaagaccgaguu cuuugcuccuga[5'phos] 5' | Sense<br>Antisense | SEQ ID NO: 23<br>SEQ ID NO: 24 |

The application also provides siRNAs that target within −20 to +20 bases of a core target sequence or within −10 to +10 bases of an siRNA of the application. For example, 21mer duplexes having target sites within −5 to +5 bases of each of the three 21mer siRNAs are shown or −10 to +10 bases of each of the three core target sequences) are shown in Tables 4-8 below.

Table 4. siRNA duplexes directed against target site A and tiled from −5 to +5 bases of the siRRM2A siRNA duplex. Underlined residues represent 3' overhangs.

| Description | Sequence | Strand | SEQ ID NO |
|---|---|---|---|
| siRRM2A - 5 (or RRM2-439) | 5' ucuucccauc gaguaccaug 3' | Sense | SEQ ID NO: 25 |
| | 3' guagaaggggu agcucauggu 5' | Antisense | SEQ ID NO: 26 |
| siRRM2A - 4 (or RRM2-440) | 5' cuucccaucg aguaccauga 3' | Sense | SEQ ID NO: 27 |
| | 3' uagaagggua gcucauggua 5' | Antisense | SEQ ID NO: 28 |
| siRRM2A - 3 (or RRM2-441) | 5' uucccaucga guaccaugau 3' | Sense | SEQ ID NO: 29 |
| | 3' agaaggggua g cucauggua c | Antisense | SEQ ID NO: 30 |
| siRRM2A - 2 (or RRM2-442) | 5' ucccaucgag uaccaugaua 3' | Sense | SEQ ID NO: 31 |
| | 3' gaaggggua gc ucauggua cu | Antisense | SEQ ID NO: 32 |
| siRRM2A - 1 (or RRM2-443) | 5' ccccaucgagu accaugauau 3' | Sense | SEQ ID NO: 33 |
| | 3' aagggguagcu cauggua cua | Antisense | SEQ ID NO: 34 |
| siRRM2A + 1 (or RRM2-445) | 5' ccaucgaguac caugaaucu 3' | Sense | SEQ ID NO: 35 |
| | 3' gggguagcuca uguacuaua 5' | Antisense | SEQ ID NO: 36 |
| siRRM2A + 2 (or RRM2-446) | 5' caucgaguacc augauaucug 3' | Sense | SEQ ID NO: 37 |
| | 3' ggguagcucau gguacuauag 5' | Antisense | SEQ ID NO: 38 |
| siRRM2A + 3 (or RRM2-447) | 5' aucgaguacca ugauaucugg 3' | Sense | SEQ ID NO: 39 |
| | 3' gguagcucaug guacuauaga 5' | Antisense | SEQ ID NO: 40 |
| siRRM2A + 4 (or RRM2-448) | 5' ucgaguaccau gauaucuggc 3' | Sense | SEQ ID NO: 41 |
| | 3' guagcucaugg uacuauagac 5' | Antisense | SEQ ID NO: 42 |
| siRRM2A + 5 (or RRM2-449) | 5' cgaguaccaug auaucuggca 3' | Sense | SEQ ID NO: 43 |
| | 3' uagcucauggu acuauagacc 5' | Antisense | SEQ ID NO: 44 |

Table 5. siRNA duplexes directed against target site B and tiled from −5 to +5 bases of the siRRM2B siRNA duplex. Underlined residues represent 3' overhangs.

| Description | Sequence | Strand | SEQ ID NO |
|---|---|---|---|
| siRRM2B - 5 (or RRM2-627) | 5' uugguggagcg auuuagccaa 3' | Sense | SEQ ID NO: 45 |
| | 3' ugaaccaccuc gcuaaaucgg 5' | Antisense | SEQ ID NO: 46 |
| siRRM2B - 4 (or RRM2-628) | 5' ugguggagcga uuuagccaag 3' | Sense | SEQ ID NO: 47 |
| | 3' gaaccaccucg cuaaaucggu 5' | Antisense | SEQ ID NO: 48 |
| siRRM2B - 3 (or RRM2-629) | 5' gguggagcgau uuagccaaga 3' | Sense | SEQ ID NO: 49 |
| | 3' aaccaccucgc uaaaucgguu 5' | Antisense | SEQ ID NO: 50 |
| siRRM2B - 2 (or RRM2-630) | 5' guggagcgauu uagccaagaa 3' | Sense | SEQ ID NO: 51 |
| | 3' accaccucgcu aaaucgguuc 5' | Antisense | SEQ ID NO: 52 |
| siRRM2B - 1 (or RRM2-631) | 5' uggagcgauuu agccaagaag 3' | Sense | SEQ ID NO: 53 |
| | 3' ccaccucgcua aaucgguucu 5' | Antisense | SEQ ID NO: 54 |
| siRRM2B + 1 (or RRM2-633) | 5' gagcgauuuag ccaagaaguu 3' | Sense | SEQ ID NO: 55 |
| | 3' accucgcuaaa ucgguucuuc 5' | Antisense | SEQ ID NO: 56 |
| siRRM2B + 2 (or RRM2-634) | 5' agcgauuuagc caagaaguuc 3' | Sense | SEQ ID NO: 57 |
| | 3' ccucgcuaaau cgguucuuca 5' | Antisense | SEQ ID NO: 58 |
| siRRM2B + 3 (or RRM2-635) | 5' gcgauuuagcc aagaaguuca 3' | Sense | SEQ ID NO: 59 |
| | 3' cucgcuaaauc gguucuucaa 5' | Antisense | SEQ ID NO: 60 |
| siRRM2B + 4 (or RRM2-636) | 5' cgauuuagcca agaaguucag 3' | Sense | SEQ ID NO: 61 |
| | 3' ucgcuaaaucg guucuucaag 5' | Antisense | SEQ ID NO: 62 |
| siRRM2B + 5 (or RRM2-637) (or siR2B + 5) (or siRRM2B + 521 mer) | 5' gauuuagccaa gaaguucaga 3' | Sense | SEQ ID NO: 63 |
| | 3' cgcuaaaucgg uucuucaagu 5' | Antisense | SEQ ID NO: 64 |

Table 6. siRNA duplexes directed against target site C and tiled from −5 to +5 bases of the siRRM2C siRNA duplex. Underlined residues represent 3' overhangs.

| Description | Sequence | Strand | SEQ ID NO |
|---|---|---|---|
| siRRM2C - 5 (or RRM2-923) | 5' auucuggcuca agaaacgagg 3' | Sense | SEQ ID NO: 65 |
| | 3' uauaagaccga guucuuugcu 5' | Antisense | SEQ ID NO: 66 |
| siRRM2C - 4 (or RRM2-924) | 5' uucuggcucaa gaaacgagga 3' | Sense | SEQ ID NO: 67 |
| | 3' auaagaccgag uucuuugcuc 5' | Antisense | SEQ ID NO: 68 |
| siRRM2C - 3 (or RRM2-925) | 5' ucuggcucaag aaacgaggac 3' | Sense | SEQ ID NO: 69 |
| | 3' uaagaccgagu ucuuugcucc 5' | Antisense | SEQ ID NO: 70 |
| siRRM2C - 2 (or RRM2-926) | 5' cuggcucaaga aacgaggacu 3' | Sense | SEQ ID NO: 71 |
| | 3' aagaccgaguu cuuugcuccu 5' | Antisense | SEQ ID NO: 72 |
| siRRM2C - 1 (or RRM2-927) | 5' uggcucaagaa acgaggacug 3' | Sense | SEQ ID NO: 73 |
| | 3' agaccgaguuc uuugcuccug 5' | Antisense | SEQ ID NO: 74 |
| siRRM2C + 1 (or RRM2-929) | 5' gcucaagaaac gaggacugau 3' | Sense | SEQ ID NO: 75 |
| | 3' accgaguucuu ugcuccugac 5' | Antisense | SEQ ID NO: 76 |
| siRRM2C + 2 (or RRM2-930) | 5' cucaagaaacg aggacugauc 3' | Sense | SEQ ID NO: 77 |

-continued

| Description | Sequence | Strand | SEQ ID NO |
|---|---|---|---|
| | 3' ccgaguucuuu gcuccugacu 5' | Antisense | SEQ ID NO: 78 |
| siRRM2C + 3 (or RRM2-931) | 5' ucaagaaacga ggacugaugc 3' | Sense | SEQ ID NO: 79 |
| | 3' cgaguucuuug cuccugacua 5' | Antisense | SEQ ID NO: 80 |
| siRRM2C + 4 (or RRM2-932) | 5' caagaaacgag gacugaugcc 3' | Sense | SEQ ID NO: 81 |
| | 3' gaguucuuugc uccugacuac 5' | Antisense | SEQ ID NO: 82 |
| siRRM2C + 5 (or RRM2-933) | 5' aagaaacgagg acugaugccu 3' | Sense | SEQ ID NO: 83 |
| | 3' aguucuuugcu ccugacuacg 5' | Antisense | SEQ ID NO: 84 |

The corresponding 27mer ("27R" or "27L") variants of these 21mer duplexes are also provided. An example is provided below in Table 7.

TABLE 7

A 27mer (or 25/27 mer) siRNA corresponding to the siRRM2B + 5 siRNA duplex. Underlined residues represent a 3' overhang.

| Description | Sequence | Strand | SEQ ID NO |
|---|---|---|---|
| siRRM2B + 5 27mer (or siR2B + 5-27) | 5' [5'phos]gauu uagccaagaaguuc agauuAC 3' | Sense | SEQ ID NO: 85 |
| | 3' cgcuaaaucgg uucuucaagucuaa ug 5' | Antisense | SEQ ID NO: 86 |

Table 8 provides examples of siRNAs that target within −20 to +20 bases of a core target sequence or within −10 to +10 bases of an siRNA of the application.

TABLE 8 siRNA duplexes directed against target site B and tiled from +6 to +10 bases of the siRRM2B siRNA duplex. Underlined residues represent 3' overhangs.

| Description | Sequence | Strand | SEQ ID NO |
|---|---|---|---|
| siRRM2B + 6 (or RRM2-638) (or siR2B + 6) | 5' auuuagccaag aaguucagau 3' | Sense | SEQ ID NO: 87 |
| | 3' gcuaaaucggu ucuucaaguc 5' | Antisense | SEQ ID NO: 88 |
| siRRM2B + 7 (or RRM2-639) (or siR2B + 7) | 5' uuuagccaaga aguucagauu 3' | Sense | SEQ ID NO: 89 |
| | 3' cuaaaucgguu cuucaagucu 5' | Antisense | SEQ ID NO: 90 |
| siRRM2B + 8 (or RRM2-640) (or siR2B + 8) | 5' uuagccaagaa guucagauua 3' | Sense | SEQ ID NO: 91 |
| | 3' uaaaucgguuc uucaagucua 5' | Antisense | SEQ ID NO: 92 |
| siRRM2B + 9 (or RRM2-641) (or siR2B + 9) | 5' uagccaagaag uucagauuac 3' | Sense | SEQ ID NO: 93 |
| | 3' aaaucgguucu ucaagucuaa 5' | Antisense | SEQ ID NO: 94 |

TABLE 8-continued siRNA duplexes directed against target site B and tiled from +6 to +10 bases of the siRRM2B siRNA duplex. Underlined residues represent 3' overhangs.

| Description | Sequence | Strand | SEQ ID NO |
|---|---|---|---|
| siRRM2B + 10 (or RRM2-642) (or siR2B + 10) | 5' agccaagaagu ucagauuaca 3' | Sense | SEQ ID NO: 95 |
| | 3' aaucgguucuu caagucuaau 5' | Antisense | SEQ ID NO: 96 |

Enzymatic Nucleic Acids

In certain embodiments, the application relates to enzymatic nucleic acids that inhibit R2 gene or mRNA expression. Exemplary enzymatic nucleic acids include those that are targeted to one of the core target sequences provided in Table 1 above, or a region comprising a core target sequence with 5, 10, or 20 nucleotides flanking one or both sides of the core target sequences. By "enzymatic nucleic acid," it is meant a nucleic acid which has complementarity in a substrate binding region to a specified target gene, and also has an enzymatic activity which is active to specifically cleave a target nucleic acid. It is understood that the enzymatic nucleic acid is able to intermolecularly cleave a nucleic acid and thereby inactivate a target nucleic acid. These complementary regions allow sufficient hybridization of the enzymatic nucleic acid to the target nucleic acid and thus permit cleavage. One hundred percent complementarity (identity) is preferred, but complementarity as low as 50-75% can also be useful in this application (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acidss with enzymatic activity. The specific enzymatic nucleic acids described in the instant application are not limiting in the application and those skilled in the art will recognize that all that is important in an enzymatic nucleic acid of this application is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

Several varieties of naturally-occurring enzymatic nucleic acids are currently known. Each can catalyze the hydrolysis of nucleic acid phosphodiester bonds in trans (and thus can cleave other nucleic acids) under physiological conditions. In general, enzymatic nucleic acids act by first binding to a target nucleic acid. Such binding occurs through the target binding portion of a enzymatic nucleic acid which is held in close proximity to an enzymatic portion of the molecule that acts to cleave the target nucleic acid. Thus, the enzymatic nucleic acid first recognizes and then binds a target nucleic acid through complementary base-pairing, and once bound to the correct site, acts enzymatically to cut the target nucleic acid. Strategic cleavage of such a target nucleic acid will destroy its ability to direct synthesis of an encoded protein. After an enzymatic nucleic acid has bound and cleaved its nucleic acid target, it is released from that nucleic acid to search for another target and can repeatedly bind and cleave new targets.

In a specific embodiment, the subject enzymatic nucleic acid is a ribozyme designed to catalytically cleave an R2 mRNA to prevent translation of the mRNA (see, e.g., PCT International Publication WO90/11364, published Oct. 4, 1990; Sarver et al., 1990, Science 247:1222-1225; and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNAs have the following sequence of two bases: 5'-UG-3'. The construction and production of hammerhead ribozymes is well known in the art and is described more fully in Haseloff and Gerlach, 1988, Nature, 334:585-591. The ribozymes of the present application also include RNA endoribonucleases (hereinafter "Cech-type ribozymes") such as the one which occurs naturally in Tetrahymena thermophila (known as the IVS or L-19 IVS RNA) and which has been extensively described (see, e.g., Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216).

In another specific embodiment, the subject enzymatic nucleic acid is a DNA enzyme. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. Briefly, to design an ideal DNA enzyme that specifically recognizes and cleaves a target nucleic acid, one of skill in the art must first identify the unique target sequence. Preferably, the unique or substantially sequence is a G/C rich of approximately 18 to 22 nucleotides. High G/C content helps insure a stronger interaction between the DNA enzyme and the target gene sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

In certain embodiments, the nucleic acid agents of the application can be between 12 and 200 nucleotides in length. In one embodiment, exemplary enzymatic nucleic acids of the application are between 15 and 50 nucleotides in length, including, for example, between 25 and 40 nucleotides in length (for example see Jarvis et al., 1996, J. Biol. Chem., 271, 29107-29112). In another embodiment, exemplary antisense molecules of the application are between 15 and 75 nucleotides in length, including, for example, between 20 and 35 nucleotides in length (see for example Woolf et al., 1992, PNAS., 89, 7305-7309; Milner et al., 1997, Nature Biotechnology, 15, 537-541). In another embodiment, exemplary siRNAs of the application are between 20 and 30 nucleotides in length, including, for example, between 21 and 27 nucleotides in length. Those skilled in the art will recognize that all that is required is that the subject nucleic acid agent be of length and conformation sufficient and suitable for its activity contemplated herein. The length of the nucleic acid agents of the instant application is not limiting within the general limits stated.

Synthesis of Nucleic Acid Agents

Synthesis of nucleic acids greater than 100 nucleotides in length is difficult using automated methods, and the therapeutic cost of such molecules is prohibitive. In this application, small nucleic acid motifs (small refers to nucleic acid motifs less than about 100 nucleotides in length, preferably less than about 80 nucleotides in length, and more preferably less than about 50 nucleotides in length (e.g., enzymatic nucleic acids and RNAi constructs) are preferably used for exogenous delivery. The simple structure of these molecules increases the ability of the nucleic acid to invade targeted regions of RNA structure.

Exemplary nucleic acid inhibitor molecules, include RNA and DNA molecules, of the instant application can be chemically synthesized. To illustrate, oligonucleotides (e.g., DNA) are synthesized using protocols known in the art as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer with a 2.5 min coupling step for 2'-O-methylated nucleotides and a 45 sec coupling step for 2'-deoxy nucleotides. Alternatively, syntheses can be performed on a 96-well plate synthesizer, such as the instrument produced by Protogene (Palo Alto, Calif.) with minimal modification to the cycle.

Optionally, portions of the instant nucleic acids can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

Preferably, the nucleic acids herein are modified extensively to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163). Ribozymes are purified by gel electrophoresis using general methods or are purified by high pressure liquid chromatography (HPLC; See Wincott et al., supra) and are re-suspended in water.

Optimizing Activity of the Nucleic Acids

Nucleic acids with modifications (e.g., base, sugar and/or phosphate) can prevent their degradation by serum ribonucleases and thereby increase their potency. There are several examples in the art describing sugar, base and phosphate modifications that can be introduced into nucleic acids with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acids have been extensively described in the art (see Eckstein et al., PCT Publication No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. PCT Publication No. WO 93/15187; Sproat, U.S. Pat. No. 5,334,711 and Beigelman et al., 1995, J. Biol. Chem., 270, 25702; Beigelman et al., PCT publication No. WO 97/26270; Beigelman et al., U.S. Pat. No. 5,716,824; Usman et al., U.S. Pat. No. 5,627,053; Woolf et al., PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic acid Sciences), 48, 39-55; Verma and Eckstein, 1998, Annu. Rev. Biochem., 67, 99-134; and Burlina et al., 1997, Bioorg. Med. Chem., 5, 1999-2010). Similar modifications can be used to modify the nucleic acids of the instant application.

While chemical modification of oligonucleotide internucleotide linkages with phosphorothioate, phosphorothioate, and/or 5'-methylphosphonate linkages improves stability, an over-abundance of these modifications can cause toxicity. Therefore, the amount of these internucleotide linkages should be evaluated and appropriately minimized when designing the nucleic acids. The reduction in the concentration of these linkages should lower toxicity resulting in increased efficacy and higher specificity of these molecules.

In one embodiment, nucleic acids of the application include one or more G-clamp nucleotides. A G-clamp nucleotide is a modified cytosine analog wherein the modifications confer the ability to hydrogen bond both Watson-Crick and Hoogsteen faces of a complementary guanine within a duplex, see for example, Lin and Matteucci, 1998, J. Am. Chem. Soc., 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acids of the application results in both enhanced affinity and specificity to nucleic acid targets. In another embodiment, nucleic acids of the application include one or more LNA (locked nucleic acid) nucleotides such as a 2',4'-C mythylene bicyclo nucleotide (see for example Wengel et al., PCT Publication Nos. WO 00/66604 and WO 99/14226).

In another embodiment, the application features conjugates and/or complexes of nucleic acids targeting an R2 gene. Such conjugates and/or complexes can be used to facilitate delivery of nucleic acids into a biological system, such as cells. The conjugates and complexes provided by the instant application can impart therapeutic activity by transporting or transferring therapeutic agents to a target tissue or cell type, across cellular membranes, altering the pharmacokinetics, and/or modulating the localization of nucleic acids of the application. Such conjugates and/or complexes are also described below.

The present application encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acids of the application into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable nucleic acid linker molecule" as used herein, refers to a nucleic acid molecule that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example, 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example, a phosphoramidate or phosphodiester linkage. The biodegradable nucleic acid linker molecule can also comprise nucleic acid backbone, nucleic acid sugar, or nucleic acid base modifications. The term "biodegradable" as used herein, refers to degradation in a biological system, for example enzymatic degradation or chemical degradation.

Therapeutic nucleic acid agents, such as the molecules described herein, delivered exogenously are optimally stable within cells until translation of the target RNA has been inhibited long enough to reduce the levels of the undesirable protein. This period of time varies between hours to days depending upon the disease state. These nucleic acid agents should be resistant to nucleases in order to function as effective intracellular therapeutic agents. Improvements in the chemical synthesis of nucleic acids herein and in the art have expanded the ability to modify nucleic acids by introducing nucleotide modifications to enhance their nuclease stability as described above.

In another aspect the nucleic acids comprise a 5' and/or a 3'-cap structure. By "cap structure," it is meant chemical modifications, which have been incorporated at either terminus of the oligonucleotide (see for example Wincott et al., WO 97/26270). These terminal modifications protect the nucleic acid from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl)nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al, supra). In other non-limiting examples, the 3'-cap includes, for example, 4',5'-methylene nucleotide; 1-(bela-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosy nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925).

Use of the R2 Inhibitors

In certain embodiments, the present application provides methods of inhibiting unwanted proliferation of one or more cells, for example, tumor or cancerous cells, or pathogen cells. In certain embodiments, the application provides methods of inhibiting or reducing tumor growth and methods of treating an individual suffering from a cancer. These methods involve administering to the individual patient an effective amount of one or more R2 inhibitors (e.g., siRNAs) as described above. In certain embodiments, the present application provides methods for treating metastatic cancer and/or preventing metastasis. In certain embodiments, the present application provides methods for treating cancer resistant to traditional therapies, such as, for example chemotherapeutic agents. Certain methods are particularly aimed at therapeutic and prophylactic treatments of animals, and more particularly, humans, and in such methods, a therapeutically effective amount of the R2 inhibitor(s) is administered to the animal or human patient.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As described herein, the tumor or cancer includes a tumor inside an individual, a tumor xenograft, or a tumor cultured in vitro. In particular, nucleic acid agents of the present application are useful for treating or preventing a cancer. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the R2 inhibitors of the present invention include cancers comprising hedgehog expressing cells. Still further exemplary forms of cancer which can be treated with an R2 inhibitor of the present application include cancers comprising R2 expressing cells. In certain such embodiments, the normal or non-cancerous cells of the same tissue type as the cancer cells may not express R2 at a level detectable by techniques in the art; for example, normal liver tissue or hepatocytes do not express detectable levels of R2, in contrast to expression of R2 in hepatocyte carcinoma cells. The application contemplates that the R2 inhibitors herein can be used alone, or can be administered as part of an overall treatment regimen including other therapeutics and/or other traditional or non-traditional therapies.

Further examples of cancers that can be treated using the R2 inhibitor nucleic acids described herein include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In certain embodiments, the application provides methods of inhibiting proliferation of pathogen cells, for example, in a patient suffering from an infection by the pathogen cells, or in or on an object (e.g., laboratory or medical equipment, a kitchen counter, or or any object subjected to pathogen contamination, etc.) contaminated by the pathogen cells. Examples of pathogens include viruses, bacteria, fungi, etc. Extensive genomic information for a wide variety of pathogens are available in public databases. Such genomic information can be used to design nucleic acid inhibitors targeted to an R2 gene in a variety of pathogens.

Examples of disease causing viruses that may be used in accord with the methods described herein include: Retroviridae (e.g., human immunodeficiency viruses, such as HIV-1 (also referred to as HTLV-III, LAV or HTLV-III/LAV, See Ratner, L. et al., Nature, Vol. 313, Pp. 227-284 (1985); Wain Hobson, S. et al, Cell, Vol. 40: Pp. 9-17 (1985)); HIV-2 (See Guyader et al., Nature, Vol. 328, Pp. 662-669 (1987); European Patent Publication No. 0 269 520; Chakraborti et al., Nature, Vol. 328, Pp. 543-547 (1987); and European Patent Application No. 0 655 501); and other isolates, such as HIV-LP (International Publication No. WO 94/00562 entitled "A Novel Human Immunodeficiency Virus"; Picornaviridae (e.g., polio viruses, hepatitis A virus, (Gust, I. D., et al., Intervirology, Vol. 20, Pp. 1-7 (1983); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbivirses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatities (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pylori, Borrelia burgdorferi, Legionella pneumophilia, Mycobacterium* sps. (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

Genomic information (including nucleotide sequences, amino acid sequences, protein expression information, and/or protein structure information) for a variety of microorganisms may be found in the databases maintained by The Institute for Genomic Research (TIGR) and/or the National Center for Biotechnology Information (NCBI).

Examples of archaea for which genomic information is available from TIGR and/or NCBI, include, for example, *Aeropyrum pernix* (NC_000854), *Archaeoglobus fulgidus* (NC_000917), *Halobacterium* sp. NRC-1 (NC_002607), *Methanococcus jannaschii* NC_000909), *Methanopyrus kandleri* AV19 (NC_003551), *Methanosarcina acetivorans* str. C2A (NC_003552), *Methanosarcina mazei* Goel (NC_003901), *Methanothermobacter thermautotrophicus* (NC_000916), *Pyrobaculum aerophilum* (NC_003364), *Pyrococcus abyssi* (NC_000868), *Pyrococcus furiosus* DSM 3638 (NC_003413), *Pyrococcus horikoshii* (NC_000961), *Sulfolobus solfataricus* (NC_002754), *Sulfolobus tokodaii* (NC_003106), *Thermoplasma acidophilum* (NC_002578), and *Thermoplasma volcanium* (NC_002689).

Examples of eukaryotes for which genomic information is available from TIGR and/or NCBI, include, for example, *Anopheles gambiae, Arabidopsis thaliana, Caenorhabditis elegans, Drosophila melanogaster, Encephalitozoon cuniculi, Guillardia theta nucleomorph, Saccharomyces cerevisiae*, and *Schizosaccharomyces pombe*.

Genomic information for over 900 viral species is available from TIGR and/or NCBI, including, for example, information about deltaviruses, retroid viruses, satellites, dsDNA viruses, dsRNA viruses, ssDNA viruses, ssRNA negative-strand viruses, ssRNA positive-strand viruses, unclassified bacteriophages, and other unclassified viruses.

In certain embodiments, the application provides methods of inhibiting unwanted proliferation of a normal cell (e.g., a non-cancerous and/or non-pathogenic cell). For example, a normal cell may be a cell required for hair growth, and unwanted hair growth may be treated with a method described herein; the unwanted proliferation of a cell can occur in normal hair growth, in trichosis, hypertrichosis, hirsutism, or folliculitis including folliculitis decalvans, folliculitis ulerythematosa reticulata, keloid folliculitis, and pseudofolliculitis. In a further example, a normal cell may be an immune cell that is involved in an undesirable immune response, such as, an autoimmune response, transplant rejection, etc. In an exemplary embodiment, a normal cell may be a normal T cell, and excessive activity or proliferation of T cells is responsible for a number of diseases or conditions including: diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, and T-cell neoplasms such as leukemias and/or lymphomas.

In certain embodiments of the methods herein, one or more nucleic acid inhibitors of R2 can be administered, together (simultaneously) or at different times (sequentially). For example, two or more dsRNAs, siRNAs, or enzymatic nucleic acids, or combinations thereof, may be used in accordance with the methods described herein.

In certain embodiments, the subject inhibito nucleic acids of the application can be used alone. Alternatively, the subject inhibitor nucleic acids may be administered in combination with other conventional anti-cancer, anti-pathogen, or other therapeutic approaches directed to treatment or prevention of unwanted cell proliferation. For example, such methods can be used in prophylactic cancer prevention, prevention of cancer recurrence and metastases after surgery, and as an adjuvant of other conventional cancer therapy. The present application recognizes that the effectiveness of conventional cancer therapies (e.g., chemotherapy, radiation therapy, phototherapy, immunotherapy, and surgery) can be enhanced through the use of a subject nucleic acid agent. When using a combination therapy comprising an R2 inhibitor nucleic acid and another therapeutic agent, such therapeutic agents may be administered separately or conjointly. In certain embodiments, combination therapies may involve an R2 inhibitor nucleic acid and another therapeutic agent that are formulated together or administered as separate formulations.

A wide array of conventional compounds have been shown to have anti-neoplastic activities. These compounds have been used as pharmaceuticalal agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Pharmaceutical compounds that may be used for combinatory therapy, in particular, anti-tumor therapy, include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, the R2 inhibitor nucleic acids described herein may be administered in combination with other therapeutic agents, including, for example, anti-inflammatory agents, immunosuppressive agents, and/or anti-infective agents (such as for example, antibiotic, antiviral, and/or antifungal compounds, etc.). Exemplary anti-inflammatory drugs include, for example, steroidal (such as, for example, cortisol, aldosterone, prednisone, methylprednisone, triamcinolone, dexamethasone, deoxycorticosterone, and fluorocortisol) and non-steroidal anti-inflammatory drugs (such as, for example, ibuprofen, naproxen, and piroxicam). Exemplary immunosuppressive drugs include, for example, prednisone, azathioprine (Imuran), cyclosporine (Sandimmune, Neoral), rapamycin, antithymocyte globulin, daclizumab, OKT3 and ALG, mycophenolate mofetil (Cellcept) and tacrolimus (Prograf, FK506). Exemplary antibiotics include, for example, sulfa drugs (e.g., sulfanilamide), folic acid analogs (e.g., trimethoprim), beta-lactams (e.g., penacillin, cephalosporins), aminoglycosides (e.g., stretomycin, kanamycin, neomycin, gentamycin), tetracyclines (e.g., chlorotetracycline, oxytetracycline, and doxycycline), macrolides (e.g., erythromycin, azithromycin, and clarithromycin), lincosamides (e.g., clindamycin), streptogramins (e.g., quinupristin and dalfopristin), fluoroquinolones (e.g., ciprofloxacin, levofloxacin, and moxifloxacin), polypeptides (e.g., polymixins), rifampin, mupirocin, cycloserine, aminocyclitol (e.g., spectinomycin), glycopeptides (e.g., vancomycin), and oxazolidinones (e.g., linezolid). Exemplary antiviral agents include, for example, vidarabine, acyclovir, gancyclovir, valganciclovir, nucleoside-analog reverse transcriptase inhibitors (e.g., ZAT, ddI, ddC, D4T, 3TC), non-nucleoside reverse transcriptase inhibitors (e.g., nevirapine, delavirdine), protease inhibitors (e.g., saquinavir, ritonavir, indinavir, nelfinavir), ribavirin, amantadine, rimantadine, relenza, tamiflu, pleconaril, and interferons. Exemplary antifungal drugs include, for example, polyene antifungals (e.g., amphotericin and nystatin), imidazole antifungals (ketoconazole and miconazole), triazole antifungals (e.g., fluconazole and itraconazole), flucytosine, griseofulvin, and terbinafine.

Depending on the nature of the combinatory therapy, administration of the nucleic acid therapeutic agents of the application may be continued while the other therapy is being administered and/or thereafter. Administration of the nucleic acid therapeutic agents may be made in a single dose, or in multiple doses. In some instances, administration of the nucleic acid therapeutic agents is commenced at least several days prior to the conventional therapy, while in other instances, administration is begun either immediately before or at the time of the administration of the conventional therapy.

Methods of Administration and Compositions

In certain embodiments, the application provides compositions comprising one or more R2 inhibitors described herein. In certain embodiments, the compositions are pharmaceutical, suitable for therapeutic uses in a patient. In certain embodiments, the compositions are cosmetic, suitable for cosmetic uses in an animal or a human. In alternative embodiments, the compositions are non-pharmaceutical and non-cosmetic. Generally, the difference between a cosmetic and a pharmaceutical is that the latter requires regulatory approval (e.g., by the Food and Drug Administration) to be used in a human or animal.

Methods for delivering the R2 inhibitors, in particular, the nucleic acids may be based on those methods known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized, modified, or improved for the delivery of virtually any nucleic acid. Nucleic acids can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example through the use of conjugates and biodegradable polymers. In certain embodiments, the subject R2 inhibitor and the vehicle are combined and formulated in the final dosage form before administration. In alternative embodiments, the subject R2 inhibitor and the vehicle are separately formulated such that they will be combined at the time of administration. For example, the subject R2 inhibitor and the vehicle may be stored in separate compartments of a delivery kit or package, and at the time of administration to a desirable site or through a desirable route, the subject R2 inhibitor and the vehicle are mixed for delivery. The separate compartments can be separate vials in a kit, separate cartridges in a medicine delivery pen (see U.S. Pat. No. 5,542,760), separate cannulas or compartments in a syringe, etc.

In certain embodiments, the subject R2 inhibitors are provided as supramolecular complexes that include polymeric microparticles or nanoparticles as delivery vehicles. As used herein, the terms "microparticles" or "nanoparticles" include microspheres or nanospheres (uniform spheres), microcapsules or nanocapsules (having a core and an outer layer of polymer), and particles of irregular shape.

The application contemplates uses of polymers that are preferably biodegradable within the time period over which release of the R2 inhibitor is desired or relatively soon thereafter, generally in the range of one year, more typically a few months, even more typically a few days to a few weeks. Biodegradation can refer to either a breakup of the microparticle, that is, dissociation of the polymers forming the microparticles/nanoparticles and/or of the polymers themselves. This can occur as a result of change in pH from the carrier in which the particles are administered to the pH at the site of release, as in the case of the diketopiperazines, hydrolysis, as in the case of poly(hydroxy acids), by diffusion of an ion such as calcium out of the microparticle, as in the case of microparticles or nanoparticles formed by ionic bonding of a polymer such as alginate, and by enzymatic action, as in the case of many of the polysaccharides and proteins. In some cases linear release may be most useful, although in others a pulse release or "bulk release" may provided more effective results.

Representative synthetic materials are: diketopiperazines, poly(hydroxy acids) such as poly(lactic acid), poly(glycolic acid) and copolymers thereof, polyanhydrides, polyesters such as polyorthoesters, polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications routinely made by those skilled in the art.

Bioadhesive polymers include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, and polyacrylates.

For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intrasternal injection and infusion, and intrahepatic arterial administration (including intrahepatic injection and intrahepatic infusion).

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

In certain embodiments, the subject nucleic acids (e.g., RNAi constructs, and enzymatic nucleic acids) of the present application are formulated with a pharmaceutically acceptable carrier. Such therapeutic agents can be administered alone or as a component of a pharmaceuticalal formulation (composition). The agents may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject nucleic acids include those suitable for systemic, local, oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic or anti-infection agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject nucleic acid therapeutic agent as an active ingredient.

In solid dosage forms for oral administration (capsules, tablets, pills, dragees, powders, granules, and the like), one or more nucleic acid therapeutic agents of the present application may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceuticalal compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Methods and compositions of the application can be administered topically, either to skin or to mucosal membranes such as those on the cervix and vagina. This offers the greatest opportunity for direct delivery to unwanted cell proliferation localized to skin or mucosal membranes with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject nucleic acids may be mixed under sterile conditions with a pharmaceutically acceptable carrier, and with any preservatives, buffers, or propellants which may be required. The ointments, pastes, creams and gels may contain, in addition to a subject nucleic acid molecule, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject nucleic acid therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Formulations suitable for inhalation are also provided, and such formulations can be used for pulmonary delivery, which can be localized to the pulmonary system or systemic. Examples of pharmaceutical devices for pulmonary delivery include metered dose inhalers (MDIs) and dry powder inhalers (DPIs). Exemplary delivery systems by inhalation which can be adapted for delivery of the subject R2 inhibitor and/or active agent are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the R2 inhibitor and/or active agent are described in U.S. Pat. Nos. 6,294,153; 6,344,194; 6,071,497, U.S. Patent Application Publication No. 2004/0063654, and PCT applications WO02/066078; WO02/053190; WO01/60420; WO00/66206.

Pressurized metered dose inhalers (pMDIs) are the most commonly used inhaler worldwide. The aerosol is created when a valve is opened (usually by pressing down on the propellant canister), allowing liquid propellant to spray out of a canister. Typically, a drug or therapeutic is contained in small particles (usually a few microns in diameter) suspended in the liquid propellant, but in some formulations the drug or therapeutic may be dissolved in the propellant. The propellant evaporates rapidly as the aerosol leaves the device, resulting in small drug or therapeutic particles that are inhaled. Propellants typically used in such pMDIs include but are not limited to hydrofluoroalkanes (HFAs). A surfactant may also be used, for example, to formulate the drug or therapeutic, with pMDIs. Other solvents or excipients may also be employed with pMDIs, such as ethanol, ascorbic acid, sodium metabisulfate, glycerin, chlorobutanol, and cetylpyridium chloride. Such pMDIs may further include add-on devices such as, for example, spacers, holding chambers and other modifications.

The third type of inhaler is the dry powder inhaler (DPI). In DPIs, the aerosol is usually a powder, contained within the device until it is inhaled. The therapeutic or drug is manufactured in powder form as small powder particles (usually a few millionths of a meter, or micrometers, in diameter). In many DPIs, the drug or therapeutic is mixed with much larger sugar particles (e.g., lactose monohydrate), that are typically 50-100 micrometers in diameter. The increased aerodynamic forces on the lactose/drug agglomerates improve entrainment of the drug particles upon inhalation, in addition to allowing easier filling of small individual powder doses. Upon inhalation, the powder is broken up into its constituent particles with the aid of turbulence and/or mechanical devices such as screens or spinning surfaces on which particle agglomerates impact, releasing the small, individual drug powder particles into the air to be inhaled into the lung. The sugar particles are usually intended to be left behind in the device and/or in the mouth-throat.

One aspect of the application provides an aerosol composition comprising an R2 inibitor. An aerosol composition can be a composition comprising aerosolized R2 inhibitor or a composition comprising an R2 inhibitor in a formulation suitable for aerosolization. The R2 inhibitor may be formulated in combination with an additional active agent, and the combination formulation is suitable for aerosolization. Alternatively, the R2 inhibitor and an additional active agent may be formulated separately, such that they will be combined after aerosolization occurs or after being administered to a subject.

Pharmaceutical compositions suitable for parenteral administration may comprise one or more nucleic acid agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceuticalal compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceuticalal form may be brought about by the inclusion of agents which delay absorption, such as aluminum monostearate and gelatin.

Injectable depot forms are made by forming microencapsule matrices of one or more nucleic acid agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the application with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In certain embodiments, the nucleic acids of the instant application are formulated with a pharmaceutically acceptable agent that allows for the effective distribution of the nucleic acids in the physical location most suitable for their desired activity. Non-limiting examples of such pharmaceutically acceptable agents include: PEG, phospholipids, phosphorothioates, P-glycoprotein inhibitors (such as Pluronic P85) which can enhance entry of drugs into various tissues, biodegradable polymers, such as poly (DL-lactide-coglycolide) microspheres for sustained release delivery after implantation (Emerich, D F et al, 1999, Cell Transplant, 8, 47-58), and loaded nanoparticles such as those made of polybutylcyanoacrylate, which can deliver drugs across the blood brain barrier and can alter neuronal uptake mechanisms (Prog Neuropsychopharmacol Biol Psychiatry, 23, 941-949, 1999).

In other embodiments, certain of the nucleic acids of the instant application can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45). Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al, PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856; all of these references are hereby incorporated in their totalities by reference herein). Gene therapy approaches specific to the CNS are described by Blesch et al., 2000, Drug News Perspect., 13, 269-280; Peterson et al., 2000, Cent. Nerv. Syst. Dis., 485-508; Peel and Klein, 2000, J. Neurosci. Methods, 98, 95-104; Hagihara et al., 2000, Gene Ther., 7, 759-763; and Herrlinger et al., 2000, Methods Mol. Med., 35, 287-312. AAV-mediated delivery of nucleic acid to cells of the nervous system is further described by Kaplitt et al., U.S. Pat. No. 6,180,613.

In another aspect of the application, RNA molecules of the present application are preferably expressed from transcription units (see for example Couture et al., 1996, TIG., 12, 510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acids are delivered as described above, and persist in target cells. Alternatively, viral vectors can be used that provide for transient expression of nucleic acids. Such vectors can be repeatedly administered as necessary. Once expressed, the nucleic acid binds to the target mRNA. Delivery of nucleic acid expressing vectors can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

In one aspect, the application contemplates an expression vector comprising a nucleic acid sequence encoding at least one of the nucleic acids of the instant application. The nucleic acid sequence is operably linked in a manner which allows expression of the nucleic acid of the application. For example, the application features an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant application; and wherein said sequence is operably linked to said initiation region and said termination region, in a manner which allows expression and/or delivery of said nucleic acid. The vector can optionally include an open reading frame (ORF) for a protein operably linked on the 5' side or the 3'-side of the sequence encoding the nucleic acid catalyst of the application; and/or an intron (intervening sequences).

In certain embodiments including double stranded nucleic acids, the two strands can be expressed separately and then hybridize in a cell. Such separate expression may be through separate expression constructs or through a single expression construct. Alternatively, the two strands can be expressed together, for example, the two strands of a hairpin RNA may be expressed together.

Regardless of the route of administration selected, the R2 inhibitors of the present application, which may be used in a suitable hydrated form, and/or the pharmaceutical compositions of the present application, are formulated into pharmaceutically acceptable dosage forms such as described below or by other conventional methods.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular R2 inhibitor of the present application employed, or the ester, salt or amide thereof, the route of administration, the time of administration, the rate of excretion of the particular compound being employed, the duration of the treatment, other drugs, compounds and/or materials used in combination with the particular R2 inhibitor employed, the age, sex, weight, condition, general health and prior medical history of the patient being treated, and like factors well known in the medical arts.

A physician or veterinarian can readily determine and prescribe the effective amount of the pharmaceutical composition required. For example, the physician or veterinarian could start doses of the R2 inhibitors of the application employed in the pharmaceutical composition at levels lower than that required in order to achieve the desired therapeutic effect and gradually increase the dosage until the desired effect is achieved.

In general, a suitable daily dose of an R2 inhibitor of the application will be that amount of the compound that is the lowest dose effective to produce a therapeutic effect. Such an effective dose will generally depend upon the factors described above. Generally, intravenous, intracerebroventricular, and subcutaneous doses for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

Pharmaceutical formulations of the present application also include veterinary compositions, e.g., pharmaceutical preparations of the R2 inhibitors suitable for veterinary uses, e.g., for the treatment of livestock or domestic animals, e.g., dogs. The patient receiving this treatment is any animal in need, including primates, in particular humans, and other non-human mammals such as equines, cattle, swine and sheep; and poultry and pets in general.

The R2 inhibitors may also be formulated for non-pharmaceutical uses, for example, for use as disinfectant to remove pathogens from any pathogen-contaminated objects, or for use as a cosmetic to remove unwanted hair growth. A cosmetic composition can be formulated similarly as certain pharmaceutical compositions (e.g., lotion, ointment, film, patch, etc.) described herein.

The R2 inhibitors such as RNAi constructs of the application may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNAi constructs can be provided in formulations also including penetration enhancers, carrier compounds and/or transfection agents.

Representative United States patents that teach the preparation of such uptake, distribution and/or absorption assisting formulations which can be adapted for delivery of RNAi constructs, particularly siRNA molecules, include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The RNAi constructs of the application also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to RNAi constructs and pharmaceutically acceptable salts of the siRNAs, pharmaceutically acceptable salts of such RNAi constructs, and other bioequivalents.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For siRNAs, examples of pharmaceutically acceptable salts include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

An exemplary composition comprises an RNAi construct mixed with a delivery system, such as a liposome system, and optionally including an acceptable excipient. In certain embodiments, the composition is formulated for topical administration for, e.g., herpes virus infections.

Figure 27:
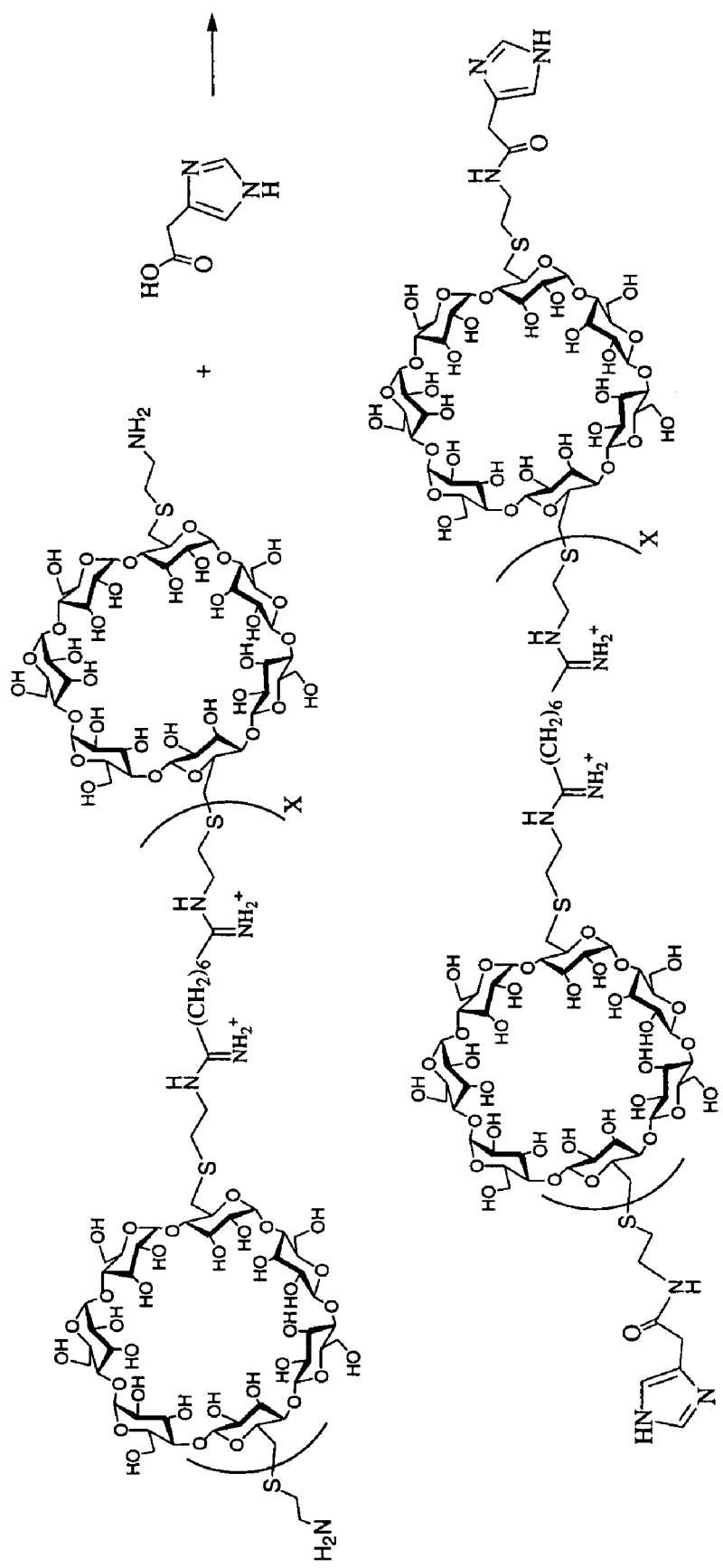
FIG. 27 is a schematic representation of CDP end group functionalization to make im-CDP (imidazole-containing CDP).
Figure 42:
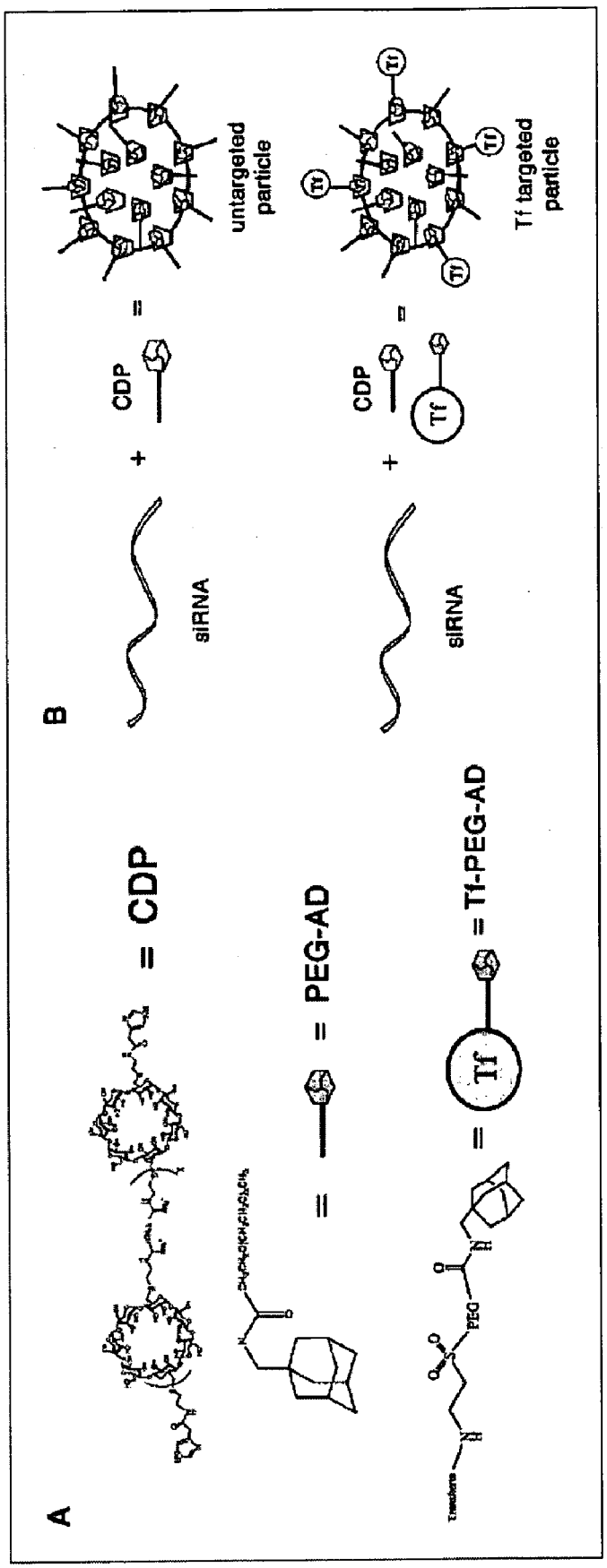
FIG. 42 shows assembly of transferrin (Tf)-targeted particles for delivery of siRNA.

In certain embodiments, the subject nucleic acids are delivered using polymeric vehicles. The polymeric vehicle may form a microparticle with one or more subject nucleic acids. In certain embodiments, particularly where systemic administration is desirable, the nanoparticles may have a size that is about 10 nm, 20 nm, 30 nm, 40 nm, 50 nm, 60 nm, 70 nm, 80 nm, 90 nm, 100 nm, 120 nm, 150 nm, 200 nm or greater in diameter. In certain embodiments, the nanoparticles may have a size that is about 10-120 nm, 10-100 nm, 50-120 nm, 50-100 mm, 10-70 nm, 50-70 nm, or about 50 nm in diameter. In certain embodiments, the nanoparticle comprises cyclodextrin. In particular embodiments, the nanoparticle comprises cyclodextrin copolymers, for example, the linearized cyclodextrin copolymers as described in U.S. Pat. No. 6,509,323 and U.S. Patent Application Publication No. 2002/0151523 and cyclodextrin-based polymers as described in U.S. Patent Application Publication Nos. 2004/0077595 and 2004/0109888. In particular embodiments, the cyclodextrin is modified, for example, having a functionalized end group, such as the im-CDP described herein, for example, as depicted in FIGS. 27 and 42. In certain embodiments, the nucleic acids are delivered using inclusion complexes such as those described in U.S. Patent Application Publication Nos. 2003/0008818, 2003/0017972 and 2004/0063654. In certain embodiments, the delivery system or vehicle may be further include one or more modifiers or modifying components, for example, a modifier that can change the surface chemistry of a microparticle. The modifier may be an anionic component. The modifier may be a ligand that targets to certain tissue(s) or cell type(s), as described below. The modifier may be a polyethylene glycol (PEG) molecule, for example, a PEG5000 molecule.

In certain embodiments, the R2 inhibitors or pharmaceutical compositions thereof can be associated with one or more ligands effective to bind to specific cell surface proteins or matrix on the target cell, thereby facilitating sequestration of the complex to target cells, and in some instances, enhancing uptake of the RNAi construct by the cell. Merely to illustrate, examples of ligands suitable for use in targeting the supramolecular complexes and liposomes of the present invention to specific cell types are listed in the Table below.

TABLE 9

Suitable ligands for targeted delivery to a variety of cell types.

| Ligand | Receptor | Cell type |
| --- | --- | --- |
| folate | folate receptor | epithelial carcinomas, bone marrow stem cells |
| water soluble vitamins | vitamin receptor | various cells |
| pyridoxyl phosphate | CD4 | CD4 + lymphocytes |
| apolipoproteins | LDL | liver hepatocytes, vascular endothelial cells |
| insulin | insulin receptor | |
| transferrin | transferrin receptor | endothelial cells |
| galactose | asialoglycoprotein receptor | liver hepatocytes |
| sialyl-Lewis$_X$ | E, P selectin | activated endothelial cells |
| Mac-1 | L selectin | neutrophils, leukocytes |

TABLE 9-continued

Suitable ligands for targeted delivery to a variety of cell types.

| Ligand | Receptor | Cell type |
| --- | --- | --- |
| VEGF | Flk-1, 2 | tumor epithelial cells |
| basic FGF | FGF receptor | tumor epithelial cells |
| EGF | EGF receptor | epithelial cells |
| VCAM-1 | $a_4b_1$ integrin | vascular endothelial cells |
| ICAM-1 | $a_Lb_2$ integrin | vascular endothelial cells |
| PECAM-1/CD31 | $a_vb_3$ integrin | vascular endothelial cells, activated platelets |
| osteopontin | $a_vb_1$ integrin $a_vb_5$ integrin | endothelial cells and smooth muscle cells in atherosclerotic plaques |
| RGD sequences | $a_vb_3$ integrin | tumor endothelial cells, vascular smooth muscle cells |
| HIV GP 120/41 or GP120 | CD4 | CD4 + lymphocytes |

In certain embodiments, the R2 inhibitors or pharmaceutical compositions thereof can be associated with one or more targeting ligands comprising galactose. Exemplary ligands that comprise galactose include, for example, lactose and similar molecules. The hepatic asialoglycoprotein receptor (ASGPR) is a C-type lectin that is expressed on the surface of hepatocytes. ASGPR binds glycoproteins with terminal β-D-galactose (Gal) or N-acetylgalactosamine (GalNAc). The affinity of ligands for the ASGPR is dependent on type (Gal vs. GalNAc), number (tetraantennary>triantennary>>biantennary>>monantennary) and arrangement of multiantennary residues. Each polypeptide subunit of the ASGPR (human is a tetramer) can bind a single terminal Gal or GalNAc.

OTHER EMBODIMENTS

In certain embodiments, the application provides a delivery vehicle that is suitable for liver specific delivery of a therapeutic agent, such as an inhibitor nucleic acid described herein. The liver specific delivery vehicle comprises (1) a host component comprising the imadazole modified cyclodextrin containing polymer shown in FIG. 27 and (2) a guest component comprising the adamantane-PEG-galactose molecule shown in FIG. 32. When mixed together with one or more therapeutic agent(s), the guest and host components form an inclusion complex, or polyplex, that encapsulates the therapeutic agent(s) in the polymer to form a particulate composition (see FIG. 31). In certain embodiments, the delivery vehicle is formulated so as to provide a particulate composition having a mean diameter of about 30-100 nm, about 40-70 nm, about 50-70 nm, about 50-60 nm, or about 50 nm.

In various embodiments, the liver specific delivery vehicle may be used to delivery any type of therapeutic agent to the liver, for example, for treating a liver specific disease or disorder, or for treating a disease or disorder involving or affecting the liver.

A liver therapeutic agent of the invention can be a small molecule, a peptide or a peptide analog, such as for example, a peptidomimetic, and a nucleic acid. A nucleic acid liver therapeutic agent of the invention can be an antisense RNA, an RNAi construct (e.g., an siRNA), or a ribozyme. A nucleic acid liver therapeutic agent may also be a gene therapy construct, such as for example, an expression construct that delivers a gene to be expressed in hepatocytes.

A liver therapeutic agent of invention is effective against a liver disease or condition, such as for example, a human liver disease or condition. A liver disease or condition may be caused by unwanted proliferation of cells, such as for example, hepatocytes or pathogens in the liver. Methods and compositions of the inventions may be useful or effective against any liver disease or condition, including, but not limited to, liver cancer (e.g., hepatocellular carcinoma or liver metastases of other cancers, such as for example, pancreatic cancer), hepatitis A, hepatitis B, hepatitis C, hepatitis D, hepatitis E, hepatitis G, autoimmune hepatitis, cirrhosis, Alagille syndrome, alcoholic liver disease, alpha-1-antitrypsin deficiency, Budd-Chiari syndrome, biliary atresia, Byler disease, Caroli disease, Crigler-Najjar syndrome, Dubin-Johnson syndrome, fatty liver, galactosemia, Gilbert syndrome, Glycogen Storage disease I, hemangioma, hemochromatosis, Itching in Liver disease, liver transplantation, porphyria cutanea tarda, primary biliary cirrhosis, protoporphyria, erythrohepatic, Rotor syndrome, sclerosing cholangitis, and Wilson disease. Accordingly, a pharmaceutical composition of the invention can be effective against one or more liver diseases or conditions, such as those described herein.

In certain embodiments, a liver therapeutic agent of the invention targets a hepatocyte-specific gene, such as for example, by regulating (inhibiting or promoting) the expression of the hepatocyte-specific gene. A hepatocyte-specific gene generally includes any gene with a higher expression level in hepatocytes than in other cells (e.g., Kupffer cells) or tissues.

In certain embodiments, a liver therapeutic agent targets a gene that is dysregulated in hepatocytes of a patient with a liver disease or condition. The gene may be a hepatocyte-specific gene. Alternatively, the gene is not a hepatocyte-specific gene, such as for example, a gene with similar or lower level of expression in hepatocytes as compared to other cells and tissues, and the expression and/or activity of that gene is altered in hepatocytes of a patient with a liver disease or condition as compared to hepatocytes from a normal liver. For example, ribonucleotide reductase subunit II (R2) is dysregulated in hepatocellular carcinoma, that is, R2 is expressed in hepatocellular carcinoma cells that proceed through cell cycling, but is not expressed in normal hepatocytes that are generally quiescent. A liver therapeutic agent targeting R2 may be a nucleic acid agent that specifically reduces or inhibits expression of R2, and such a nucleic acid agent can be an antisense molecule, an RNAi construct (e.g., an siRNA construct), or a ribozyme.

A liver therapeutic agent may also target a liver-specific molecule or genomic region, such as a liver cancer-specific transcriptional regulatory element (TRE), preferably a CRG-L2 regulatory sequence, as described in U.S. Patent Application Publication No. 20050124068. A liver therapeutic agent may also target a nucleic acid (a gene or a genomic region) associated with one or more liver diseases or conditions, such as those nucleic acids described in U.S. Patent Application Publication No. 20040241657.

A liver therapeutic agent may inhibit or promote liver growth, for example, by inhibiting or promoting hepatocyte proliferation. Such agents can be useful in liver protection, examples of which are described in U.S. Patent Application Publication No. 20040170613.

Another aspect of the invention provides methods for treating a patient having a liver disease or condition. The method generally comprises systemically administering to the patient a therapeutically effective amount of a pharmaceutical composition of the invention. System administration can be achieved via various routes of delivery, such as for example, i.v. or i.p. injection, transdermal delivery, pulmonary delivery, or oral uptake.

Methods and compositions of the inventions may be useful or effective against any liver disease or condition, including, but not limited to, liver cancer (e.g., hepatocellular carcinoma or liver metastases of other cancers, such as for example, pancreatic cancer), hepatitis A, hepatitis B, hepatitis C, hepatitis D, hepatitis E, hepatitis G, autoimmune hepatitis, cirrhosis, Alagille syndrome, alcoholic liver disease, alpha-1-antitrypsin deficiency, Budd-Chiari syndrome, biliary atresia, Byler disease, Caroli disease, Crigler-Najjar syndrome, Dubin-Johnson syndrome, fatty liver, galactosemia, Gilbert syndrome, Glycogen Storage disease I, hemangioma, hemochromatosis, Itching in Liver disease, liver transplantation, porphyria cutanea tarda, primary biliary cirrhosis, protoporphyria, erythrohepatic, Rotor syndrome, sclerosing cholangitis, and Wilson disease.

Methods and compositions of the inventions are useful in delivering liver therapeutic agents, including medications currently available or under development (e.g., in clinical trials). The invention contemplates a variety of liver therapeutic agents, including, but not limited to, small molecule agents, peptides or peptide analogs (including peptidomimetics), nucleic acid agents (such as for example, RNAi constructs including siRNA constructs, antisense molecules, enzymatic nucleic acids, or other gene therapy constructs), or vaccines.

Alagille syndrome, or AGS, is one of the major forms of chronic liver disease in childhood with severe morbidity and a mortality of 10 to 20%. It has been reported that AGS is caused by mutation in the Jagged-1 gene (JAG1). See, e.g., Alagille et al., J. Pediat. 86: 63-71, 1975; Anad et al., J. Med. Genet. 27: 729-737, 1990; Kamath et al., J. Med. Genet. 40: 891-895, 2003. Accordingly, a liver therapeutic agent may be an AGS therapeutic agent (or medication effective against AGS), and an AGS therapeutic agent may include a gene therapy construct that targets the mutated JAG1 gene.

Alcohol abuse is a leading cause of morbidity and mortality throughout the world. Alcohol affects many organ systems of the body, but perhaps most notably affected are the central nervous system and the liver. Almost all ingested alcohol is metabolized in the liver and excessive alcohol use can lead to acute and chronic liver disease. Liver cirrhosis resulting from alcohol abuse is one of the ten leading causes of death in the United States. Alcohol abuse generally leads to three pathologically distinct liver diseases. In clinical practice, any or all of these three conditions can occur together, at the same time, in the same patient. These three conditions are: (1) Fatty Liver (Steatosis): Alcohol abuse can lead to the accumulation of fat within hepatocytes, the predominant cell type in the liver. A similar condition can also be seen in some obese people who are not alcohol abusers. Fatty liver is reversible if the patient stops drinking, however, fatty liver can lead to steatohepatitis. Steatohepatitis is fatty liver accompanied by inflammation and this condition can lead to scarring of the liver and cirrhosis. (2) Hepatitis: Alcohol can cause acute and chronic hepatitis. The patient who presents with alcoholic hepatitis is usually a chronic drinker with a recent episode of exceptionally heavy consumption. Other presentations are also possible. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). (3) Cirrhosis is characterized anatomically by widespread nodules in the liver combined with fibrosis. The fibrosis and nodule formation causes distortion of the normal liver architecture which interferes with blood flow through the liver. Cirrhosis can also lead to an inability of the liver to perform its biochemical functions. In the United States, alcohol abuse is the leading cause of liver cirrhosis. Anatomically, alcoholic cirrhosis is almost always micronodular (i.e. the regenerating liver nodules are small).

Cirrhosis can also be caused by any chronic liver disease, such as chronic hepatitis B, C, and D, chronic autoimmune hepatitis, inherited metabolic diseases (e.g. hemochromatosis, Wilson disease), chronic bile duct diseases, chronic congestive heart failure, parasitic infections (e.g. schistosomiasis), nonalcoholic steatohepatitis (liver inflammation that can be caused by fatty liver), or long term exposure to toxins or drugs.

Treatment of cirrhosis generally depends upon the underlying etiology. Termination of alcohol intake will stop the progression in alcoholic cirrhosis and for this reason, it is important to make the diagnosis early in a chronic alcohol abuser. Similarly, discontinuation of a hepatotoxic drug or removal of an environmental toxin will stop progression. Treatment of metabolic diseases, such as treatment of iron overload in hemochromatosis or copper overload in Wilson disease, are also effective therapies. Chronic viral hepatitis B and C may respond to treatment with interferon and autoimmune hepatitis may improve with prednisone and azathioprine (Imuran). Drugs such as ursodiol (Actigall) may slow the progression of primary biliary cirrhosis and possibly sclerosing cholangitis. Liver transplantation is highly effective for the treatment of end-stage cirrhosis.

Cholestasis, or progressive familial intrahepatic 1 or PFIC1 and benign recurrent intrahepatic cholestasis (BRIC) are caused by mutation in the ATP8B1 gene. A second form of progressive familial intrahepatic cholestasis (PFIC2) is caused by mutation in a liver-specific ATP-binding cassette (ABC) transporter (BSEP). PFIC3 is caused by mutation in the class III multidrug resistance P-glycoprotein (MDR3). PFIC4 is caused by mutation in 3-beta-hydroxy-delta-5-C27-steroid oxidoreductase (HSD3B7). See e.g., Ghent et al., J. Pediat. 93: 127-132, 1978; Trauner et al., New Eng. J. Med. 339: 1217-1227, 1998; Whitington et al., J. Pediat. Gastroent. Nutr. 18: 134-141, 1994.

Liver cancer can be any of the following non-limiting examples: metastatic cancers of the liver, cholangiocarcinoma, or hepatocellular carcinoma.

Metastatic cancers are tumors that spread from the organ or origin. Because of its blood supply, the liver is a common site for some cancers to spread. Some of the most common cancers that spread to the liver are those originating in the colon, pancreas, lung and breast. Lymphomas and leukemias can also invade the liver. Cholangiocarcinoma is cancer that arises from bile ducts cells within the liver. Cholangiocarcinoma can also arise in the bile ducts that are outside of the liver proper.

Hepatocellular carcinoma is cancer that arises from hepatocytes, the major cell type of the liver. Worldwide, hepatocellular carcinoma is among top two leading causes of cancer death. It is especially prevalent in parts of Asia and Africa. About 80% of people with hepatocellular carcinomas have cirrhosis. Chronic infection with the hepatitis B virus and hepatitis C virus also increases the risk of developing hepatocellular carcinoma. Aflatoxins, which are produced by a mold that is a contaminant of nuts (most commonly peanuts), grains, and beans, have also been implicated as a major risk factor for causing hepatocellular carcinoma. Although virtually non-existent in the United States, aflatoxins, are common in other parts of the world and often contaminate food.

Dubin-Johnson syndrome is caused by mutations in the canalicular (apical part of a hepatocyte) multispecific organic anion transporter (CMOAT), which is also termed multidrug resistance-associated protein-2 (MRP2) and plays an important role in biliary organic anion transport. Wada et al., Hum. Molec. Genet. 7: 203-207, 1998.

The hereditary hyperbilirubinemias (Wolkoff et al., in The Metabolic Basis of Inherited Disease. New York: McGraw-Hill (pub.) (5th ed.) 1983. Pp. 1385-1420.) include (1) those resulting in predominantly unconjugated hyperbilirubinemia: Gilbert or Arias syndrome, Crigler-Najjar syndrome type I, and Crigler-Najjar syndrome type II; and (2) those resulting in predominantly conjugated hyperbilirubinemia: Dubin-Johnson syndrome, Rotor syndrome, and several forms of intrahepatic cholestasis. Detailed studies show that patients with Gilbert syndrome have reduced activity of bilirubin glucuronosyltransferase. Bosma et al., New Eng. J. Med. 333: 1171-1175, 1995. But it has been shown that Gilbert syndrome is caused by mutation in the UDP-glucuronosyltransferase gene (UGT1A1). Mutations in the same gene cause Crigler-Najjar syndrome type I and Crigler-Najjar syndrome type II. Accordingly, liver therapeutic agents targeting UGT1A1 can be effective against these hereditary hyperbilirubinemias.

Fatty liver condition is also called steatosis, and fatty liver with liver inflammation is called or steatohepatitis. Steatosis and steatohepatitis can be caused by alcohol and other drugs and can also sometimes occur in patients with diabetes mellitus. Steatohepatitis not caused by alcohol is sometimes referred to as non-alcoholic steatohepatitis or "NASH."

Classic galactosemia is caused by mutation in the galactose-1-phosphate uridylyltransferase gene (GALT).

Glycogen storage disease is caused by a defect in glucose-6-phosphatase. The liver and kidney are involved in this disorder, and hypoglycemia is a major problem. This disorder is also linked to hepatocellular adenoma. Bianchi, Eur J Pediatr. 1993; 152 Suppl 1:S63-70.

There are two types of liver hemangioma: cavernous and hemangioendothelioma. Hemangioendotheliomata are generally seen only in children. Cavernous hemangioma is the most common benign liver tumor of adults, although it occurs in individuals of all ages and throughout the world.

Classic hemochromatosis (HFE), an autosomal recessive disorder, is most often caused by mutation in a gene designated HFE on chromosome 6p21.3. It has also been found to be caused by mutation in the gene encoding hemojuvelin (HJV), which maps to 1q21. Juvenile hemochromatosis, or hemochromatosis type 2 (HFE2), is also autosomal recessive. One form, designated HFE2A, is caused by mutation in the HJV gene. A second form, designated HFE2B, is caused by mutation in the gene encoding hepcidin antimicrobial peptide (HAMP), which maps to 19q13. Hemochromatosis type 3 (HFE3), an autosomal recessive disorder, is caused by mutation in the gene encoding transferrin receptor-2 (TFR2), which maps to 7q22. Hemochromatosis type 4 (HFE4), an autosomal dominant disorder, is caused by mutation in the SLC40A1 gene, which encodes ferroportin and maps to 2q32. The clinical features of hemochromatosis include cirrhosis of the liver, diabetes, hypermelanotic pigmentation of the skin, and heart failure. Primary hepatocellular carcinoma (HCC), complicating cirrhosis, is responsible for about one-third of deaths in affected homozygotes. Since hemochromatosis is a relatively easily treated disorder if diagnosed, this is a form of preventable cancer.

The term hepatitis A (HA) or type A viral hepatitis has replaced all previous designations: infectious hepatitis, epidemic hepatitis, epidemic jaundice, catarrhal jaundice, infectious icterus, Botkins disease, and MS-1 hepatitis. Hepatitis A is diagnosed by finding IgM-class anti-HAV in serum collected during the acute or early convalescent phase of disease. Hepatitis A virus (HAV) is classified with the enterovirus group of the Picornaviridae family. HAV has a single molecule of RNA surrounded by a small (27 nm diameter) protein capsid and a buoyant density in CsCl of 1.33 g/ml.

Hepatitis B is generally caused by hepatitis B virus (HBV), a mostly double-stranded DNA virus in the Hepadnaviridae family. HBV causes hepatitis in human and related virus in this family cause hepatitis in ducks, ground squirrels and woodchucks. The HBV genome has four genes: pol, env, pre-core and X that respectively encode the viral DNA-polymerase, envelope protein, pre-core protein (which is processed to viral capsid) and protein X. The function of protein X is not clear but it may be involved in the activation of host cell genes and the development of cancer.

Alpha-interferons were the first drugs approved in the United States for the treatment of chronic hepatitis B. Interferon treatment is recommended for individuals who have "replicative disease" (HBeAg positive). About 40% of such individuals will lose serum HBeAg after 16 weeks of treatment with interferon-alpha. Loss of HBeAg is correlated with an improved prognosis. A few treated patients (less than 10%) may even be cured as assessed by the loss of HBsAg. Other treatment options for chronic hepatitis B include nucleoside analogues. In December, 1998, the United States Food and Drug Administration (FDA) approved lamivudine, also known as 3TC and is also effective against HIV, for the treatment of chronic hepatitis B (patients who are HBeAg positive). Lamivudine is taken orally at 100 mg/day for chronic hepatitis B. In studies where they were compared, lamivudine was equally effective to interferon-alpha in inducing a loss of serum HBeAg. It also has been shown to improve liver biopsy results in patients treated for one year. In September 2002, the FDA approved adevofir dipivoxil, another nucleoside analogue also effective against HIV, for the treatment of hepatitis B. The dose is 10 mg/day for chronic hepatitis B. At the present time, other nucleoside analogues are being studied in clinical trials. The combination of interferon-alpha and a nucleodide analogue, two nucleoside analogues together (such as lamivudine and adefovir) are also under investigation. Other nucleoside analogues such as famciclovir, lobucavir, and adfovir have also been studied for combination therapy to treat chronic hepatitis B. Yao and Gishi, Current Gastroenterology Reports 1999, 1:20-26

Approximately 170,000,000 people worldwide and 4,000,000 in the United States are infected with hepatitis C virus (HCV). The virus is transmitted primarily by blood and blood products. About 85% of individuals acutely infected with HCV become chronically infected. Hence, HCV is a major cause of chronic (lasting longer than six months) hepatitis. Once chronically infected, the virus is almost never cleared without treatment. In rare cases, HCV infection causes clinically acute disease and even liver failure, however, most instances of acute infection are clinically undetectable. HCV is a positive, single-stranded RNA virus in the Flaviviridae family. The genome is approximately 10,000 nucleotides and encodes a single polyprotein of about 3,000 amino acids. The polyprotein is processed by host cell and viral proteases into three major structural proteins and several non-structural protein necessary for viral replication. Several different genotypes of HCV with slightly different genomic sequences have since been identified that correlate with differences in response to treatment with interferon alpha. All current treatment protocols for hepatitis C are based on the use of various preparations of interferon alpha, which are administered by intramuscular or subcutaneous injection. Interferon alfa-2a (Roferon-A; Hoffmann-La Roche), inteferon alpha-2b (Intron-A; Schering-Plough) and interferon alfacon-1 (Infergen; Intermune) are all approved in the United States for the treatment of adults with chronic hepatitis C as single agents. Peginterferon alpha, sometimes called pegylated interferon, has also been available for the treatment of chronic hepatitis C. There are two preparations of peginterferon alpha that have been studied in patients with hepatitis C: peginterferon alpha-2b (Peg-Intron; Schering-Plough) and peginterferon alpha-2a (Pegasys; Hoffmann-La Roche). With peginterferon alpha-2a alone, approximately 30% to 40% of patients achieve a sustained response to treatment for 24 to 48 weeks. Zeuzem et al., New England Journal of Medicine. 2000; 343:1666-1172; Heathcote et al. New England Journal of Medicine. 2000; 343: 673-1680. The addition of ribavirin to interferon alpha is superior to interferon alpha alone in the treatment of chronic hepatitis C. Ribavirin is a synthetic nucleoside that has activity against a broad spectrum of viruses. FDA also approved interferon alpha-2b plus ribavirin for the treatment of individuals with chronic hepatitis C who relapsed after previous interferon alpha therapy. Further, the combination of interferon alpha-2b plus ribavirin is more effective in achieving a sustained response than interferon alpha-2b alone in the treatment of patients with chronic hepatitis C not previously treated with interferon, and this led to FDA approval for this indication in December 1998. The FDA has also approved the combination of peginterferon alpha plus ribavirin for the treatment of chronic hepatitis C.

Clinical trials of peginterferon-alpha with a compound called VX-497 (Vertex Pharmaceuticals) are also in progress. VX-497 has some features similar to ribavirin and inhibits a cellular enzyme know as inosine monophosphate dehydrogenase that may responsible for some of its effects. A new generation of drugs or therapeutic agents to treat hepatitis C include those designed specifically to inhibit functions of the hepatitis C virus. One target for such drugs is the hepatitis C virus RNA genome. A ribozyme (Hepatazyme, Ribozyme Pharmaceuticals) has been designed to cleave the hepatitis C virus RNA genome in a region that the virus needs to survive. Its efficacy in cutting hepatitis C virus RNA has been established in the test tube and the drug is now in early clinical trials. ISIS-14803 (Isis Pharmaceuticals) is an antisense inhibitor complementary to a conserved sequence of the hepatitis C virus RNA. This molecule binds to the viral RNA and inhibits the expression of proteins required for replication. ISIS-14803 is currently in early stage clinical trials. A small molecule known as VP-50406 (ViroPharma) has also been demonstrated to inhibit hepatitis C virus RNA in the laboratory and is in early stage clinical development. Inhibitors of a unique structure of the hepatitis C virus RNA necessary for protein synthesis, known as the internal ribosome entry site or IRES, are also under study in the laboratory.

The hepatitis D virus (also called delta virus) is a small circular RNA virus. The hepatitis D virus is replication defective and therefore cannot propagate in the absence of another virus. In humans, hepatitis D virus infection only occurs in the presence of hepatitis B infection. Interferon-alpha is used to treat patients with chronic hepatitis B and hepatitis D infection.

Hepatitis E virus (HEV) has a single-stranded polyadenylated RNA genome of approximately 8 kb. Based on its physicochemical properties it is presumed to be a calici-like virus. The disease caused by HEV is called hepatitis E, or enterically transmitted non-A non-B hepatitis (ET-NANBH). Other names include fecal-oral non-A non-B hepatitis, and A-like non-A non-B hepatitis.

Hepatitis G virus (HGV) is a flavivirus related to HCV.

At present there are several medications that are used for the treatment of itch in liver disease. These medications include cholestyramine, the antibiotic rifampicin, the opiate antagonists naloxone and naltrexone, and the serotonin type-3 receptor antagonist. Clinical trial on the use of the drug gabapentin for the treatment of the itch due to liver disease (IRB Protocol #9618).

Porphyria cutanea tarda is an autosomal dominant disorder characterized by light-sensitive dermatitis and associated with the excretion of large amounts of uroporphyrin in urine. Reduced liver and red cell uroporphyrinogen decarboxylase activity has been reported in familial (Kushner et al., 1976 Clin. Invest. 58: 1089-1097; Lehr and Doss, 1981, Dtsch. Med. Wschr. 106: 241-245) and sporadic cases of porphyria cutanea tarda (Elder et al., 1978, New Eng. J. Med. 299: 274-278; Felsher et al., 1978, New Eng. J. Med. 299: 1095-1098).

Primary biliary cirrhosis (PBC) is a disease characterized by inflammatory destruction of the small bile ducts within the liver. PBC eventually leads to cirrhosis of the liver. The cause of PBC is unknown, but because of the presence of autoantibodies, it is generally thought to be an autoimmune disease. Other etiologies, such as infectious agents, have not been completely excluded. Patients with PBC are recommended to take vitamins and calcium to help prevent osteoporosis (loss of bone), a common complication of this disease. Colchicine may play a role in inhibiting liver fibrosis and improves laboratory values but not signs or symptoms. Various immunosuppressive agents have been studied in patients with PBC. Corticosteroids are probably not effective and may aggravate the osteoporosis commonly present in patients with PBC. Azathioprine (Imuran), methotrexate and cyclosporin A have been examined in several studies. Ursodiol (Actigall or Urso), a bile acid, has been shown to improve the laboratory and clinical parameters in patients with PBC and the results of one study suggest that it may slow the progression of the disease. Orthotopic liver transplantation is highly successful in patients with end-stage liver disease resulting from PBC.

Erythrohepatic protoporphyria, or EPP, is inherited as an autosomal dominant with incomplete penetrance. Using haplotype segregation analysis, Gouya et al. (2002) identified an intronic single-nucleotide polymorphism (SNP), IVS3-48T-C (177000.0015), which modulates the use of a constitutive aberrant acceptor splice site 63 bp upstream of the normal one. The aberrantly spliced mRNA is degraded by a nonsense-mediated decay mechanism (NMD), producing a decreased steady-state level of mRNA and the additional FECH enzyme deficiency necessary for EPP phenotypic expression.

Primary sclerosing cholangitis (PSC) is a chronic liver disease characterized by inflammation, destruction and fibrosis of the intrahepatic and extrahepatic bile ducts that leads to cirrhosis of the liver. PSC is often complicated by recurrent episodes of bacterial cholangitis (infection of the bile ducts with bacteria). Patients with PSC also have an increased risk of cholangiocarcinoma (bile duct cancer). Orthotopic liver transplantation is highly effective in the treatment of patients with advanced liver disease caused by PSC.

Wilson disease is an autosomal recessive disorder characterized by dramatic build-up of intracellular hepatic copper with subsequent hepatic and neurologic abnormalities. In Wilson disease, the basal ganglia and liver undergo changes that express themselves in neurologic manifestations and signs of cirrhosis, respectively. A disturbance in copper metabolism is somehow involved in the mechanism. Beam, In: Stanbury et al.: The Metabolic Basis of Inherited Disease. New York: McGraw-Hill (pub.) (3rd ed.) 1972. Pp. 1033-1050.

Liver transplantation may be recommended for certain liver diseases or conditions for which other treatment has failed. Examples of such liver diseases or conditions include: Hepatitis B, Hepatitis C, Urea Cycle defects, Familial hypercholesterolemia, Alcohol induced cirrhosis, Glycogen Storage Disease, Autoimmune Hepatitis, Primary Hyperoxaluria type I, Cryptogenic cirrhosis, Crigler-Najjar syndrome type I, Congenital Hepatic Fibrosis, Neimann-Pick Disease, Primary Biliary Cirrhosis, Familial Amyloidosis, Biliary Atresia, Hepatocellular Carcinoma, Primary Sclerosing Cholangitis, Hepatoblastoma, Alagille Syndrome, Hemangioendothelioma, Familial Cholestasis, Non-Carciniod neuro-endocrine, Drug induced liver failure, Liver tumors, Acute/fulminant liver failure, Budd-Chiari syndrome, Alpha-1-antitrypsin deficiency, Wilson Disease, Hemochromatosis, Tyrosinemia, Protoporphyria, or Cystic fibrosis.

EXEMPLIFICATION

The disclosure now being generally described, it will be more readily understood by reference to the following examples, which are included merely for purposes of illustration of certain aspects and embodiments of the present disclosure, and are not intended to limit the disclosure.

Example 1 siRNA Design and Testing

RNA interference, or RNAi, is a gene silencing mechanism originally described in plants (where it was known as post-transcriptional gene silencing, or PTGS), *C. elegans* and *Drosophila* (reviewed in Bernstein et al., 2001; Carmell et al., 2002). In the current model, the RNAi pathway is activated by a double stranded RNA (dsRNA) "trigger" that is then processed into short, 21-23 nucleotide dsRNAs referred to as small interfering RNAs (siRNAs) by the cellular enzyme Dicer. The siRNAs become incorporated into the RNA-induced silencing complex (RISC), where the siRNA antisense strand serves as a guide to target the homologous mRNA for endonucleolytic cleavage within the siRNA/target duplex, approximately 10 bases from the 5' end of the siRNA guide. In mammalian cells, dsRNA longer than 30 nucleotides triggers the nonspecific interferon pathway rather than RNAi. However, Tuschl and colleagues demonstrated (Elbashir et al., 2001a; Harborth et al., 2001; Caplen et al., 2002) that shorter siRNAs exogenously introduced into mammalian cells bypass the Dicer step and directly activate homologous mRNA degradation, without initiating the interferon response. Subsequently, a number of labs demonstrated the feasibility of expressing siRNAs and the related short hairpin RNAs (shRNAs) in vivo against human viral and cellular targets. Advances in RNAi are rapidly expanding and considerable progress has already been made toward therapeutic applications (Zamore, 2001; Kitabwalla and Ruprecht, 2002; Martinez et al., 2002; Couzin, 2003; Scherr et al., 2003; Wilson et al., 2003; Hannon and Rossi, 2004).

Synthetic siRNAs are the method of choice for exogenous, short-term applications. Currently, unmodified siRNAs mediate RNAi effects that typically peak at 2-3 days post-transfection. The most common design for synthetic siRNAs mimics the endogenous siRNAs produced by Dicer cleavage of trigger dsRNA (Elbashir et al., 2001a), where the sense and antisense strands are 21-23 nucleotides long. The annealed portion of the duplex is completely complementary, except for two nucleotide overhangs at both 3' ends. For synthetic siRNAs, the 3' dinucleotide overhangs can be derived from the target sequence, as in their natural counterparts. While siRNAs constructed from 21-23-mers are sufficient for most purposes, oligomers of up to 29 nucleotides can be used without initiating the interferon response. We have observed that siRNAs that are produced from longer double stranded RNAs in cells by the action of Dicer can be up to 100 times more potent than a 21mer provided exogenously (Kim et al., 2005). A companion manuscript by Siolas et al. (2005) showed a similar conclusion, although these investigators used synthetic hairpins as Dicer substrates. The studies proposed here will capitalize upon these important findings for generating potent siRNAs for use in animal studies. New design rules will be discussed that enable the exact prediction of the siRNA that will be generated from the Dicer substrate duplex RNAs are discussed next.

Mismatches between the siRNA antisense strand and the target tend to reduce activity to varying degrees depending on their number and location. While the rules governing the relationship between siRNA/target mismatch and RNAi activity have not been fully worked out, some generalizations can be made that probably apply to both siRNAs and simple shRNAs. Mutations near the endonucleolytic cleavage site frequently, but not always, reduce the RNAi effect. Also, mutations in the first half of the antisense strand (5' end) are very detrimental (Randall and Rice, 2001; Holen et al., 2002; Amarzguioui et al., 2003). Since endonucleolytic cleavage is 'measured' from the 5' end of the antisense siRNA strand, it is possible that mutations in the 5' end of the guide strand destabilize the antisense/mRNA target duplex in the activated RISC complex, inhibiting cleavage. Taken together, these results imply that, when designing RNAi constructs to target a specific isoform, it may be advisable to select a target site in the target isoform, such that mismatches between its corresponding siRNA and the non-targeted isoform fall in the 5' end of the duplex. If this is not possible, as when the target is inaccessible to cleavage (reviewed in Scherer and Rossi, 2003b), it is important to test for cross-reactivity.

While siRNAs constructed from 21-23-mers are sufficient for most purposes, oligomers of up to 29 nucleotides can be used without initiating the interferon effects. We have observed that siRNAs that are produced from longer double stranded RNAs in cells by the action of Dicer can be up to 100 times more potent than a 21mer provided exogenously (Kim et al., 2005). A companion manuscript by Siolas et al. (2005) had a similar conclusion, although these investigators used synthetic hairpins as Dicer substrates. The proposed studies will capitalize upon these important findings for generating potent siRNAs for use in animal studies. New design rules will be discussed that enable the exact prediction of the siRNA that will be generated from the Dicer substrate duplex RNAs.

Experiments in *Drosophila* embryo lysates indicated a need for either free 5'-OH or 5'-phosphate on synthetic siRNA strands (Elbashir et al., 2001b; Nykanen et al., 2001). Similar results were observed in HeLa extracts (Schwarz et al., 2002) or intact cells (Chiu and Rana, 2002). Asymmetric 5'-amino modification of one or the other siRNA strand showed that 5' amino modification of the antisense strand abolishes RNAi while the same modification of only the sense strand does not inhibit the RNAi effect. Also, non-phosphorylated synthetic siRNAs transfected into cells and later re-isolated cannot be kinased in vitro unless pretreated with a phosphatase (Chiu and Rana, 2002). Taken together, this suggests a strong requirement in vivo for a 5' phosphate on the antisense strand. This is consistent with the hypothesis that modifications of this nucleotide interfere with the ability of the antisense strand to serve as a guide for endonucleolytic cleavage in the activated RISC complex. On the other hand, modifications blocking the 3' end have little effect on duplex siRNA, on either strand in most cases (Amarzguioui et al., 2003).

Studies of backbone modifications on siRNA duplexes have revealed that up to six, 2'-O-methyls per siRNA strand distributed between the 5' and 3' termini, or two, 2'-O-allyl modifications at the 3' termini do not adversely affect RNAi (Amarzguioui et al., 2003). Increasing the number of modifications beyond this point, or allyl modification of the 5' termini, reduce RNAi (Amarzguioui et al., 2003; Holen et al., 2003). Conversely more than two phosphorothioate modifications are cytotoxic, while not promoting significant increases in potency (Amarzguioui et al., 2003). The advantage of backbone modifications on siRNAs may only be realized when the siRNAs are directly injected into animals, since the backbone modifications prolong the half-lives of these molecules (Layzer et al., 2004; Soutschek et al., 2004). Here, we will take advantage of the protection from serum nucleases afforded by cyclodextrin nano-particle carriers and therefore our RNAs will not be backbone modified so they can be effectively Diced in vivo.

Definition of the Sequence

RNAi can be triggered either by synthetic siRNAs delivered to cells using cationic lipids or other carriers, or via gene expression of 21 mer sense and antisense strands or short hairpin RNAs that get processed into siRNAs (reviewed in Scherer and Rossi, 2003a). An important determinant for the success of siRNA mediated knockdown is the combination of target site accessibility and the selection of the appropriate strand from the siRNA. We and others have developed algorithms to identify an appropriate combination of target site and siRNA duplex (Heale et al., 2005). Our algorithm takes into account target site secondary structure predictions and the duplex end stability of the siRNA. The latter is important in the selection of the antisense strand into RISC (Khvorova et al., 2003; Schwarz et al., 2003; Tomari et al., 2004). It has also been discovered that dsRNAs that are long enough to be cleaved the RNAse III family member Dicer can be up to 100 times more potent than 21mer siRNAs (Kim et al., 2005; Siolas et al., 2005). Thus, our preferred method for identification of target sites and siRNAs is to pick sequence motifs with our algorithm (Heale et al., 2005), identify potential target sequences and the 21mer siRNAs and test several 21mers for relative efficacy.

Figure 4:
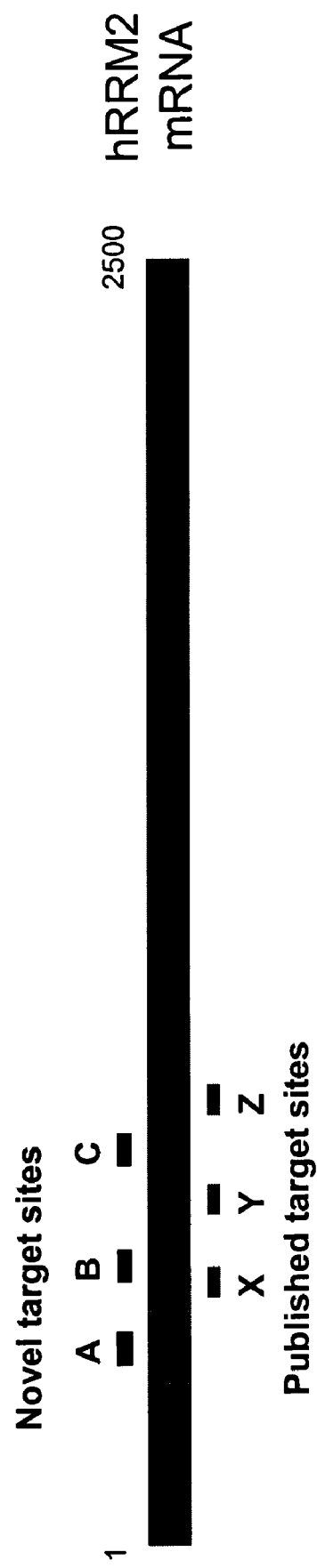
FIG. 4 illustrates the design of siRNAs targeting R2. Location of target sites within the human R2 (hRRM2) mRNA are designated A, B and C for the novel target sites according to the instant application and X, Y and Z for published target sites.
Figure 5:
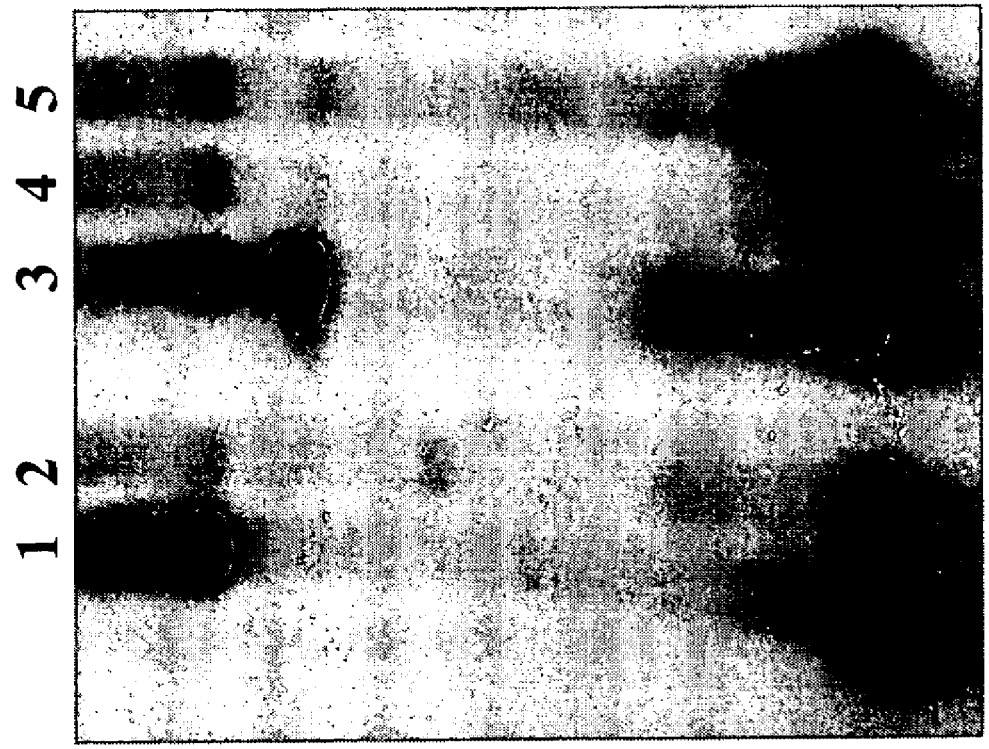
FIG. 5 shows a gel shift assay testing binding of siRNAs to the R2 target. Lanes 3, 4, and 5 show gel shift of R2 using siRNAs target to regions A, B and C, respectively, as illustrated in FIG. 4. The sequences of the siRNAs used were SEQ ID NOS: 7 and 8 (target site A), SEQ ID NOS: 9 and 10 (target site B), and SEQ ID NOS: 11 and 12 (target site C). The siRNA duplex targeted to site A showed strong binding (lane 3).

A novel computational algorithm for determination of optimal target sites was used to identify three potential target sites within the human R2 (hRRM2) gene (see FIG. 4) (Heale et al., Nucl. Acids Res. 33: e30 (2005)). siRNAs directed to these three target sequences were synthesized and tested in the cell extract prescreen assay described below. The results for the siRNAs directed against the three target sites in the cell extract binding assay are shown in FIG. 5.

Figure 6:
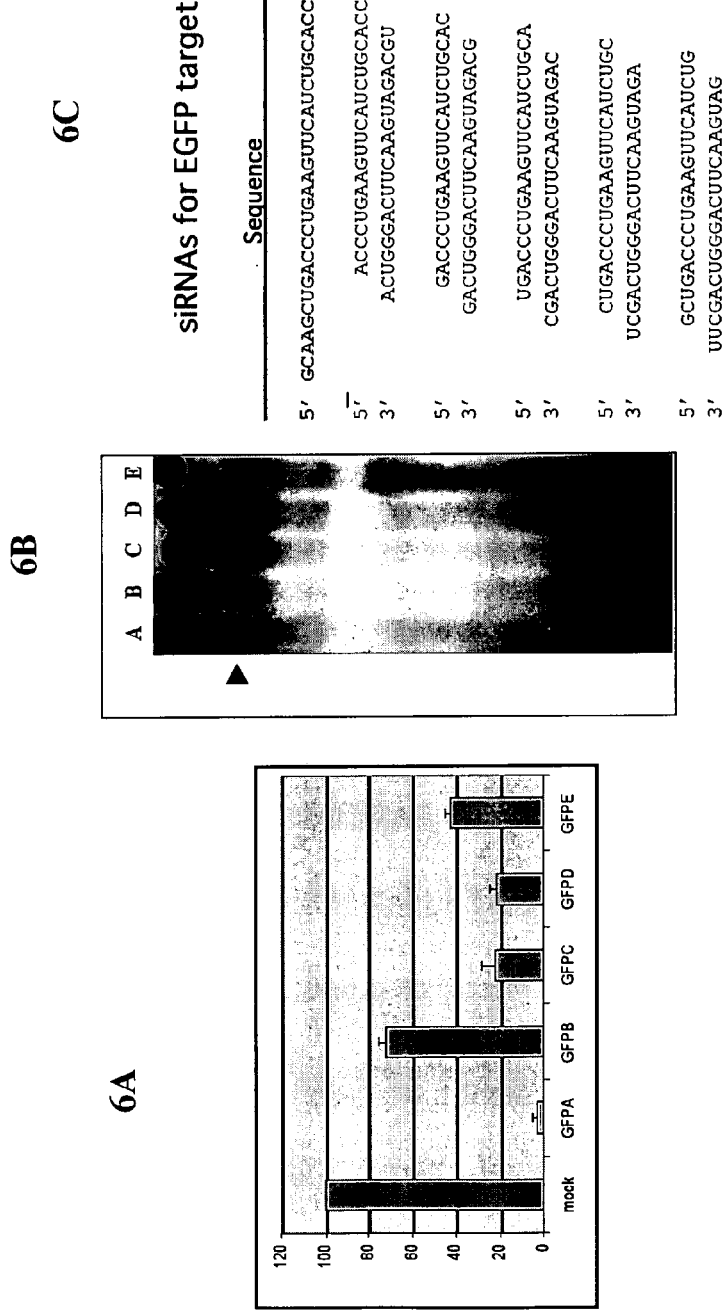
FIGS. 6A and 6B show that intracellular potency of siRNAs (FIG. 6A) correlates with their binding affinity to the target (FIG. 6B).
FIG. 6C shows various siRNAs targeting EGFP (SEQ ID NOs: 106-116 are disclosed respectively in order of appearance).

To prescreen the 21mers, we have observed that a cell extract binding assay is highly predictive of intracellular efficacy (Kim, Amarzguoi and Rossi, manuscript in preparation). Briefly, synthetic 21mers are labeled at their 5' termini with $^{32}$P and incubated in HEK 293 cytoplasmic extracts at room temperature. The siRNAs can be bound in a complex that contains the RISC component argonaute 2 (Ago2). The binding efficacy correlates strongly with intracellular potency (FIGS. 6A-6C). Once we identify the most potent 21mers, that sequence is incorporated into a 27 base duplex which is a substrate for Dicer (FIGS. 6A-6C). We have established a format for Dicing such that only the 21mer of choice is produced from the 27mer (see below). Thus, the only constraint on using the chosen 27mer is delivery. Our preferred substrate for in vivo Dicing has the following general characteristics:

Using in vitro Dicing and mass spec analyses of the Diced products we determined that Dicer recognizes the 2 base three prime overhang, and cleaves 21 bases from the 5' end of the sense strand, and 21 bases from the 2 base overhang to generate only one 21mer. By including two deoxyribonucleotides at the 3' end of the sense strand (dN), Dicer does not come in from the right hand side of this duplex, thus ensuring generation of only the 21mer of interest. FIGS. 6A-6C also presents representative results of an extract binding assay in which a series of 21mers differing by a single base, are incubated with the extracts. The binding affinity of the siRNAs is precisely correlated with the knockdown of the target. We have repeated this assay for over 20 different siRNAs, and the correlation remains.

The human and mouse R2 sequences were run through our algorithm (Heale et al., 2005). The top 5 predicted siRNAs and targets were analyzed for potential complementarity with other murine sequences, watching for extended matches at the 5' end of the antisense strand. The sequences that do not share extended 5' homology for other targets will be tested in the extract binding assay, and the top binders will be used. The 21mer sequence will be incorporated into the 27/29mer format shown above, with the extended sequences being derived from the target mRNAs. The dsRNAs will be titrated at concentrations ranging from 5 nM to 5 pM in cell culture. The dsRNAs with the lowest IC$_{50}$ value were used in subsequent in vivo experiments. Since off-targeting is a potential issue, even with the sequence pre-screening, activation of alpha and beta interferon are routinely tested using ELISA assays and murine micro array analyses (Kim et al., 2005).

Materials and Methods

FIG. 6A: RNAi assays. For co-transfection assays, HEK293 cells were seeded into 24-well plates at 60% confluency the day before transfection. Each RNA aliquot was diluted in 50 μL of Opti-MEM (Invitrogen, Carlsbad, Calif.) containing the reporter vectors and mixed with 50 μL of Opti-MEM containing 1.5 μL of Lipofectamine 2000 (Invitrogen, Carlsbad, Calif.). The mixture was incubated for 15 min at room temperature and added to cells in 500 μL of final volume of medium. To normalize for transfection efficiency, each assay included co-transfection of the target and/or duplex RNAs with a red fluorescent protein (RFP) reporter plasmid. Only experiments where transfection efficiency varied less than 10% (as assessed by RFP expression) were evaluated. Levels of EGFP expression were measured 24 hours after transfection. EGFP expression was determined by fluorescence spectrometry.

FIG. 6B: Gel shift analyses. Confluent HEK293 cells in a 10 cm plate were harvested and washed with PBS. The cell pellet was re-suspended in 0.5 μL of buffer D (20 mM HEPES, pH 7.9, 0.2 mM EDTA, 0.5 mM DTT, 50 mM KCl, 10% Glycerol, 0.2 mM PMSF) and sonicated for 15 sec. The supernatant was collected after 5 min of microcentrifugation. For each assay 10 μL of extract was incubated with 10 fmol of labeled siRNA for 30 min. The samples were mixed with native loading dye and separated on the 5% polyacrylamide gel (29:1) for 2 hours at 200V in the cold room. (c) Sequences used in lanes A-E in (b).

Example 2

Down Regulation of R2 Expression Using siRNAs

We have now designed and tested a number of siRNAs specific for the R2 sequence for their ability to down regulate expression of R2 both in vitro and in vivo. The sequences for the specific siRNAs are provided herein as SEQ ID NOs: 7-96 (shown in Tables 2-8 above).

Figure 7:
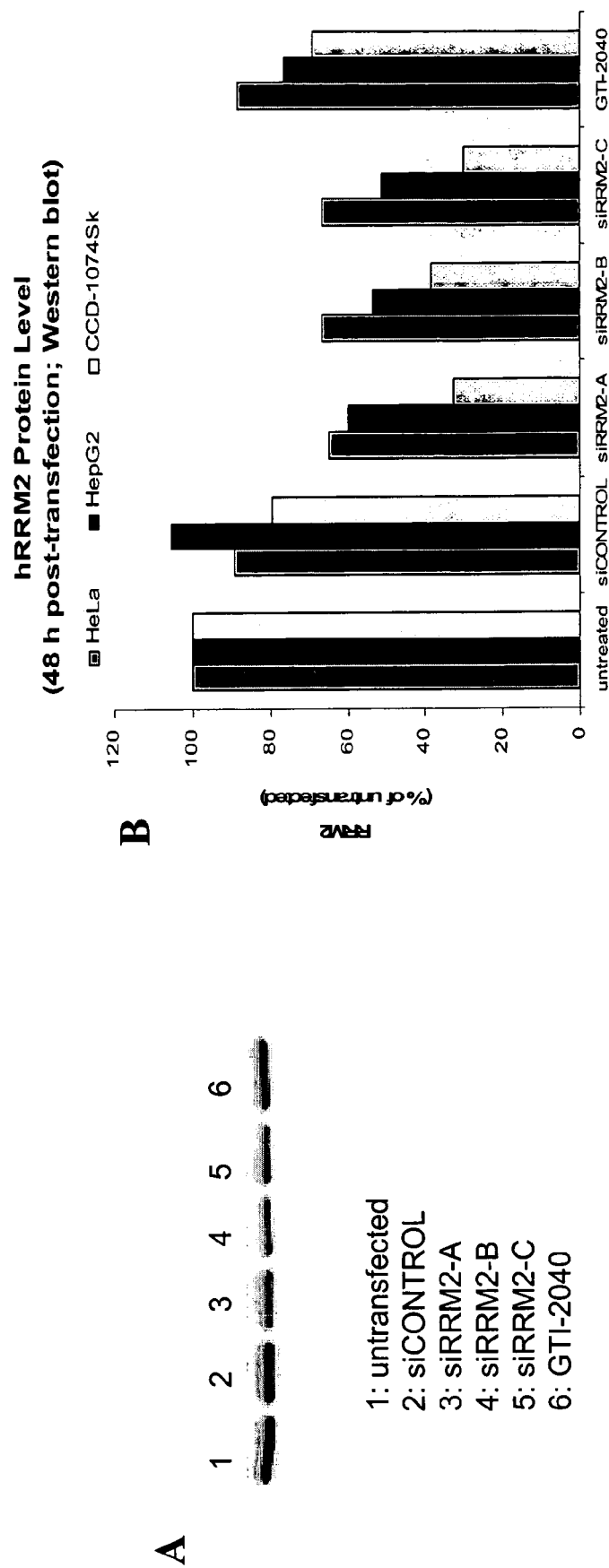
FIG. 7 shows down-regulation of R2 in various cell lines by certain siRNAs of the application.
Figure 8:
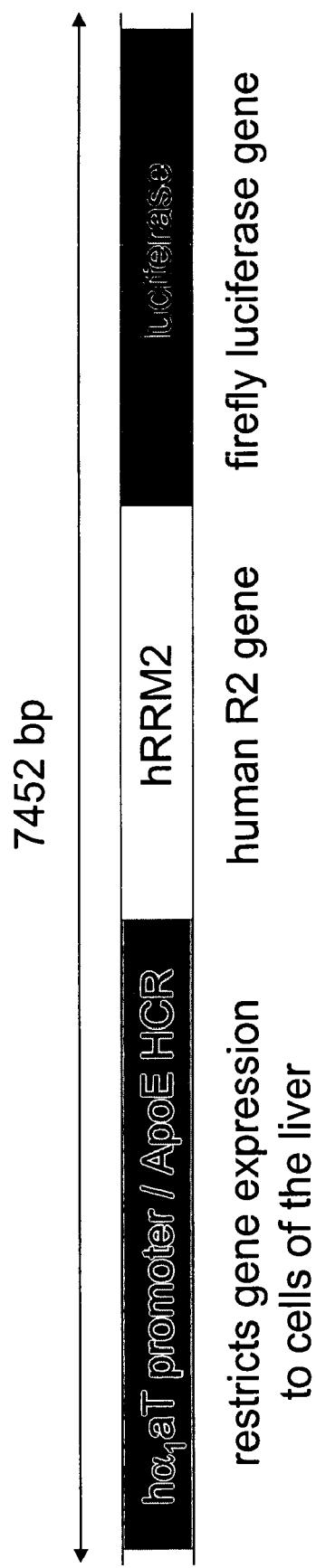
FIG. 8 shows an R2-luciferease fusion construct for screening of siRNAs against R2 ("pR2Luc plasmid"). Cells may be cotransfected with the pR2Luc plasmid and an siRNA against R2. Quantitation of luciferase level correlated with down-regulation of R2 expression.
Figure 9:
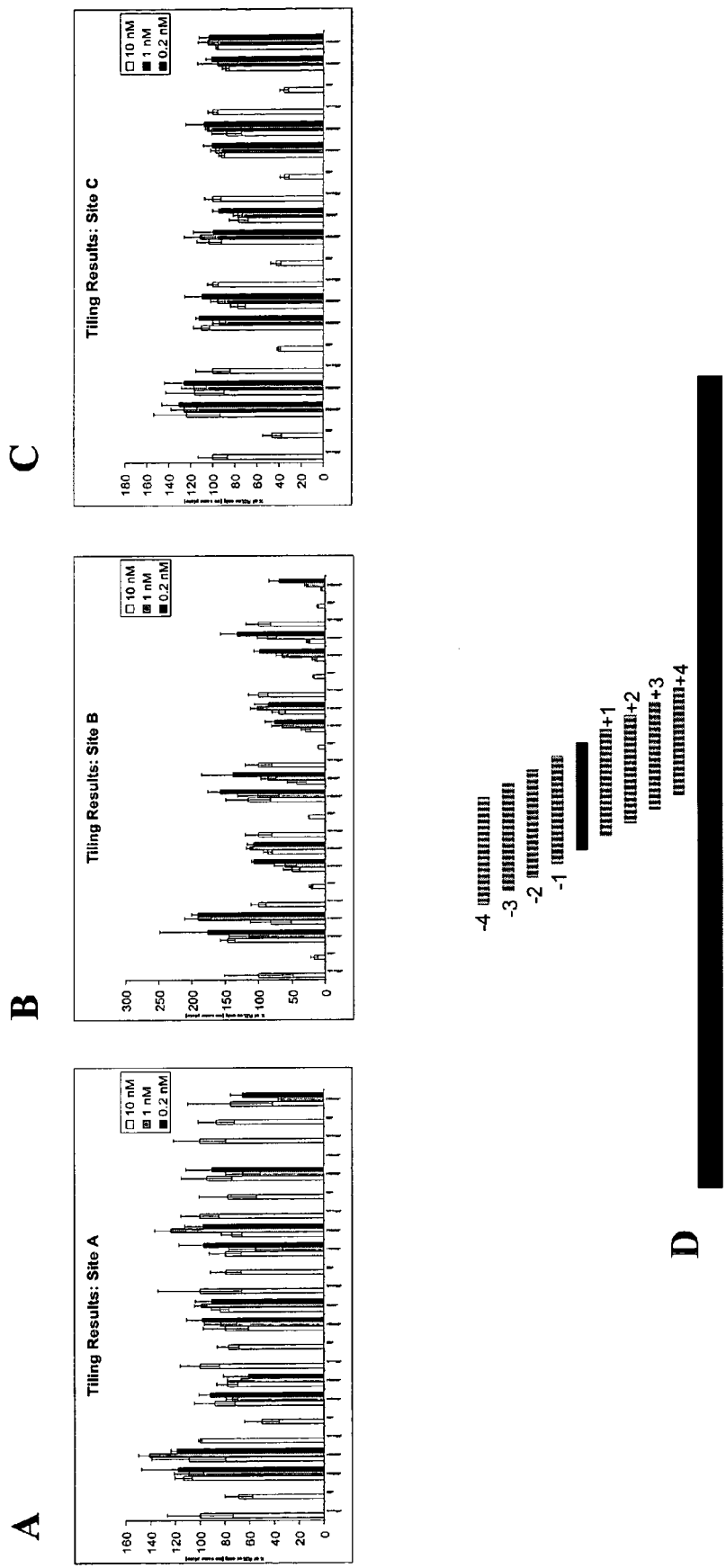
FIG. 9 illustrates the results of tiling experiments.

As shown in FIG. 7, siRNAs directed against R2 were able to down-regulate R2 expression in multiple cultured cell lines. Each of the three siRNA duplexes against R2 (siRRM2-A, siRRM2-B, and siRRM2-C shown in Table 2 as SEQ ID NOs: 7-12) achieve a reduction of the R2 protein level in each of the three cell lines examined. In contast, the GTI-2040 antisense deoxynucleotide shows minimal down-regulation.

To conduct the experiments shown in FIG. 7, HeLa (human cervical adenocarcinoma), HepG2 (hepatocellular carcinoma), and CCD-1074Sk (human fibroblasts) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siCONTROL" or "siCON1": Non-targeting control siRNA #1 (Dharmacon) shown as SEQ ID NOs: 97 and 98 in Table 10 below;

"siRRM2-A": siRNA against the "A" site of hRRM2 shown as SEQ ID NOs: 7 and 8 in Table 2 above;

"siRRM2-B": siRNA against the "B" site of hRRM2 shown as SEQ ID NOs: 9 and 10 in Table 2 above;

"siRRM2-C": siRNA against the "C" site of hRRM2 shown as SEQ ID NOs: 11 and 12 in Table 2 above; and "GTI-2040": antisense oligodeoxynucleotide against hRRM2 (Lee et al., Cancer Research 63: 2802-2811 (2003)) shown as SEQ ID NO: 99 in Table 10 below.

Table 10. Sequences of control nucleic acids used in the Examples described herein. Underlined residues represent 3' overhangs.

| Description | Sequence | Strand | SEQ ID NO |
|---|---|---|---|
| siCONTROL (or siCON1) | 5' uagcgacuaaaca caucaa<u>uu</u> 3' | Sense | SEQ ID NO: 97 |
| | 3' <u>uu</u>aucgcugauuu guguaguu 5' | Antisense | SEQ ID NO: 98 |
| GTI-2040 | 5' cuugguggagcga uuuagcc 3' | | SEQ ID NO: 99 |

The nucleic acid complexes were exposed to cells at a final nucleic concentration of 50 nM for 4 h, after which the complexes were removed by aspiration and replaced with complete medium. Two days (48 h) post-transfection, cells were lysed and the level of R2 protein was measured by Western blotting using a primary goat polyclonal anti-R2 antibody (sc-10846, Santa Cruz) at a 1:250 dilution and a secondary HRP-conjugated donkey anti-goat IgG antibody (Santa Cruz) at a 1:5000 dilution. The blot was developed using an ECL Detection Kit (GE/Amersham Biosciences) and quantified using ImageQuant TL software (GE/Amersham Biosciences).

Example 3

Tiling Experiments for Identification of R2 siRNAs at Each Target Site

Figure 10:
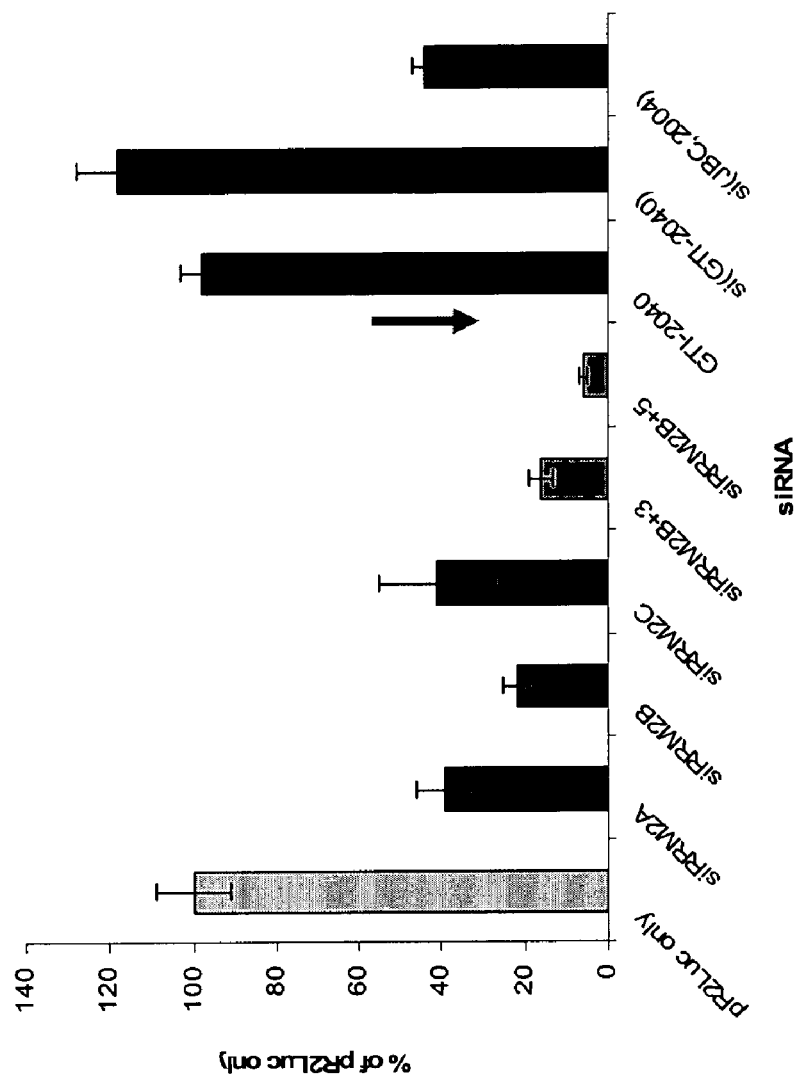
FIG. 10 shows that the use of pR2Luc in tiling experiment resulted in discovery of highly potent siRNAs. siRRM2A, siRRM2B, siRRM2C are siRNAs directed against target site A (having SEQ ID NOS: 7 and 8), target site B (having SEQ ID NOS: 9 and 10), and target site C (having SEQ ID NOS: 11 and 12), respectively; siRRM2B+3 and siRRM2B+5 are duplexes tiled from target site B that have increased potency as compared to the original site B siRNA duplex; GTI-2040 is an antisense oligodeoxynucleotide targeted against R2; si(GTI-2040) is an siRNA targeted to the same site as the GTI-2040 antisense oligodeoxynucleotide; si(JBC, 2004) is a previously published siRNA against R2.

As shown in FIG. 10, tiling experiments were used to identify siRNAs directed against R2 having increased potency. Each of the three siRNA duplexes against R2 (siRRM2A, siRRM2B, and siRRM2C shown in Table 2 above as SEQ ID NOs: 7-12) achieve a reduction of the R2-luciferase fusion protein level. Both the siRRM2B+3 and siRRM2B+5 duplexes show superior down-regulation to each of the three original duplexes, with siRRM2B+5 giving the most potent down-regulation. In contast, both the GTI-2040 antisense deoxynucleotide and an siRNA having the same target ("si(GTI-2040)") fail to exhibit any down-regulation. Finally, the down-regulation achieved with a previously published siRNA against RRM2 ("si(JBC, 2004)") is shown for comparison.

To conduct the experiments shown in FIG. 10, HepG2 (hepatocellular carcinoma) cells were received from the American Type Culture Collection. Cells were plated in 24-well tissue-culture plates (50,000 cells per well) 24 h prior to transfection. For transfection, complexes were prepared in serum-free medium (OptiMEM, Invitrogen) using Lipofectin (Invitrogen), the pR2Luc plasmid (1 μg/well), and each of the following nucleic acids according to the manufacturer's recommendations:

"siRRM2A": siRNA against the "A" site of hRRM2 shown as SEQ ID NOs: 7 and 8 in Table 2 above;
"siRRM2B": siRNA against the "B" site of hRRM2 shown as SEQ ID NOs: 9 and 10 in Table 2 above;
"siRRM2C": siRNA against the "C" site of hRRM2 shown as SEQ ID NOs: 11 and 12 in Table 2 above;
"siRRM2B+3": siRNA three nucleotides down-stream of the original "B" site of hRRM2 shown as SEQ ID NOs: 59 and 60 in Table 5 above;
"siRRM2B+5": siRNA five nucleotides down-stream of the original "B" site of hRRM2 shown as SEQ ID NOs: 63 and 64 in Table 5 above;
"GTI-2040": antisense oligodeoxynucleotide against hRRM2 shown as SEQ ID NO: 99 in Table 10 above;
"si(GTI-2040)": siRNA duplex having the same target site as the antisense oligodeoxynucleotide against hRRM2 (shown as SEQ ID NOs: 100 and 101 in Table 11 below); and
"si(JBC, 2004)": siRNA duplex against hRRM2 published previously (J. Biol. Chem. 279(26):27030-27038, 2004) (shown as SEQ ID NOs: 102 and 103 in Table 11 below).

Table 11. Sequences of si(GTI-2040) and si(JBC, 2004) used in the Examples described herein. Underlined residues represent 3' overhangs.

| Description | Sequence | Strand | SEQ ID NO |
|---|---|---|---|
| si(GTI-2040) | 5' cuugguggag cgauuuagcaa 3' | Sense | SEQ ID NO: 100 |
| | 3' uugaaccacc ucgcuaaaucgg 5' | Antisense | SEQ ID NO: 101 |
| si(JBC 2004) | 5' gaggcuaccu auggugaacgu 3' | Sense | SEQ ID NO: 102 |
| | 3' uucuccgaug gauaccacuug 5' | Antisense | SEQ ID NO: 103 |

These nucleic acid complexes were exposed to cells at a final nucleic concentration of 10 nM for 4 h, after which the complexes were removed by aspiration and replaced with complete medium. Two days (48 h) post-transfection, cells were lysed and the level of R2-luciferase fusion protein was measured using a luciferase assay (Luciferase Assay System, Promega) according to the manufacturer's instructions.

Example 4

Additional Tiling Experiments for Identification of R2 siRNAs at Target Site B

Figure 11:
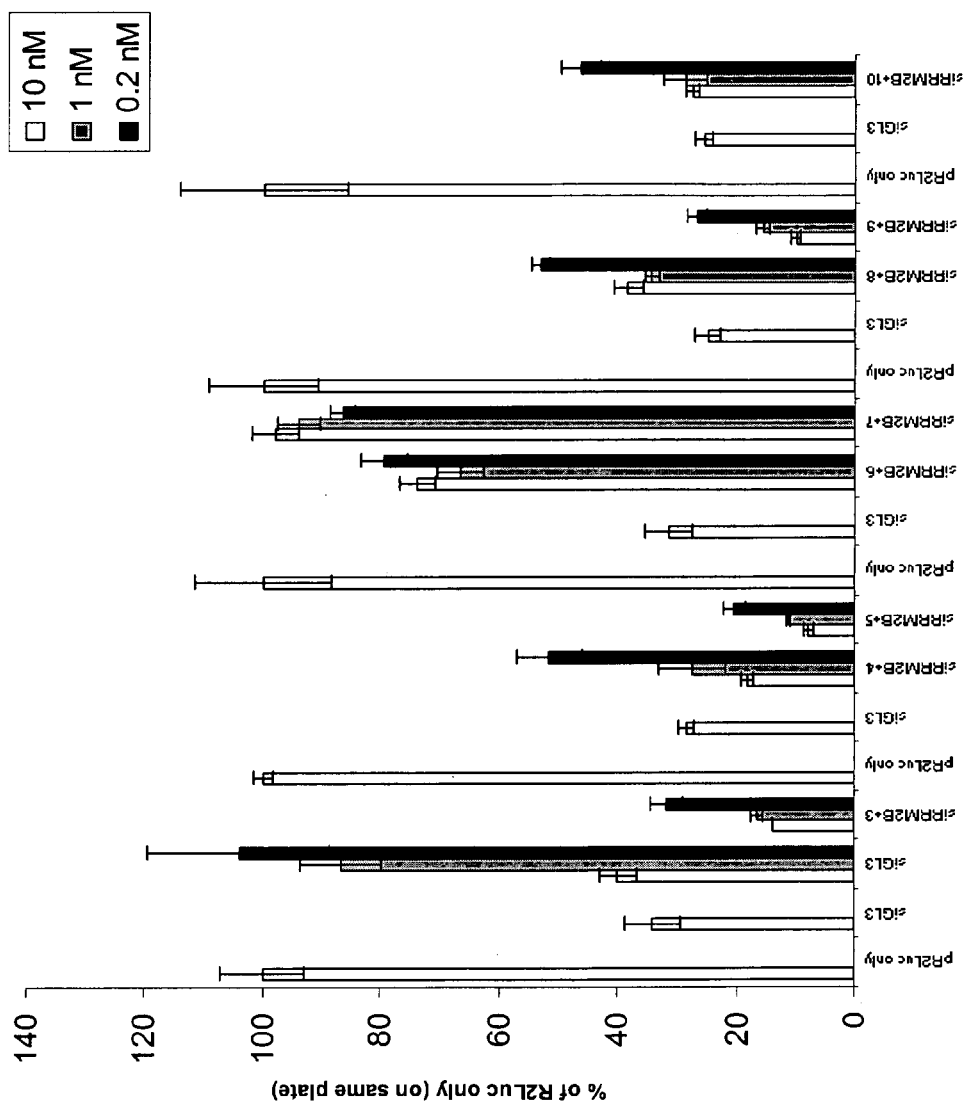
FIG. 11 shows the result of additional tiling experiments using duplexes around target site B (tiling B+3 to B+10). The B+5 duplex remained the most potent duplex examined and the B+9 duplex emerged as the second-most potent duplex.

FIG. 11 shows the results of additional tiling experiments that were conducted to identify siRNA directed to R2 having increased potency. Similar to the results shown in FIG. 10, the siRRM2B+5 gives the most potent down-regulation. The siRRM2B+9 and siRRM2B+3 duplexes also give strong down-regulation, but not as strong as siRRM2B+5.

To conduct the experiments shown in FIG. 11, HepG2 (hepatocellular carcinoma) cells were received from the American Type Culture Collection. Cells were plated in 24-well tissue-culture plates (50,000 cells per well) 24 h prior to transfection. For transfection, complexes were prepared in serum-free medium (OptiMEM, Invitrogen) using Lipofectin (Invitrogen), the pR2Luc plasmid (1 μg/well), and each of the following nucleic acids according to the manufacturer's recommendations:

"siGL3": siRNA targeting luciferase sold by Dharmacon ("Luciferase GL3 Duplex");
"siRRM2B+3": siRNA three nucleotides down-stream of the original "B" site of hRRM2 shown as SEQ ID NOs: 59 and 60 in Table 5 above;
"siRRM2B+4": siRNA four nucleotides down-stream of the original "B" site of hRRM2 shown as SEQ ID NOs: 61 and 62 in Table 5 above;
"siRRM2B+5": siRNA five nucleotides down-stream of the original "B" site of hRRM2 shown as SEQ ID NOs: 63 and 64 in Table 5 above;
"siRRM2B+6": siRNA six nucleotides down-stream of the original "B" site of hRRM2 shown as SEQ ID NOs: 87 and 88 in Table 8 above;
"siRRM2B+7": siRNA seven nucleotides down-stream of the original "B" site of hRRM2 shown as SEQ ID NOs: 89 and 90 in Table 8 above;
"siRRM2B+8": siRNA eight nucleotides down-stream of the original "B" site of hRRM2 shown as SEQ ID NOs: 91 and 92 in Table 8 above;
"siRRM2B+9": siRNA nine nucleotides down-stream of the original "B" site of hRRM2 shown as SEQ ID NOs: 93 and 94 in Table 8 above; and "siRRM2B+10": siRNA ten nucleotides down-stream of the original "B" site of hRRM2 shown as SEQ ID NOs: 95 and 96 in Table 8 above.

These complexes were exposed to cells at a final siRNA concentration of 10 nM, 1 nM, or 0.2 nM for 4 h, after which the complexes were removed by aspiration and replaced with complete medium. Two days (48 h) post-transfection, cells were lysed and the level of R2-luciferase fusion protein was measured using a luciferase assay (Luciferase Assay System, Promega) according to the manufacturer's instructions.

Example 5

Assays of 21mer and 27mer siRNA Activity

Figure 12:
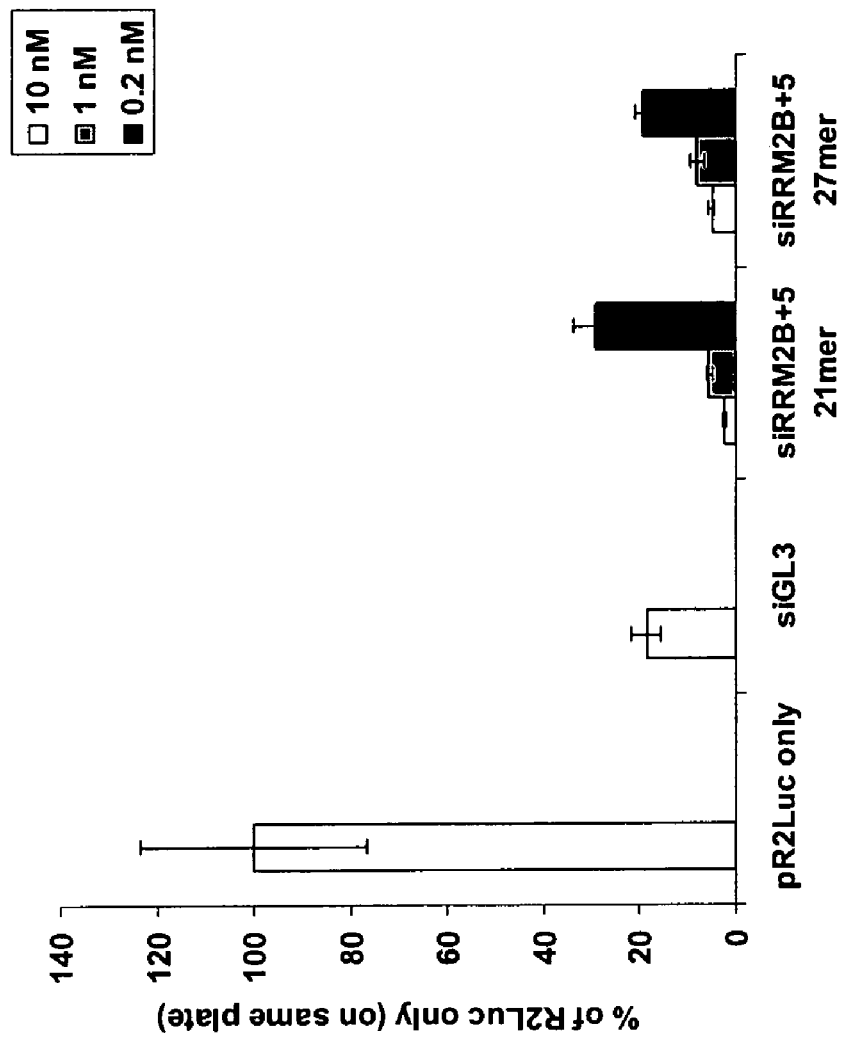
FIG. 12 shows dose-dependent down-regulation of an R2-luciferase fusion protein by 21mer and 27mer RNAs.

As shown in FIG. 12, dose-dependence co-transfection studies with RNA duplexes (either 21mer or 27mer) at the B+5 target site were conducted to identify siRNAs directed to R2 having increased potency. Both the siRRM2B+5 21mer and 27mer give potent down-regulation of co-lipofected R2Luc. At the highest concentrations examined (10 nM and 1 nM), the 21mer shows slightly greater potency than the 27mer, while at the lowest concentration examined (0.2 nM) the 27mer shows slightly greater potency.

To conduct the experiments shown in FIG. 12, HepG2 (hepatocellular carcinoma) cells were received from the American Type Culture Collection. Cells were plated in 24-well tissue-culture plates (50,000 cells per well) 24 h prior to transfection. For transfection, complexes were prepared in serum-free medium (OptiMEM, Invitrogen) using Lipofectin (Invitrogen), the pR2Luc plasmid (1 µg/well), and each of the following nucleic acids according to the manufacturer's recommendations:

"siRRM2B+5 21mer": siRNA five nucleotides down-stream of the original "B" site of hRRM2 shown as SEQ ID NOs: 63 and 64 in Table 5 above; and "siRRM2B+5 27mer": 27mer RNA duplex having the same target site as siRRM2B+5 and expected to have a Dicer cleavage product identical to the siRRM2B+5 21mer (shown as SEQ ID NOs: 85 and 86 in Table 7 above).

These complexes were exposed to cells at a final siRNA concentration of 10 nM, 1 nM, or 0.2 nM for 4 h, after which the complexes were removed by aspiration and replaced with complete medium. Two days (48 h) post-transfection, cells were lysed and the level of R2-luciferase fusion protein was measured using a luciferase assay (Luciferase Assay System, Promega) according to the manufacturer's instructions.

Example 6

Down Regulation of Endogenous R2 Expression Using siRNAs

Figure 13:
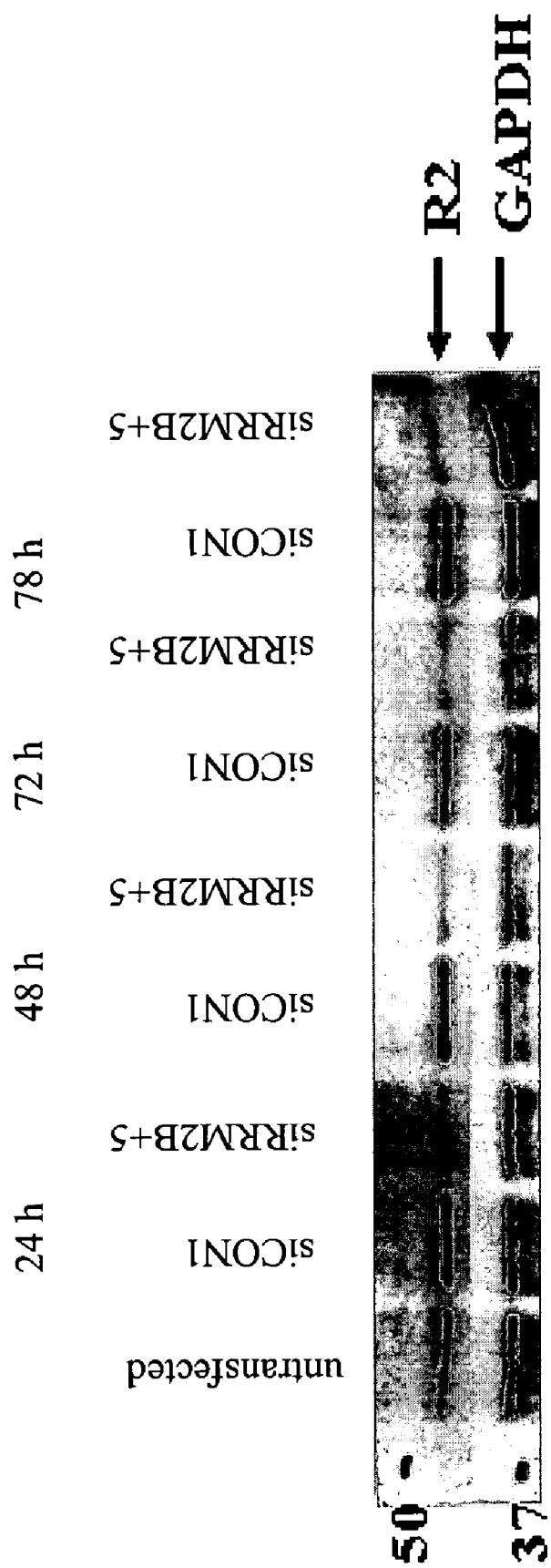
FIG. 13 shows that siRNA-induced down-regulation of R2-luciferase fusion correlates to the down-regulation of endogenous R2. The siRRM2B+5 duplex was identified as being highly potent in co-transfection studies with pR2Luc. As illustrated in the figure, transfection of the siRRM2B+5 duplex alone in Hep3B cells resulted in sequence-specific knowckdown of endogenous R2 at 1 day, 2 days, and 3 days post-transfection. Cells were transfected with 20 nM of siRRM2B+5 or siCON1 (Dharamacon's non-targeted control duplex #1).

As shown in FIG. 13, the siRNA-induced down-regulation of the R2-luciferase fusion correlates to knockdown of endogenous R2 expression. At all four of the timepoints examined, the siRRM2B+5 induces strong down-regulation of the endogenous R2 protein that was not seen with the non-targeting control (siCON1) siRNA. This confirms that the siRRM2B+5 duplex, first examined in the "tiling experiments" with the R2-luciferase fusion protein, is indeed a potent down-regulator of endogenous R2 in hepatocellular carcinoma cells.

To conduct the experiments shown in FIG. 13, Hep3B (hepatocellular carcinoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siCONTROL": Non-targeting control siRNA #1 (Dharmacon) (shown as SEQ ID NOs: 97 and 98 in Table 10 above); and "siRRM2B+5": siRNA five nucleotides down-stream of the original "B" site of hRRM2 (shown as SEQ ID NOs: 63 and 64 in Table 5 above).

These complexes were exposed to cells at a final siRNA concentration of 50 nM for 4 h, after which the complexes were removed by aspiration and replaced with complete medium. At one day (24 h), two days (48 h), three days (72 h), or 3.25 days (78 h) post-transfection, cells were lysed and the level of R2 protein was measured by Western blotting. The Western blot utilized a primary goat polyclonal anti-R2 antibody (sc-10846, Santa Cruz) at a 1:250 dilution and a secondary HRP-conjugated donkey anti-goat IgG (Santa Cruz) at a 1:5000 dilution. The Western blot was developed using an ECL Detection Kit (GE/Amersham Biosciences). The membrane was subsequently stripped (REstore Stripping Buffer, Pirece) and blotted for GAPDH as a loading control. Quantification of Western blots was performed using ImageQuant TL software (GE/Amersham Biosciences).

Example 7 siRNA Against R2 Induces Apoptosis in HepG2 Cells

Figure 14:
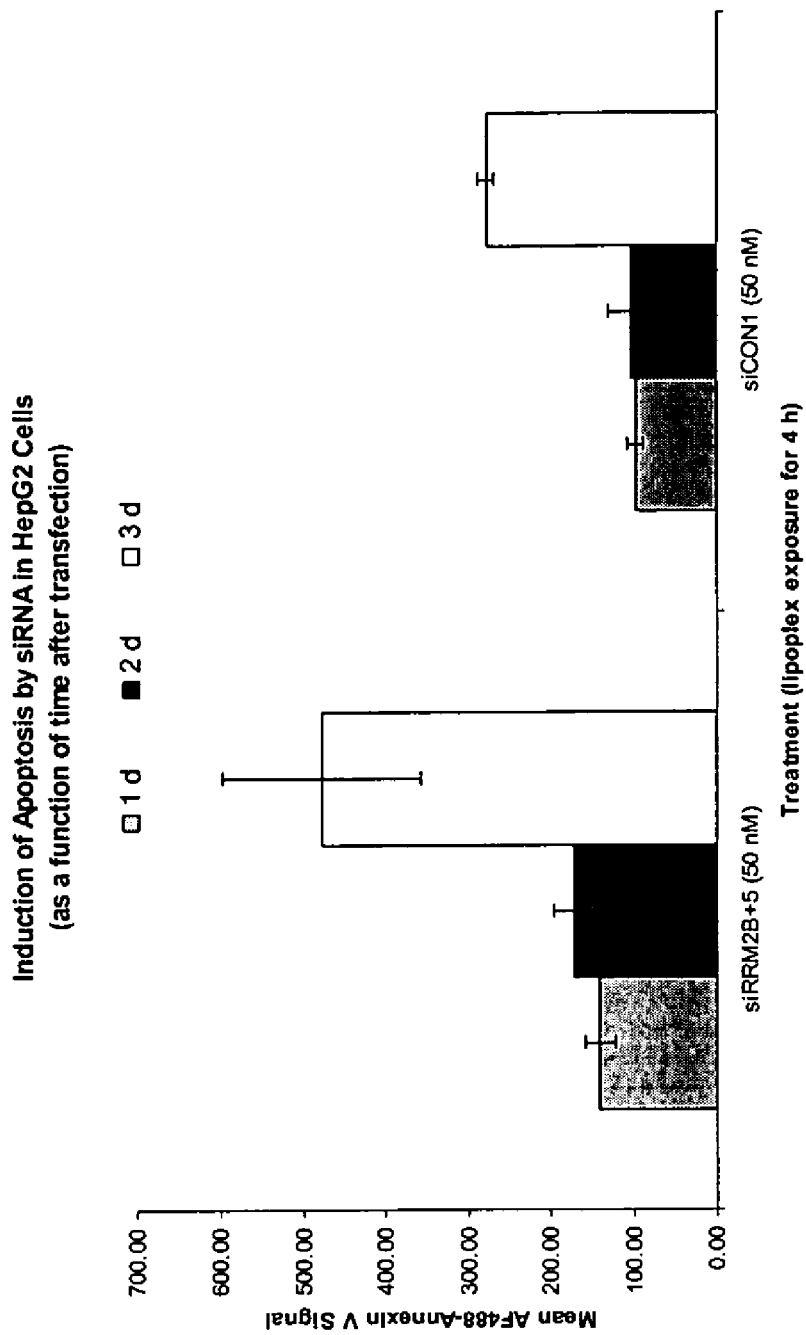
FIG. 14 shows that an siRNA against R2 induces apoptosis of lipofected cells. Cultured human HCC cells (HepG2) were transfected with siRNA against R2 (siRRM2B+5) or a non-targeting control siRNA (siCON1) and then analyzed for apoptosis at 1 day, 2 days or 3 days post-transfection.

As shown in FIG. 14, siRNA against R2 induces apoptosis in HepG2 cells. At all three timepoints examined, but most significantly at 3 days post-transfection, HepG2 cells transfected with siRRM2B+5 exhibited a higher degree of fluorescence (indicating a higher extent of apoptosis) than those transfected with siCON1.

To conduct the experiments shown in FIG. 14, HepG2 (hepatocellular carcinoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siCONTROL": Non-targeting control siRNA #1 (Dharmacon) (shown as SEQ ID NOs: 97 and 98 in Table 10 above); and "siRRM2B+5": siRNA five nucleotides down-stream of the original "B" site of hRRM2 (shown as SEQ ID NOs: 63 and 64 in Table 5 above).

These complexes were exposed to cells at a final siRNA concentration of 50 nM for 4 h, after which the complexes were removed by aspiration and replaced with complete medium. At one day (24 h), two days (48 h), or three days (72 h) post-transfection, cells were analyzed for apoptosis using the Vybrant Apoptosis Assay #2 (Invitrogen) and flow cytometry. Data is reported as population mean fluorescence after exposure to AlexaFluor488-labeled Annexin V.

Example 8 siRNA Against R2 Enhances Drug-Induced Apoptosis of HCC Cells

Figure 15:
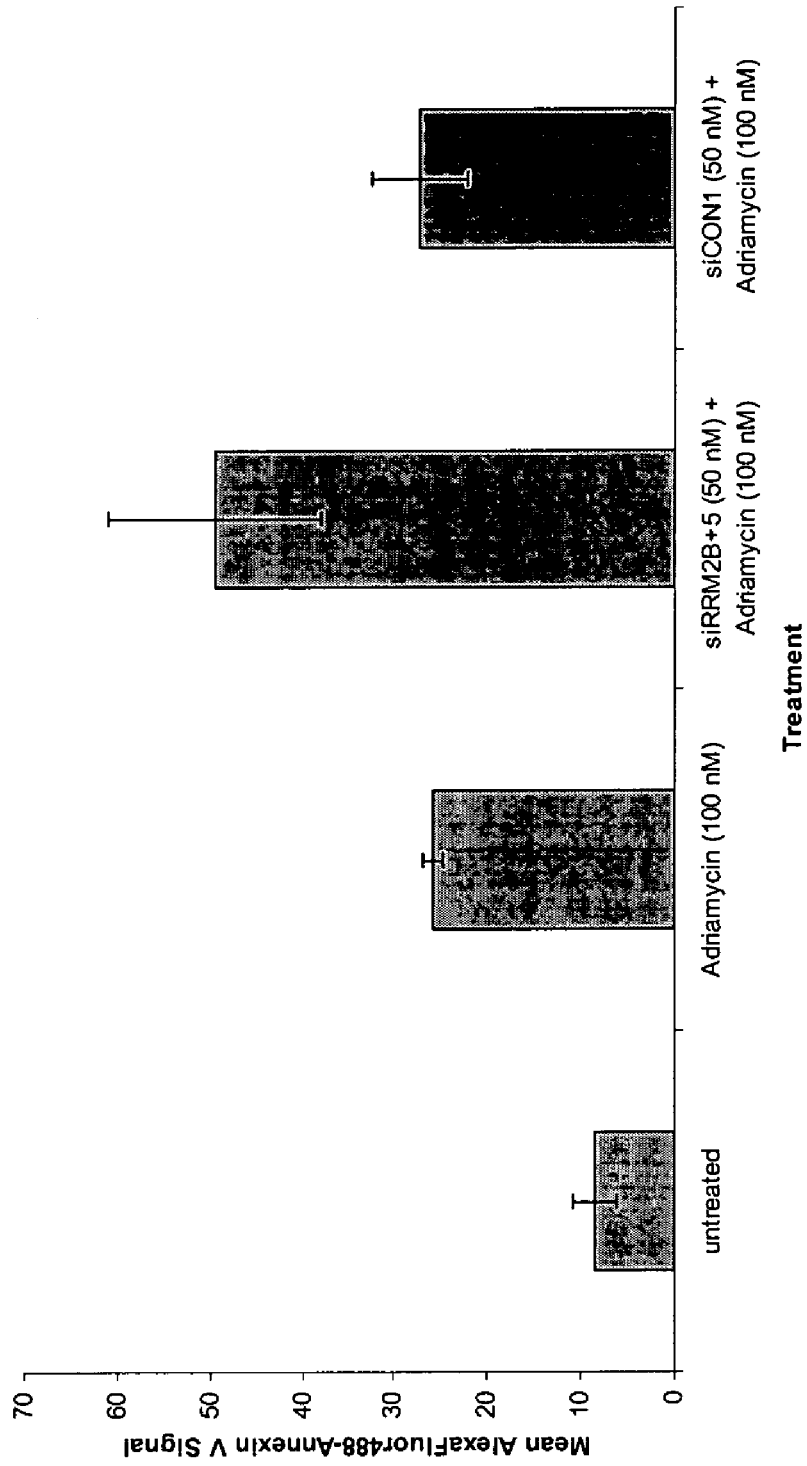
FIG. 15 shows that an siRNA against R2 enhances drug-induced apoptosis of human HCC cells. Cultured human HCC cells (HepG2) were transfected with siRNA against R2 (siRRM2B+5) or a non-targeting control siRNA (siCON1) followed by treatment with adriamycin (100 nM) for 3 days. The level of apoptosis was then determined.

As shown in FIG. 15, siRNA against R2 enhances drug-induced apoptosis of HCC. HepG2 cells that had been lipofected with siRRM2B+5 prior to adriamycin exposure showed a significantly higher degree of apoptosis than those that had received no siRNA or had been lipofected with the non-targeting control (siCON1) siRNA.

To conduct the experiments shown in FIG. 15, HepG2 (hepatocellular carcinoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siCONTROL": Non-targeting control siRNA #1 (Dharmacon) (shown as SEQ ID NOs: 97 and 98 in Table 10 above); and "siRRM2B+5": siRNA five nucleotides down-stream of the original "B" site of hRRM2 (shown as SEQ ID NOs: 63 and 64 in Table 5 above).

These complexes were exposed to cells at a final siRNA concentration of 50 nM for 4 h, after which they were removed by aspiration and cells (lipoplex-treated as well as previously untreated cells) were incubated with adriamycin (100 nM) for 3 days. Cells were then analyzed for apoptosis using the Vybrant Apoptosis Assay #2 (Invitrogen) and flow cytometry. Data is reported as population mean fluorescence after exposure to AlexaFluor488-labeled Annexin V.

Example 9 siRNA Against R2 Reduces Expression of R2-Luciferase Fusion Protein In Vivo

Figure 16:
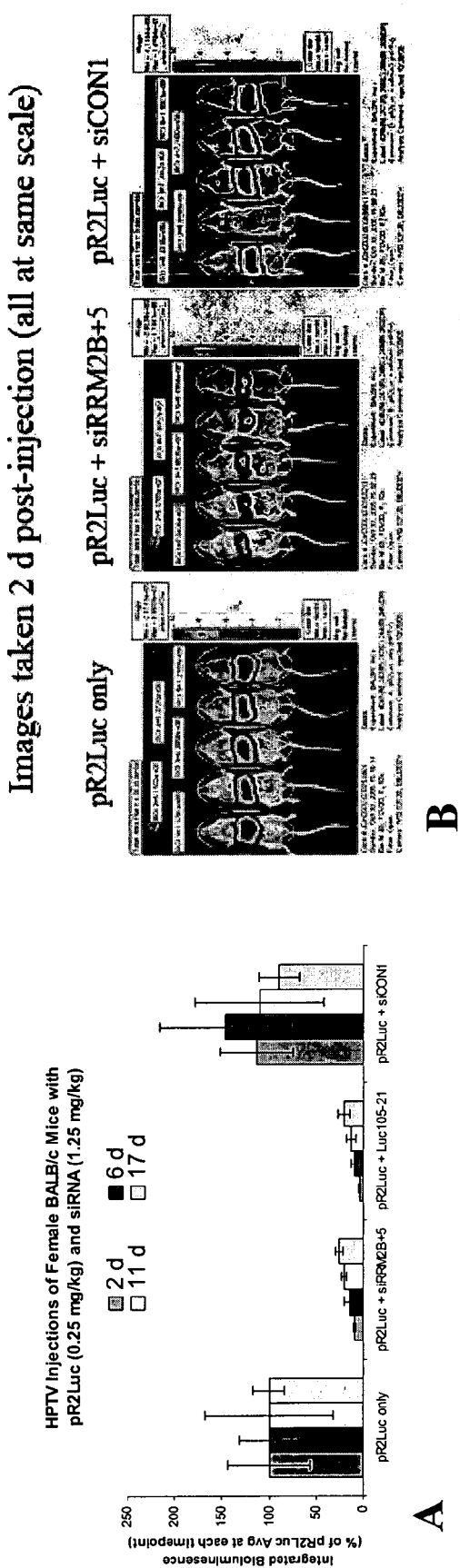
FIG. 16 shows that an siRNA against R2 reduces R2 expression in vivo. A plasmid encoding an R2-luciferase fusion gene (pR2Luc) was co-injected with siRNA against R2 (siRRM2B+5) or a non-targeting control siRNA (siCON1) in BALB/c mice. Fusion gene expression was followed by whole-animal bioluminescence imaging.

As shown in FIG. 16, siRNA against R2 reduces expression of R2-luciferase fusion protein in vivo. At all timepoints, mice that received the siRRM2B+5 duplex (shown as SEQ ID NOs: 63 and 64 in Table 5 above) showed sharply reduced luminescence compared to mice that received the pR2Luc plasmid alone or the plasmid with the siCON1 duplex.

To conduct the experiments shown in FIG. 16, female BALB/c mice (aged ~6 weeks, Jackson Labs, groups of n=5) received a single high-pressure (10% v/w) tail vein injection of the pR2Luc plasmid (0.25 mg/kg) alone or in combination with siRNA (1.25 mg/kg) against R2 (siRRM2B+5), luciferase (Luc105-21), or a non-targeting control (siCON1) siRNA. At various timepoints (2, 6, 11, and 17 days) post-injection, mice were anesthetized (isoflurane gas), injected with D-luciferin (Xenogen; 150 mg/kg in PBS intraperitoneally), and imaged 10 min later to determine whole animal bioluminescence (using IVIS 100 Imaging System, Xenogen). Data in the bar graph is provided as whole animal bioluminescence as a percentage of the mean value for mice that received the pR2Luc plasmid only at each timepoint. In addition, representative images of the mice taken at t=2 days post-injection are shown (FIG. 16).

Example 10 siRNA Against R2 Reduces Growth Potential of Cultured HCC Cells

Figure 17:
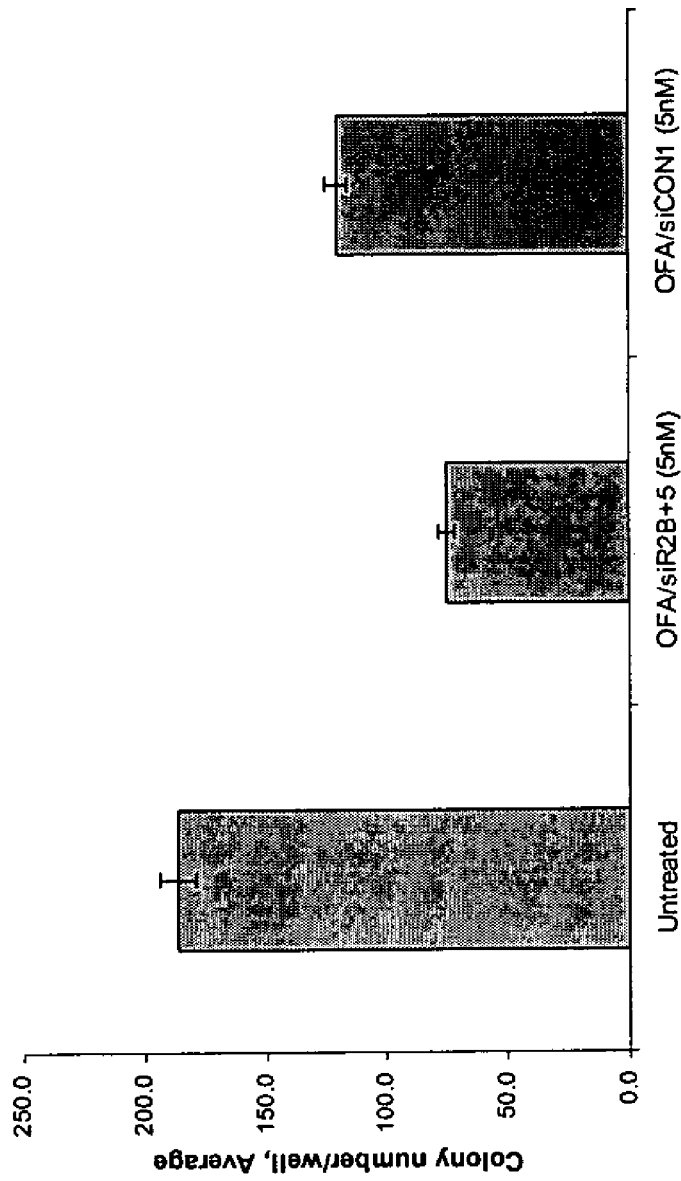
FIG. 17 shows that an siRNA against R2 (siR2B+5) reduces growth potential of cultured human HCC cells (Hep3B cells). Human hepatocellular carcinoma (HCC) cells (Hep3B) are dilutely plated and then transfected with non-targeting control siRNA (siCON1) or siRNA against R2 (siR2B+5) (5 nM). Five days post-transfection, cells are fixed, stained (methylene blue), and colonies (~50 or more cells) are counted. As illustrated, siRNA against R2 (siR2B+5) significantly reduces the colony formation potential of Hep3B cells compared to the non-targeting control siRNA (siCON1). Columns represent the average of n=3 replicate wells; error bars represent standard deviation.

As shown in FIG. 17, optimized siRNA against R2 (siR2B+5) reduces growth potential of cultured human HCC cells (Hep3B cells). Lipofection of Hep3B cells with optimized siRNA against R2 (siR2B+5) significantly reduces colony formation potential compared to similar treatment with a non-targeting control siRNA (siCON1). This suggests that down-regulation of R2 (resulting solely from lipofection with anti-R2 siRNA) in these cells reduces their growth potential.

To conduct the experiments hwon in FIG. 17, Hep3B (human hepatocellular carcinoma) cells were received from the American Type Culture Collection. Cells were plated dilutely in six-well tissue-culture plates (1,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siR2B+5": optimized siRNA against hRRM2 (shown as SEQ ID NOs: 63 and 64 in Table 5 above); and "siCON1": Non-targeting control siRNA #1 (Dharmacon) (shown as SEQ ID NOs: 97 and 98 in Table 10 above).

These complexes were exposed to cells at a final siRNA concentration of 5 nM for 4 h, after which the complexes were removed by aspiration and replaced with complete medium. Five days (120 h) post-transfection, cells were fixed with ethanol (10 min) and stained with methylene blue (in water). Colonies (having ~50 or more cells) were counted manually. Triplicate wells (n=3) were used for each treatment; columns represent averages and error bars represent standard deviation (FIG. 17).

Example 11

Potency of siRNA Correlates with Ability to Reduce Growth Potential

Figure 18:
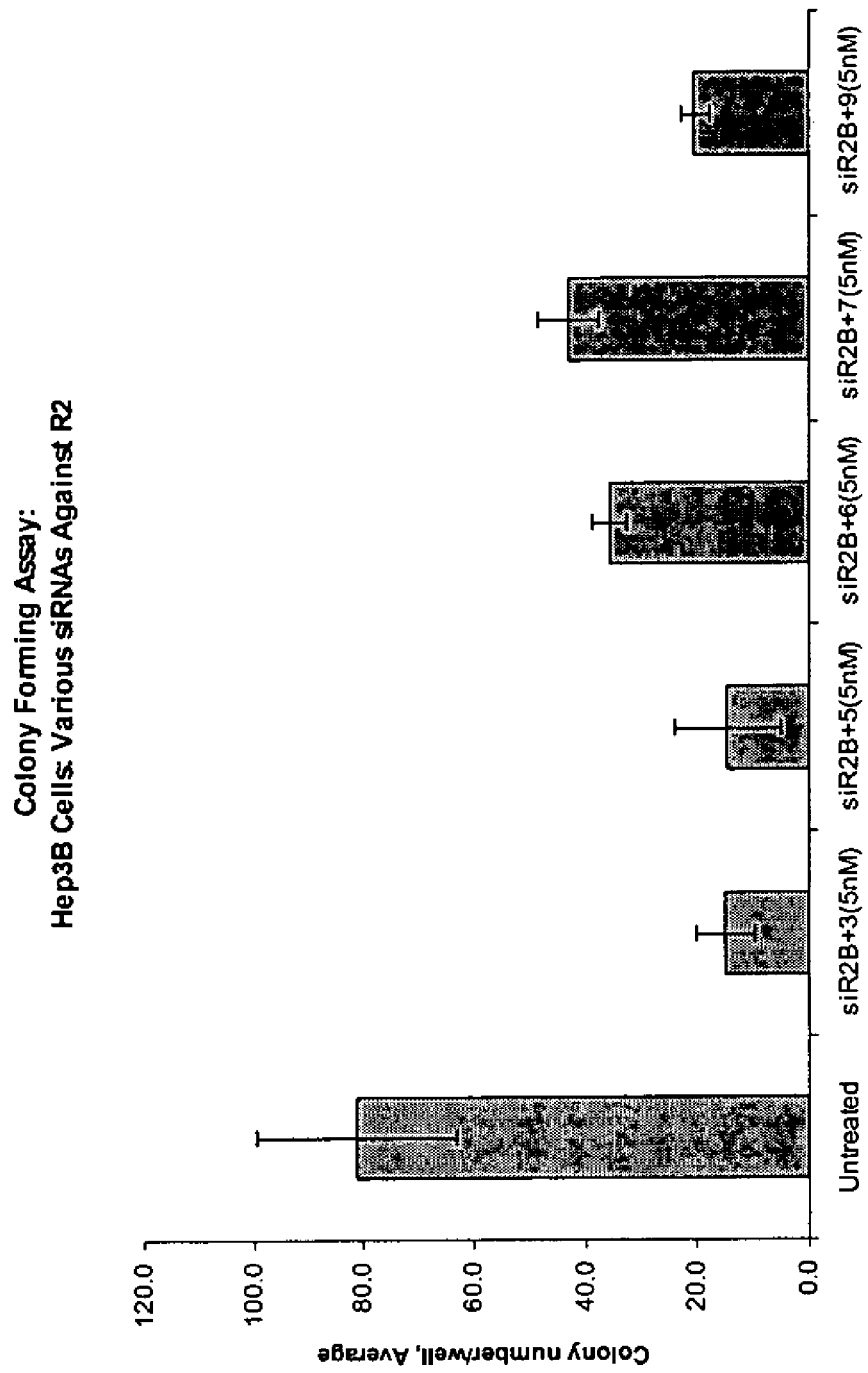
FIG. 18 shows that the potency of siRNA against R2 correlates with the ability to reduce growth potential of cultured human HCC cells (Hep3B cells). Human hepatocellular carcinoma (HCC) cells (Hep3B) are dilutely plated and then transfected with one of five siRNAs (siR2B+3, siR2B+5, siR2B+6, siR2B+7, siR2B+9) (5 nM) previously shown to have variable potency against R2 (see e.g., FIG. 11). Five days post-transfection, cells are fixed, stained (methylene blue), and colonies (~50 or more cells) are counted. As illustrated, the ability of an siRNA to reduce colony formation (this figure) strongly correlates with its potency for down-regulation of R2 (see FIG. 11), e.g., siR2B+3, siR2B+5, siR2B+9>>siR2B+6, siR2B+7. Columns represent the average of n=3 replicate wells; error bars represent standard deviation.

As shown in FIG. 18, the potency of siRNAs against R2 correlates with the ability of the siRNA to reduce growth potential of cultured human HCC cells. Lipofection of Hep3B cells with any of three siRNAs that have been shown to be potent down-regulators of R2 (siR2B+3, siR2B+5, and siR2B+9) significantly reduces colony formation potential compared to similar treatment with either of two siRNAs that have been shown to be poor down-regulators of R2 (siR2B+6 and siR2B+7). This result, as for the result in FIG. 17, suggests that down-regulation of R2 (resulting solely from lipofection with anti-R2 siRNA) in Hep3B cells reduces their growth potential.

To conduct the experiments shown in FIG. 18, Hep3B (human hepatocellular carcinoma) cells were received from the American Type Culture Collection. Cells were plated dilutely in six-well tissue-culture plates (500 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siR2B+3": relatively potent siRNA against hRRM2 (shown as SEQ ID NOs: 59 and 60 in Table 5 above);

"siR2B+5": relatively potent siRNA against hRRM2 (shown as SEQ ID NOs: 63 and 64 in Table 5 above);

"siR2B+6": less potent siRNA against hRRM2 (shown as SEQ ID NOs: 87 and 88 in Table 8 above);

"siR2B+7": less potent siRNA against hRRM2 (shown as SEQ ID NOs: 89 and 90 in Table 8 above); and "siR2B+9": relatively potent siRNA against hRRM2 (shown as SEQ ID NOs: 93 and 94 in Table 5 above).

These complexes were exposed to cells at a final siRNA concentration of 5 nM for 4 h, after which the complexes were removed by aspiration and replaced with complete medium. Five days (120 h) post-transfection, cells were fixed with ethanol (10 min) and stained with methylene blue (in water).

Colonies (having 50 or more cells) were counted manually. Triplicate wells (n=3) were used for each treatment; columns represent averages and error bars represent standard deviation (FIG. 18). For purposes of comparison, the results of a co-transfection study (to evaluate the relative potency of these siRNA duplexes against R2) are shown in FIG. 11.

Example 12

Reduction of Growth Potential by R2 siRNAs is Enhanced by 5-FU

Figure 19:
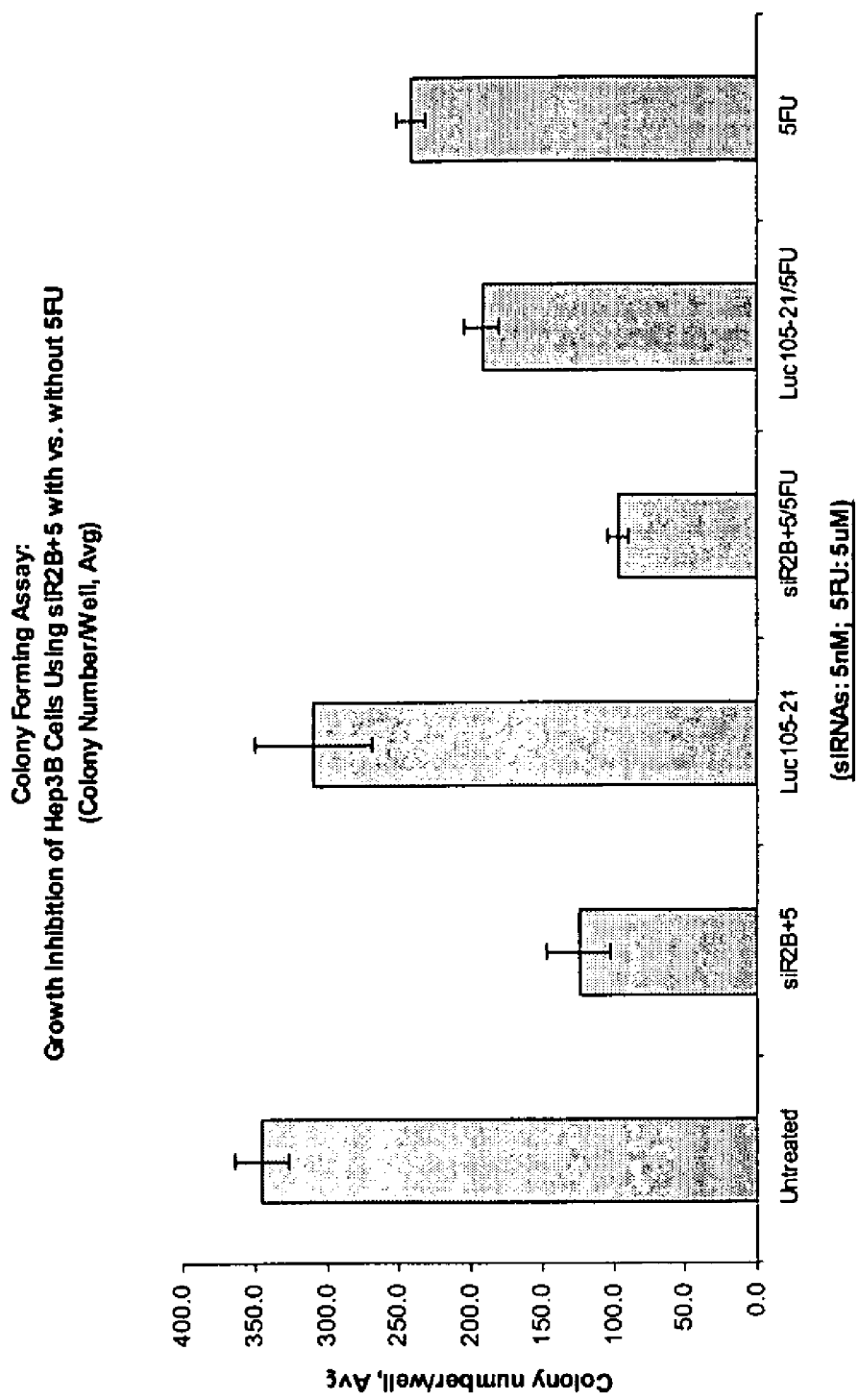
FIG. 19 shows that the reduction of growth potential of Hep3B cells by an siRNA against R2 (siR2B+5) is enhanced by 5-fluorouracil (5-FU) exposure. Human hepatocellular carcinoma (HCC) cells (Hep3B) are dilutely plated and then (1) transfected with luciferase-targeting siRNA (Luc105-21) or siRNA against R2 (siR2B+5) (5 nM), for 4 h and/or (2) exposed to 5 mM 5-fluorouracil (5-FU) for 3 days starting 48 h post-transfection. Five days post-transfection, cells are fixed, stained (methylene blue), and colonies (~50 or more cells) are counted. As seen previously, siR2B+5 reduces colony numbers compared to a non-R2-targeting control (here, Luc105-21). 5-FU alone (without siRNA exposure) reduces colony numbers compared to untreated cells, and 5-FU exposure after siR2B+5 treatment further reduces colony numbers. Columns represent the average of n=3 replicate wells; error bars represent standard deviation.

As shown in FIG. 19, reduction of growth potential of Hep3B cells by siRNA against R2 (siR2B+5) is enhanced by 5-Fluorouracil (5-FU) exposure. As discussed above (see FIG. 17), lipofection of Hep3B cells with optimized siRNA against R2 (siR2B+5) significantly reduces colony formation potential compared to similar treatment with a negative control siRNA (here, that siRNA is Luc105-21, which targets firefly luciferase). Further, exposure of cells to the chemotherapeutic 5-fluorouracil (5 µM for 72 h) reduces colony numbers relative to untreated cells and enhances the antiproliferative effect of siR2B+5.

To conduct the experiments shown in FIG. 19, Hep3B (human hepatocellular carcinoma) cells were received from the American Type Culture Collection. Cells were plated dilutely in six-well tissue-culture plates (500 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"siR2B+5": potent siRNA against hRRM2 (shown as SEQ ID NOs: 63 and 64 in Table 5 above); and "Luc105-21": siRNA against firefly luciferase (used here as a negative control; shown as SEQ ID NOs: 104 and 105 in Table 12 below).

Table 12. Sequence of Luc105-21 used in the Examples described herein. UPPERCASE letters denote DNA residues, lowercase letters denote RNA residues, and underlined residues represent 3' overhangs.

| Description | Sequence | Strand | SEQ ID NO |
|---|---|---|---|
| Luc105-21 | 5' gguuccuggaaca auugcuTT 3' | Sense | SEQ ID NO: 104 |
|  | 3' TTccaaggaccuu guuaacga 5' | Antisense | SEQ ID NO: 105 |

These complexes were exposed to cells at a final nucleic concentration of 5 nM for 4 h, after which the complexes were removed by aspiration and replaced with complete medium. For 5-FU treated samples, growth medium was supplemented with 5 µM 5-fluorouracil (5-FU) at 48 h post-transfection and cells were incubated an additional three days. Five days (120 h) post-transfection, cells were fixed with ethanol (10 min) and stained with methylene blue (in water). Colonies (having ~50 or more cells) were counted manually. Triplicate wells (n=3) were used for each treatment; columns represent averages and error bars represent standard deviation (FIG. 19).

Example 13 siRNA Against R2 Reduces R2 Protein Levels in Tumors in Mice

Figure 20:
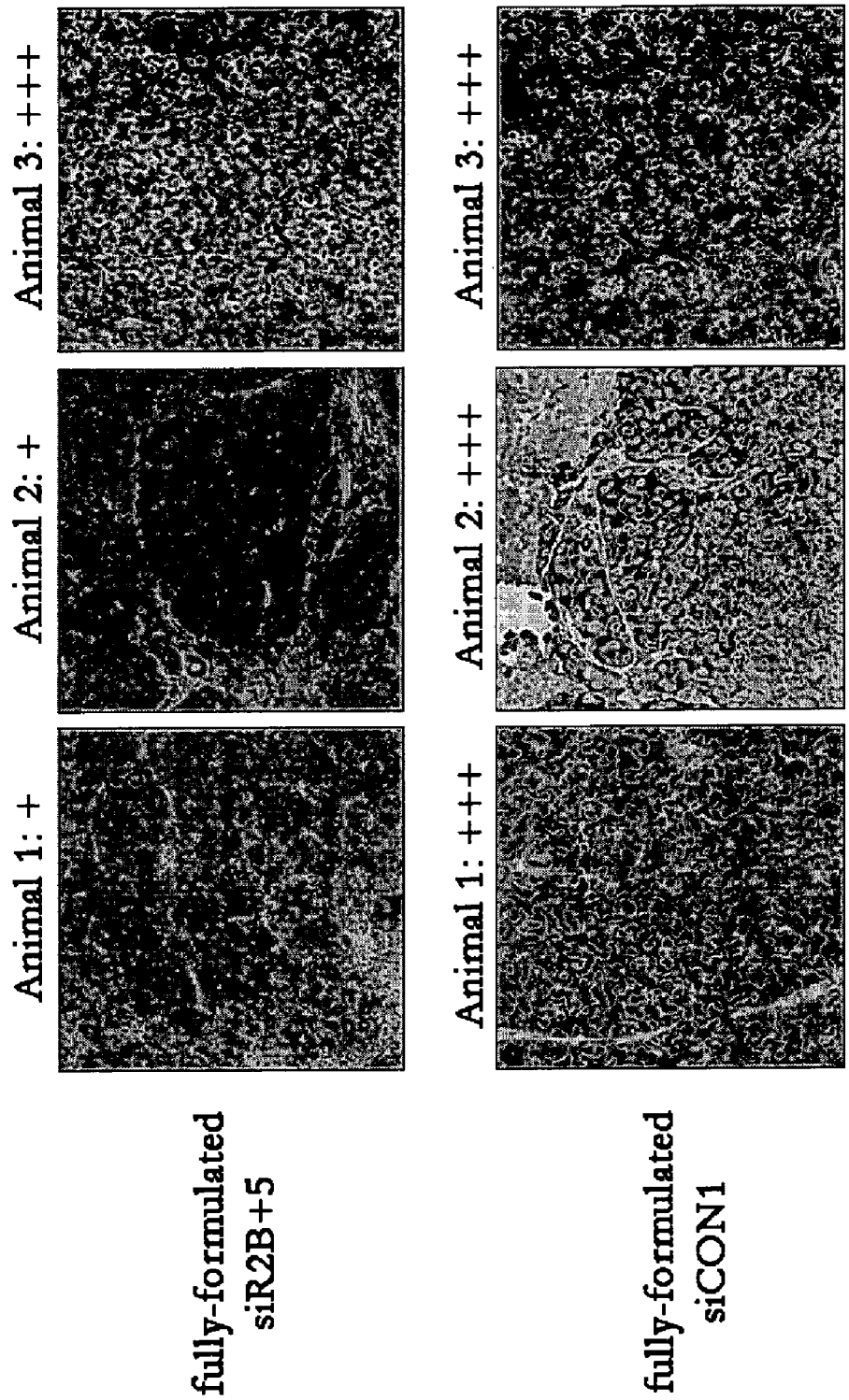
FIG. 20 shows that an siRNA against R2 reduces R2 protein levels within subcutaneous Hep3B tumors in mice. Mice with sub-cutaneous human hepatocellular carcinoma (Hep3B) tumors received three consecutive daily intratumoral (IT) injections of 2.5 mg/kg siRNA (either a non-targeting control siRNA (siCON1) or siRNA against R2 (siR2B+5)) within a polymer-based delivery system. Two days after the third injection, mice are sacrificed and tumors are fixed, paraffin-embedded, sectioned, and immunohistochemistry (IHC) is performed to assess tumor R2 protein levels. In two of three mice treated with formulations containing siRNA against R2, tumor R2 protein levels are sharply reduced compared to those in mice treated with non-targeting control siRNA. This suggests that three consecutive daily intratumoral injections of formulations containing siR2B+5 achieves down-regulation of R2 protein in these tumors. Scoring was carried out using the following scale: +=low R2 protein level, ++=moderate R2 protein level, and +++=high R2 protein levels.

As shown in FIG. 20, siRNA against R2 reduces R2 protein levels within sub-cutaneous Hep3B tumors in mice. In two of the three mice treated with formulations containing anti-R2 siRNA (siR2B+5), tumor R2 protein levels are sharply reduced compared to those in mice treated with non-targeting control siRNA (siCON1). This suggested that three consecutive daily intratumoral injections of formulations containing siR2B+5 achieve down-regulation of R2 protein in these tumors.

To conduct the experiments shown in FIG. 20, Hep3B (human hepatocellular carcinoma) cells were injected subcutaneously into HRLN female nu/nu mice. When the tumors reached an average mass of ~200-300 mg, mice were treated with three consecutive daily intratumoral (IT) injections of optimized siRNA against R2 (siR2B+5) (shown as SEQ ID NOs: 63 and 64 in Table 5) or non-targeting control siRNA (siCON1) (shown as SEQ ID NOs: 97 and 98 in Table 10) within a cyclodextrin-containing polycation (CDP) delivery system possessing an adamantane-poly(ethylene glycol)-transferrin (AD-PEG-Tf) targeting ligand (2.5 mg/kg siRNA per injection). Two days after the third injection, mice were euthanized, tumors were harvested, formalin-fixed, paraffin-embedded, sectioned, and probed for human R2 protein expression via immunohistochemistry (IHC). Sections were scored for relative R2 protein expression (+: low, ++: moderate, +++: high).

Example 14 siRNA Against R2 Reduces Protein Levels in Rat Hepatoma Cells

Figure 21:
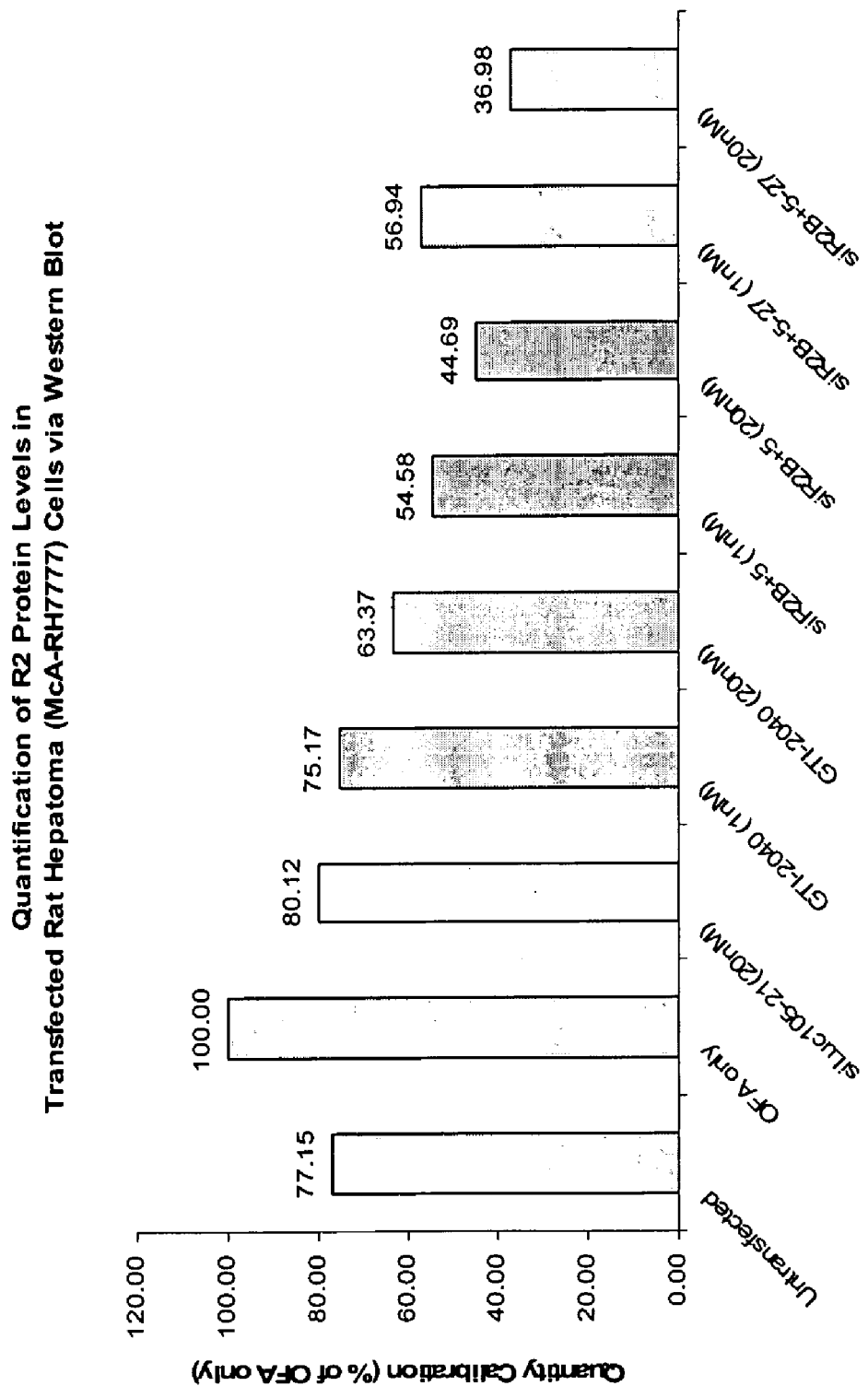
FIG. 21 shows that an siRNA against R2 reduces R2 protein levels in cultured rat hepatoma cells (McA-RH7777). Rat hepatoma cells (McA-RH7777) are plated and then transfected with an antisense molecule against R2 (GTI-2040; 1 nM or 20 nM), siRNA against luciferase (Luc105-21; 20 nM only), a 21mer siRNA against R2 (siR2B+5; 1 nM or 20 nM), or a 25/27mer against R2 (siR2B+5-27; 1 nM or 20 nM). At 48 h post-transfection, cells are lysed and R2 protein levels are measured by Western blot and quantified using ImageQuant software. All molecules directed against R2 (GTI-2040 antisense, siR2B+5 21mer and 25/27mer) show dose-dependent reductions of R2 protein levels that are superior to that of a negative control (Luc105-21, siRNA against luciferase). The R2 reduction from the siR2B+5 21mer and 25/27mer are comparable to each other and superior to that seen with the GTI-2040 antisense molecule.

As shown in FIG. 21, siRNA against R2 reduces R2 protein levels in cultured rat hepatoma cells (McA-Rh7777). All molecules directed against R2 (GTI-2040 antisense, siR2B+5 21mer and siR2B+5-27 25/27mer) show dose-dependent reductions of R2 protein levels that are superior to that of a negative control (Luc105-21, siRNA against luciferase). The R2 reduction from the siR2B+5 21mer and siR2B+5-27 25/27mer are comparable to each other and superior to that seen with the GTI-2040 antisense molecule. Finally, this data suggests that these two duplexes, originally developed against hRRM2, are also capable of achieving down-regulation of the rat ortholog of R2 protein (rRRM2).

To conduct the experiments shown in FIG. 21, McA-RH7777 (rat hepatoma) cells were received from the American Type Culture Collection. Cells were plated in six-well tissue-culture plates (250,000 cells per well) 24 h prior to transfection. For transfection, complexes were prepared in serum-free medium (OptiMEM, Invitrogen) using Oligofectamine (Invitrogen) and each of the following nucleic acids according to the manufacturer's recommendations:

"Luc105-21": optimized siRNA against firefly luciferase (negative control);

"GTI-2040": antisense oligonucleotide against hRRM2;

"siR2B+5": optimized siRNA (21mer) against hRRM2;

"siR2B+5-27": optimized Dicer substrate RNA (25/27mer) against hRRM2;

These complexes were exposed to cells at a final nucleic acid concentration of 1 nM or 20 nM for 4 h, after which the complexes were removed by aspiration and replaced with complete medium. Two days (48 h) post-transfection, cells were lysed and the level of R2 protein was measured by Western blotting using a goat polyclonal anti-R2 antibody (sc-10846, Santa Cruz) at a 1:250 dilution as the primary antibody and an HRP-conjugated donkey anti-goat IgG (Santa Cruz) at a 1:10000 dilution as the secondary antibody. The blots were developed using an ECL Detection Kit (GE/Amersham Biosciences). Quantification of Western blots is performed using ImageQuant TL software (GE/Amersham Biosciences).

Example 15

Delivery Systems for siRNAs

We have engineered a non-viral, nucleic acid delivery system that is based on short, cyclodextrin-containing polycations (CDP). This vehicle is the first example of a polymer-based nucleic acid delivery system formed entirely by self-assembly and is the most tunable vector currently available (Davis et al., 2004). This delivery system reveals extremely low toxicity in vitro and in vivo (in vitro: Gonzalez et al., 1999; Hwang et al., 2001; Pun and Davis, 2002; Reineke and Davis, 2003a,b; in vivo: Bellocq et al., 2003b; Davis et al., 2004; Pun et al., 2004), and allows for systemic administration of oligonucleotides (Pun et al., 2004), siRNA (Hu-Lieskovan et al., 2005) and plasmids (Bellocq et al., 2003b) to animals. Initial work with mice and rabbits has revealed that the delivery system does not cause immune responses, and it has the ability to alter the biodistribution of delivered nucleic acid within the animal (Pun et al., 2004; Hu-Lieskovan et al., 2005). The delivery system consists of self-assembled particles with tunable diameters ca. 50 mm and surface charges. These nanoparticles are formulated entirely by self-assembly methods to provide reproducible and scalable delivery vehicles. The nanoparticles are designed to remain assembled until they "sense" the low pH of the intracellular environment, after which they alter themselves to assist in the intracellular trafficking. The nanoparticles can accommodate targeting ligands for binding to cell surface receptors and their use has provided for targeted delivery in animals (Bellocq et al., 2003b; Pun et al., 2004; Hu-Lieskovan et al., 2005). Therefore, we can: (i) create well-defined nucleic acid delivery vehicles with tunable properties that can be characterized by quantitative methods, and (ii) provide effective delivery and function in rodent animal models.

Liver Cancer

Liver cancer can be of many forms. Cancer of liver cells, i.e., hepatocellular carcinoma, is significantly different from metastatic tumors of other tissue types such as colorectal, breast, lung, etc. that reside in the liver. Primary liver cancer is the sixth most frequent cancer worldwide (Gerolami et al., 2003). The work proposed here is with hepatocellular carcinomas and thus involves cancers of hepatocytes. The 2004 statistics from the American Cancer Society show that the five-year relative survival rate between 1992-1999 for liver cancer that is confined to the liver is 16.3% as compared to other confined tissue: breast (97.0%), colon and rectum (90.1%), prostate (100.0%) and pancreas (16.6%). Thus, liver and pancreas are by far the most lethal, locally confined cancers in humans, and these facts show the need for new therapies with much better efficacy for these cancers. Here, we propose a new therapeutic agent for the treatment of liver cancer. That is, we propose that the inhibition of ribonucleotide reductase (RNR) subunit 2 (R2) by non-virally delivered short interfering RNAs (siRNAs) will provide a new efficacious therapy for liver cancer. The inhibition of R2 alone and in combination with low dose chemotherapeutic agents will give a new therapeutic mechanism of action for liver cancer with an anticipated superior safety profile to current therapies.

Ribonucleotide Reductase Subunit 2 Inhibition for Liver Cancer

Ribonucleotide reductase (RNR) catalyzes the reaction that produces 2'-deoxyribonucleotides from their corresponding ribonucleoside 5'-diphosphates. This reaction is a rate-limiting step in the pathway for the production of 2'-deoxyribonucleoside 5'-triphosphates, and it is necessary for DNA replication. Human RNR consists of two subunits, R1 and R2, and the expression of both proteins is required for enzymatic activity. R1 and R2 are encoded by different genes on separate chromosomes, and most importantly, their mRNAs are differentially expressed throughout the cell cycle. The R1 protein is stable through the entire cell cycle while R2 is only expressed during the late $G_1$/early S phase when DNA replication occurs (Engstrom et al., 1985).

RNR is an interesting target for anticancer therapeutics. Literature evidence suggests that retinoblastoma tumor suppressor suppresses R1 and R2 as one mechanism to control progression through the cell cycle (Angus et al., 2002). The R2 protein also can play a role in determining the malignant potential of tumor cells via interaction with numerous activated oncogenes. For example, Fan and co-workers have shown that anchorage-dependent growth of cells transformed with v-fms, v-src, A-raf, c-myc and others is significantly enhanced when R2 is overexpressed (Fan et al., 1998). Overexpression of R2 has been shown as a factor causing gemcitabine resistance (Liu et al., 2004). Recently, Lin et al. (2004) reported that suppression of R2 by siRNA sensitizes HCT-116 cells to DNA-damaging agents and RNR inhibitors. These and other issues render R2 inhibition a useful objective of anticancer therapeutics (Yen, 2003).

Yen and co-workers (Chen et al., 2000) and Lee et al. (2003) have shown that antisense molecules to R2 can significantly reduce the growth of human cancer cells both in vitro and in vivo. Lee and co-workers have shown that GTI-2040, a 20mer phosphorothioate oligonucleotide (PS-ODN) that has been shown to inhibit the production of R2 at 200 nM in vitro (Orr and Dorr, 2004), significantly inhibits subcutaneous tumors in nude mice of human colon, pancreas, liver, lung, breast, kidney, ovary, brain, prostate, etc. (Lee et al., 2003). These workers also demonstrated that R2 protein levels are elevated in cancer cell lines, and these results are consistent with earlier studies that revealed increased levels of RNR in tumors and tumor cell lines (Jensen et al., 1994). The concept of using R2 inhibition as an anticancer strategy in humans is being tested by workers at Lorus Therapeutics (Lee et al., 2003) who are currently conducting Phase II clinical trials with GTI-2040 (Orr and Dorr, 2004). Phase I results (administered by continuous i.v. infusion for 3 weeks followed by 1 week of rest between cycles to 27 patients with advanced cancer) provided a recommended dose for Phase II trials to be 185 mg/m$^2$/d (5 mg/kg/d) (Orr and Dorr, 2004). The Phase II trial uses GTI-2040 in combination with capecitabine for the treatment of renal cell carcinoma. Initial data from the trial reveal disease stabilization and some tumor responses in some of the 21 evaluable patients (Orr and Dorr, 2004). RNA interference (RNAi) has been shown to be much more potent than antisense molecules for sequence specific inhibition of gene expression and is quickly becoming the method of choice for the regulation of gene expression over antisense, ribozyme or DNAzyme technologies. Very recently, Whang and co-workers have used: (i) siRNA against R2 to enhance pancreatic adenocarcinoma chemosensitivity to gemcitabine (Duxbury et al., 2004a), and (ii) retrovirally expressed siRNA against R2 to attenuate pancreatic adenocarcinoma cellular invasiveness and diminish its gemcitabine resistance (Duxbury et al., 2004b).

These studies and others not reported here show that R2 is an excellent target for liver cancer. Of specific importance to hepatocarcinomas is that the cancer cells will be proceeding through cell cycling as the tumors grow while normal hepatocytes will be quiescent. Thus, off target delivery to normal hepatocytes is unlikely to produce serious side effects. Here, we will create hepatocyte-targeting particles that deliver siRNAs against R2 to hepatocytes in order to inhibit the expression of R2 to provide a new and effective therapy for hepatocellular carcinoma.

Significance of the 50-100 nm Size for the Effective, Systemic Delivery of Therapeutics The length scale of 10's of nanometers is appropriate for agents that must have adequate circulation times to enable significant accumulation and trafficking in tumors. Agents that are less than 10 nm in diameter will quickly (within minutes) be cleared from the circulatory system by the kidney (Jorgensen and Moller 1979). Small molecule therapeutics are eliminated mainly in this manner. Once agents exceed 10 nm in diameter, they cannot physically exit via the kidney. Thus, 10 nm is the lower bound on size for agents that require long (hours) circulation times. The upper bound in size for circulation is the diameter of capillaries. However, this size is too large for effective permeation of tumors. Most solid tumors have characteristics that are not observed in normal tissue. Some of these characteristics are: (i) extensive angiogenesis and hence high vascular density (Matre et al., 1999), (ii) extensive vascular permeability, (iii) defective vascular architecture and (iv) impaired lymphatic clearance from interstital spaces (Fang et al., 2003). The so-called "enhanced permeability and retention" (EPR) effect that is a consequence of tumor characteristics (i-iv) is well known and allows biological and synthetic macromolecules to exit the circulation and accumulate in tumors (Fang et al., 2003; Tanaka et al., 2004). Conventional, low molecular weight drugs normally have plasma half-lives of minutes. The EPR effect requires hours for significant accumulation to occur. Thus, uptake in tumors by the EPR effect is enhanced for entities that do not clear via the kidney (above 10 nm size). Entities that are within the 100's of nm in diameter can exit the circulatory system and enter tumors. Agents of this size have few other locations that are accessible from the circulatory system but one other tissue is liver (endothelium fenestrations are approximately 100-150 nm). Upon exiting the circulatory system and entering the tumor mass, the agents need to have some mobility within the tumor. We have found through experimentation (shown below) that agents of approximately 50 nm in diameter provide a good compromise in size. That is, if the agents are 10 nm they cannot carry much therapeutic while sizes above 100 nm limit mobility in tissue. For hepatocellular carcinoma, this size is also very appropriate for delivery to tumor cells in that the particles must also cross liver fenestrations (ca. 150 nm; Guyton, 1981) and engage the ASGPR (sizes below 70 nm; Rensen et al., 2001).

Figure 22:
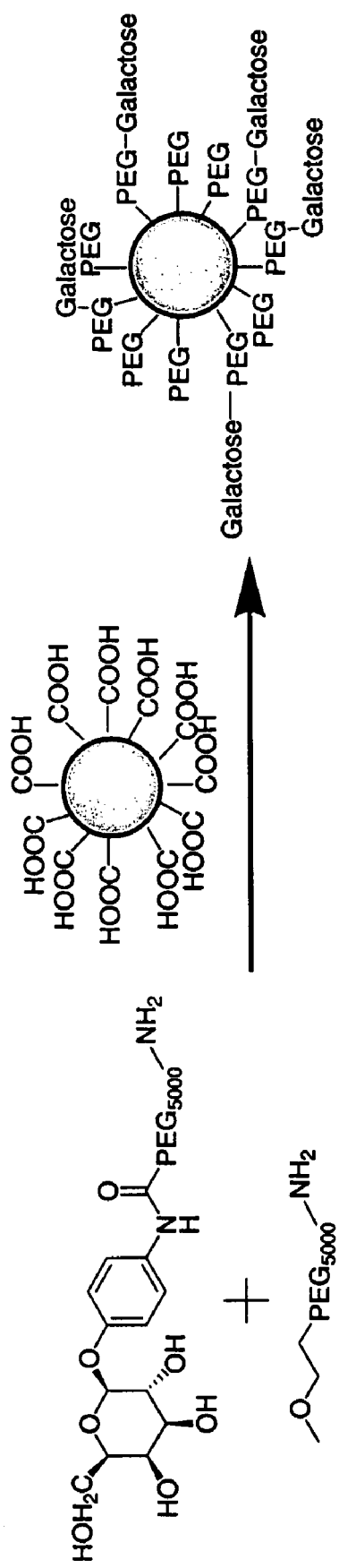
FIG. 22 is a schematic representation of a method for preparing model particles for delivery to hepatocytes. The presence or absence of the galactose-PEG compound yields galactose-containing or just PEGylated beads, respectively.
Figure 23:
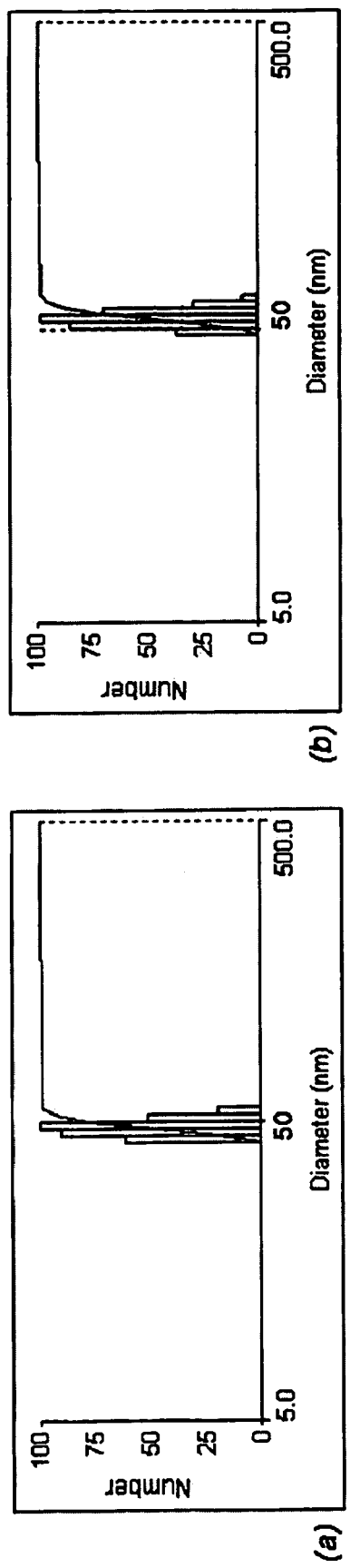
FIG. 23 shows size distribution by dynamic light scattering (DLS) of particles prepared for delivery of an siRNA.

Davis and co-workers have investigated the effects of size and targeting ligand on reaching the intracellular location of hepatocytes from a systemic injection. Using fluorescently-labeled, monodisperse polymer beads, four types of particles were synthesized by the methods schematically shown in FIG. 22. The properties of the beads are listed in Table 1, and a typical size distribution is given in FIG. 23 along with a formulated siRNA particle (details in later sections) to show that the beads are good models for the therapeutic particles.

TABLE 11

Beads for uptake experiments.

| Bead name | Mean diameter (nm) | z-potential (mV) | Galactose surface density (pmol/cm$^2$) |
|---|---|---|---|
| Gal-50 | 51.5 | −2.7 | 25.4 |
| MeO-50 | 53.5 | −2.7 | 0 |
| Gal-140 | 138.1 | −2.6 | 30.6 |
| MeO-140 | 138.7 | −3.2 | 0 |

Figure 24:
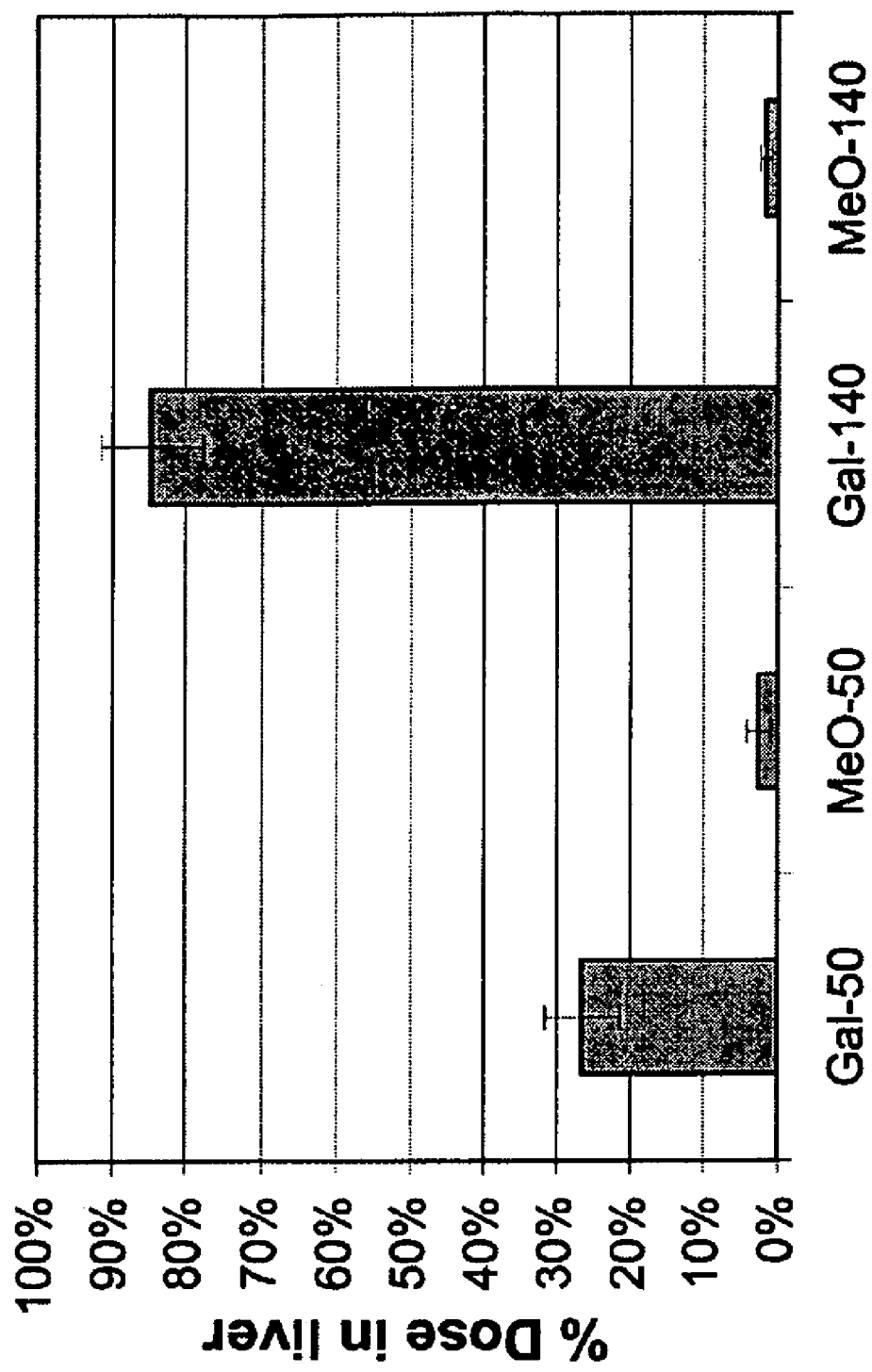
FIG. 24 shows liver uptake of the Gal-50, MeO-50, Gal-140 and MeO-140 particles injected through the tail vein of mice at 20 minutes post-injection.
Figure 26:
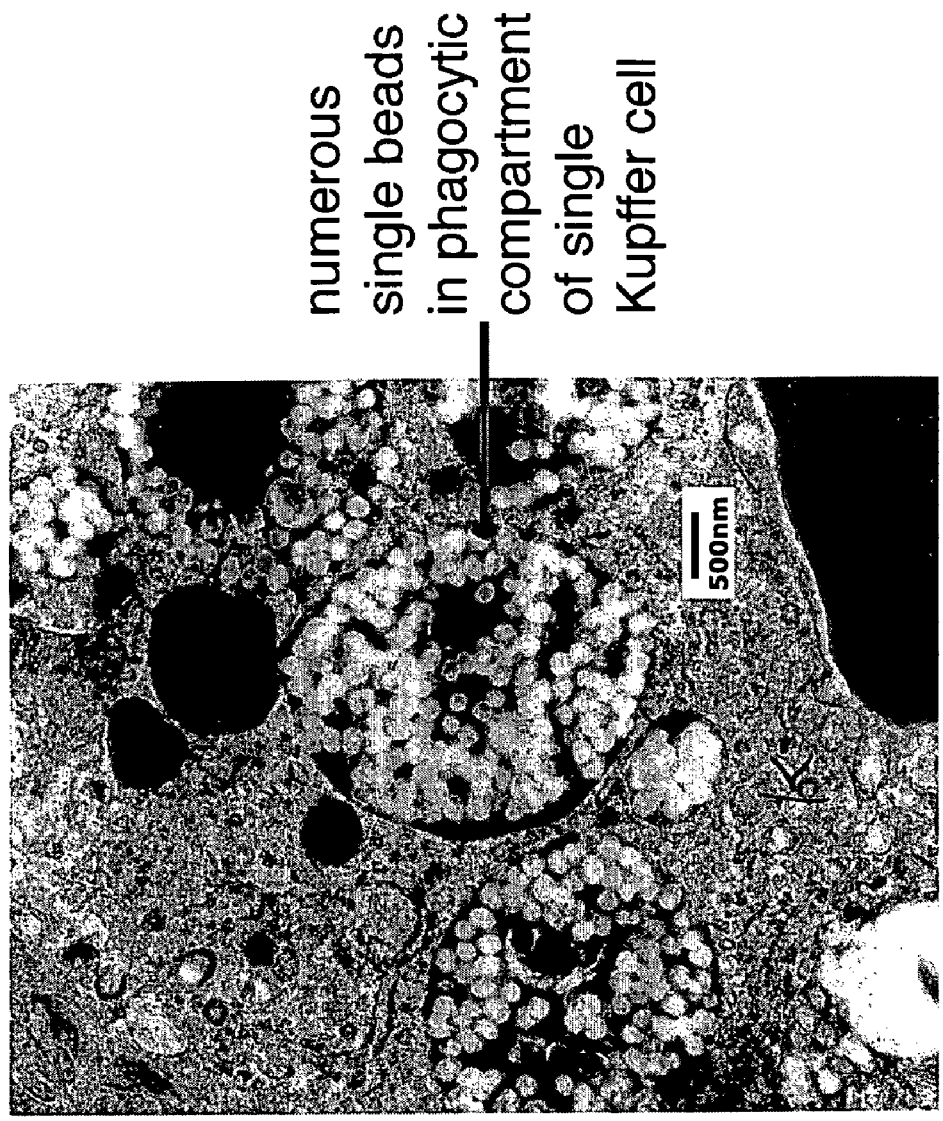
FIG. 26 is a TEM image showing that the Gal-140 particles are located within a Kupffer cell and do not reach the inside of hepatocytes.

When exposing the same number of beads to mice by tail vein injections the percentage of the dose collected in the liver is given in FIG. 24. Note that the particles that lack galactose do not accumulate to a significant amount. Liver sections (FIG. 25) reveal that Gal-140 particles do not really reach hepatocytes (FIG. 25A) but are taken up in Kupffer cells as individual particles (FIG. 26), and this result shows that the particles do not aggregate in blood, tissue and within the cell. On the other hand, the Gal-50 particles are located intracellularly in hepatocytes throughout the sample (FIG. 25B). Nuclei were visualized with blue stain while the beads were visualized as green.

These data suggest that particles with sizes ca. 50 nm can have significant movement throughout tissue and enter cells. While these studies involved targeting of hepatocytes, we have observed similar behavior in tumors. Transferrin-targeted particles carrying fluorescently-labeled DNAzymes of 50 nm in size have been shown to locate within tumor cells from a tail vein injection in mice while 50 nm particles that lacked the transferrin targeting ligand localized to the tumor by the EPR effect but did not enter the tumor cells (Pun et al., 2004). Thus, these two studies reveal that particle sizes of around 50 nm in diameter are appropriate for effectively achieving intracellular locations in hepatocytes and tumors from a systemic administration.

Design and Function of a Self-Assembling Nucleic Acid Delivery System

Figure 28:
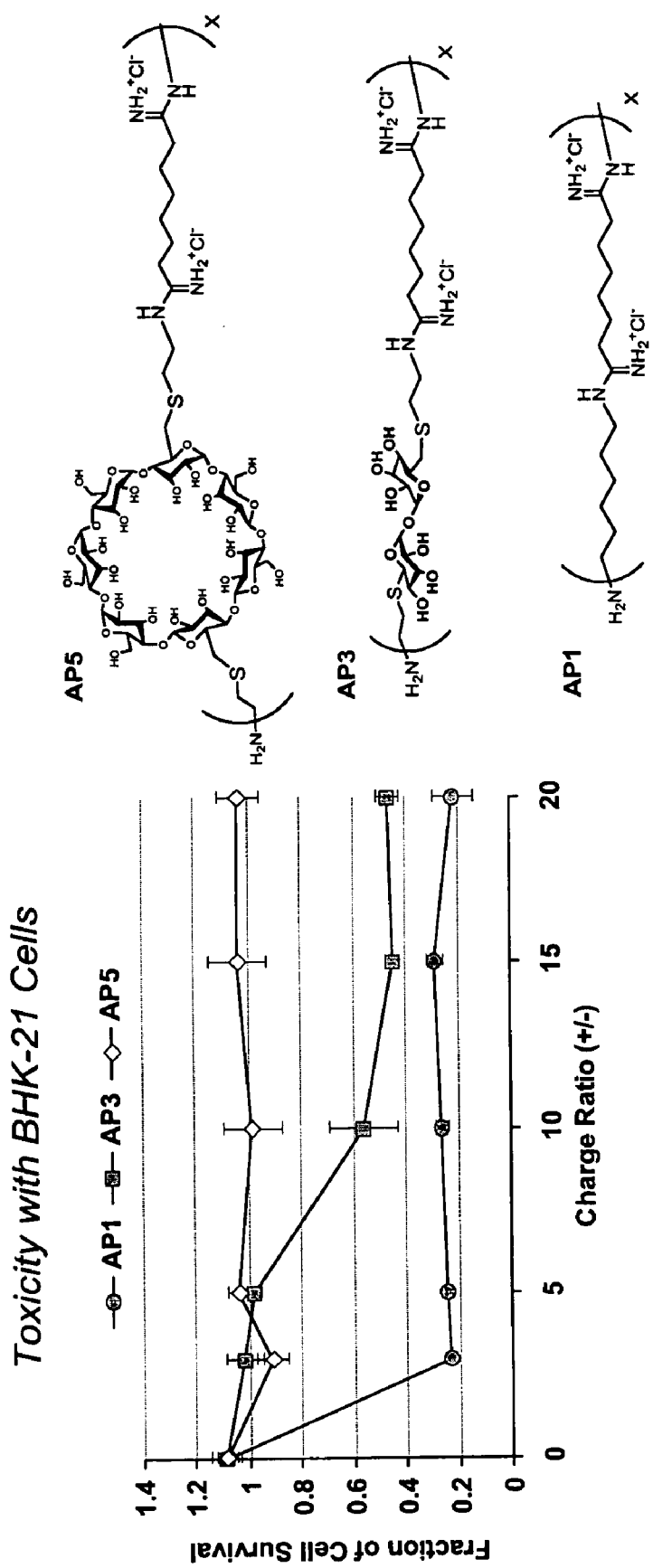
FIG. 28 illustrates the effect of polycation hydrophobicity on toxicity. The cyclodextrin component in AP5 as illustrated reduces cytotoxicity.

Our non-viral delivery system (Gonzalez et al., 1999; Hwang et al., 2001; Pun and Davis, 2002; Reineke and Davis, 2003a,b) involves two components. The first component is a cyclodextrin-containing polycation (see FIG. 27). By preparing numerous polycations that have variations in charge spacing, charge center type and hydrophobicity (by changing the hydrophobicity of the polymer backbone), the in vitro toxicities were shown to correlate with polycation hydrophobicity (see FIG. 28). The CD-containing polycation interacts with nucleic acids of sizes from short single-stranded oligos to large plasmids (we have used up to 10 kbp), self-assembles with the nucleic acids via electrostatic interactions (positive on polymer, negative on nucleic acid) to form polyplexes of ca. 50-100 nm that contain 100% of the nucleic acid in the mixture, and completely protects the nucleic acid from nuclease degradation (Hwang et al., 2001; Pun and Davis, 2002). TEM images suggest that the polyplexes possess spherical morphology (Hwang et al., 2001). FE-SEM and TEM steropairs confirm that the particles have spherical morphology and cryo-TEM images show that these particles are dense. The polycations give low toxicity (for the polycation alone: $IC_{50}$ in vitro above 1 mM and well tolerated in amounts above 100 mg/kg in mice (Hwang et al., 2001); for fully formulated particles: CDP amounts can be over 500 mg/kg in mice with no acute toxicity (Pun et al., 2004). Clearly the cyclodextrin is an important feature for providing low toxicity.

Figure 30:
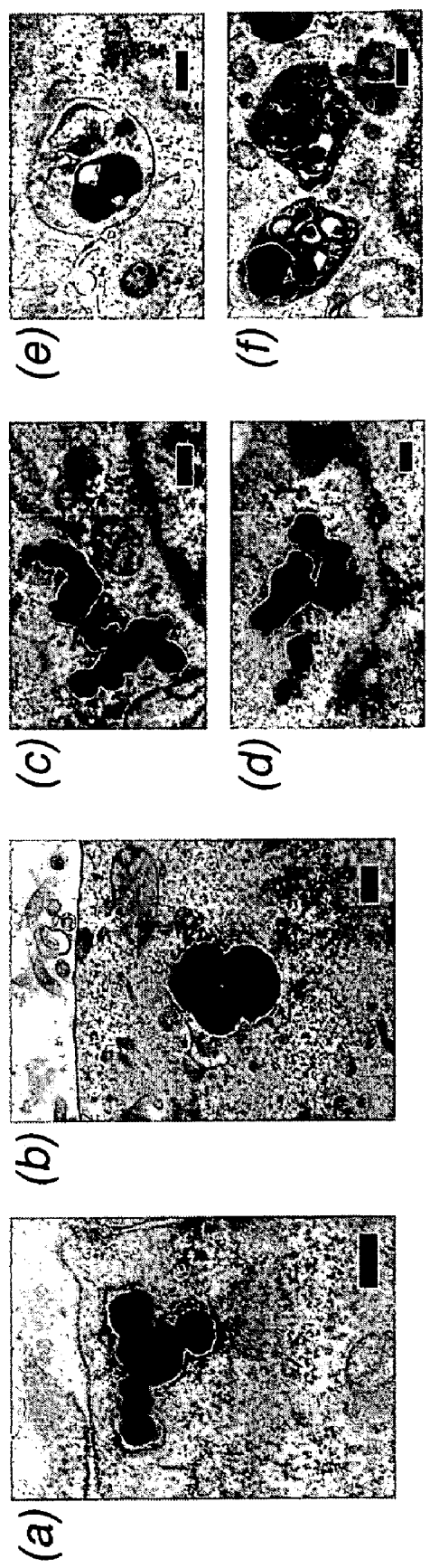
FIG. 30 are TEM images of BHK cells exposed to CDP/pDNA (panels a, c, and d) or im-CDP/pDNA (panels b, e, and f) polyplexes. In (a) and (b) the intracellular vesicles are close to the cell membrane and not at low pH. In (c-f), the vesicles are near the nuclear membrane and are at pH values near f. For (e) and (f) complex unpackaging is observed while in (c) and (d) it is not.

In vitro delivery of plasmid DNA (pDNA) is illustrated by the data given in FIG. 30. Other polycations that provide buffering at pH values below 7 somehow aid in enhanced gene expression (Zuber et al., 2001; Putnam et al., 2001). In order to make the CDP have this type of buffering capability and be appropriate for in vivo studies, imidazole ($pK_a$~6.2) groups were conjugated to the ends of the CDP as illustrated in FIG. 27.

Figure 31:
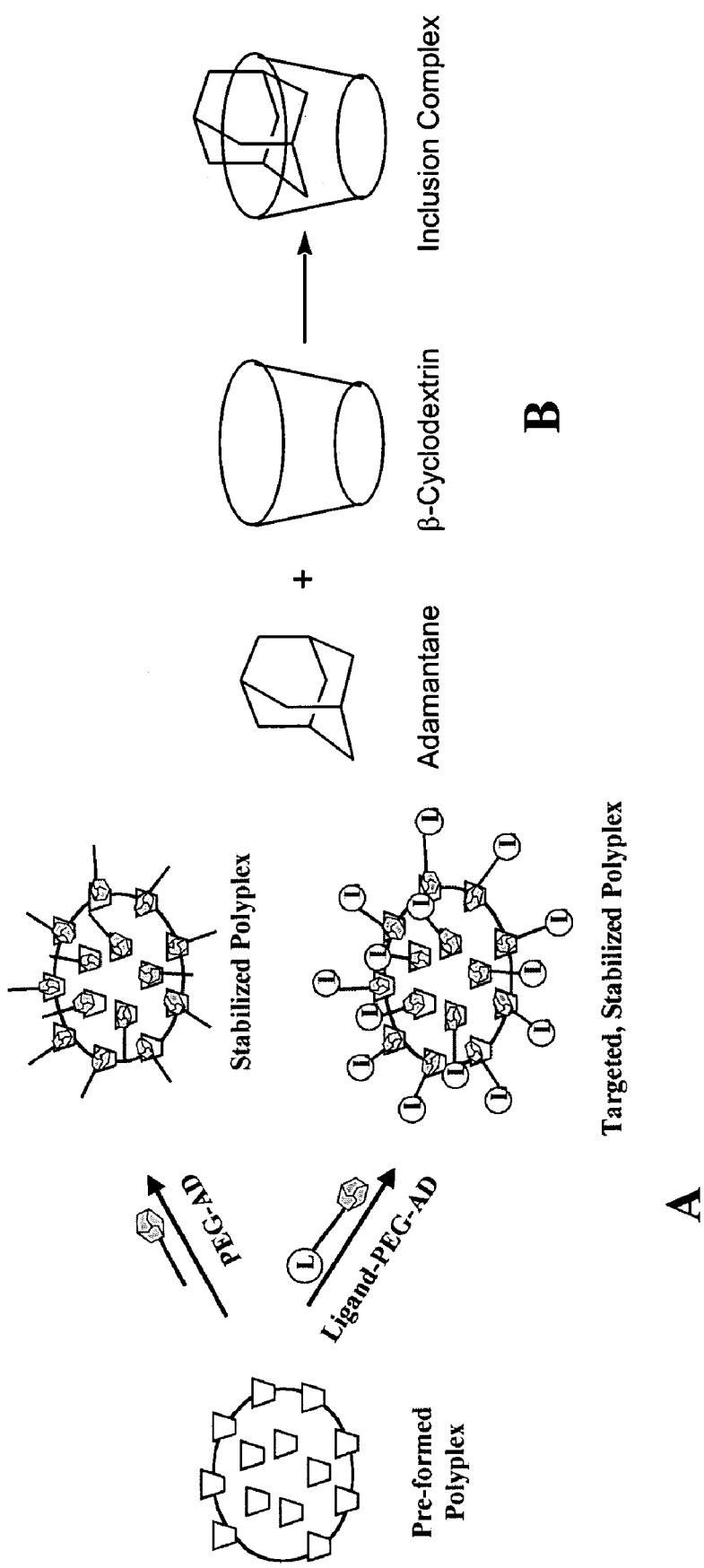
FIG. 31 shows schematic representations of cyclodextrin-containing polyplex surface modification (e.g., pegylated or targeted), and inclusion complex formation with adamantane (AD)-PEG conjugates and β-cyclodextrin.
Figure 32:
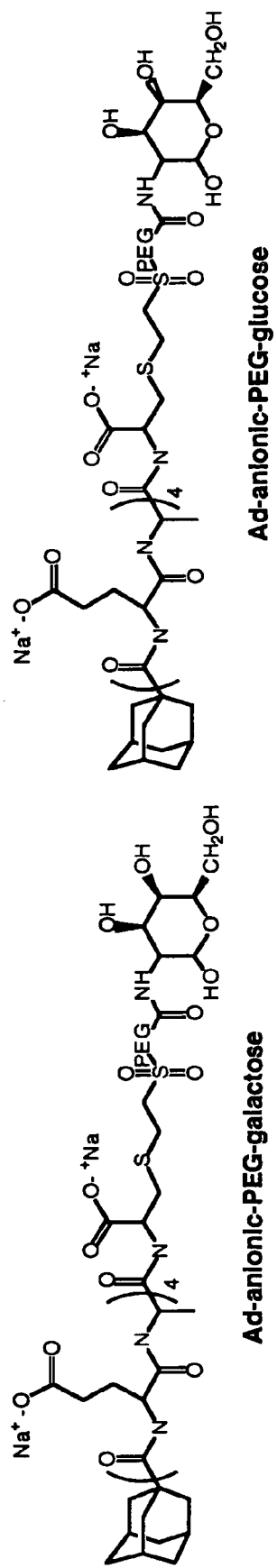
FIG. 32 shows examples of modifying components illustrated in FIG. 31. The glucose modifier is used as a control for galactose-targeting investigations.

The imidazole-containing CDP does buffer the pH of endocytic vesicles (recent measurements with other pH sensitive fluorescent probes in live cells conclusively show that the pH is buffered—data not shown). The buffering of the endosomes causes osmotic swelling that ultimately can lead to vesicle rupture to provide release of the nucleic acid. Additionally, the protonation of imidazole on the CDP causes the polymer to release the nucleic acid. FIG. 31 shows TEMs that illustrate this point.

The polyplexes described above with CDP or im-CDP suffer the same problems as other polyplexes in the sense that they are positively charged colloidal particles that aggregate at physiological conditions. Attempts to provide salt and serum stabilization of polyplexes by PEGylation (PEG: polyethylene glycol) has yielded mixed results. PEGylation can prevent pDNA binding and condensation (Garrett et al., 2000) or change polyplex morphologies (Nguyen et al., 2000). However, successful examples of pDNA condensation after PEGylation of polycations do exist (Kwok et al., 1999). Davis and co-workers developed a new method of EGylating polyplexes that contain cyclodextrins. FIG. 31 illustrates the methodology (Pun and Davis, 2002).

Figure 33:
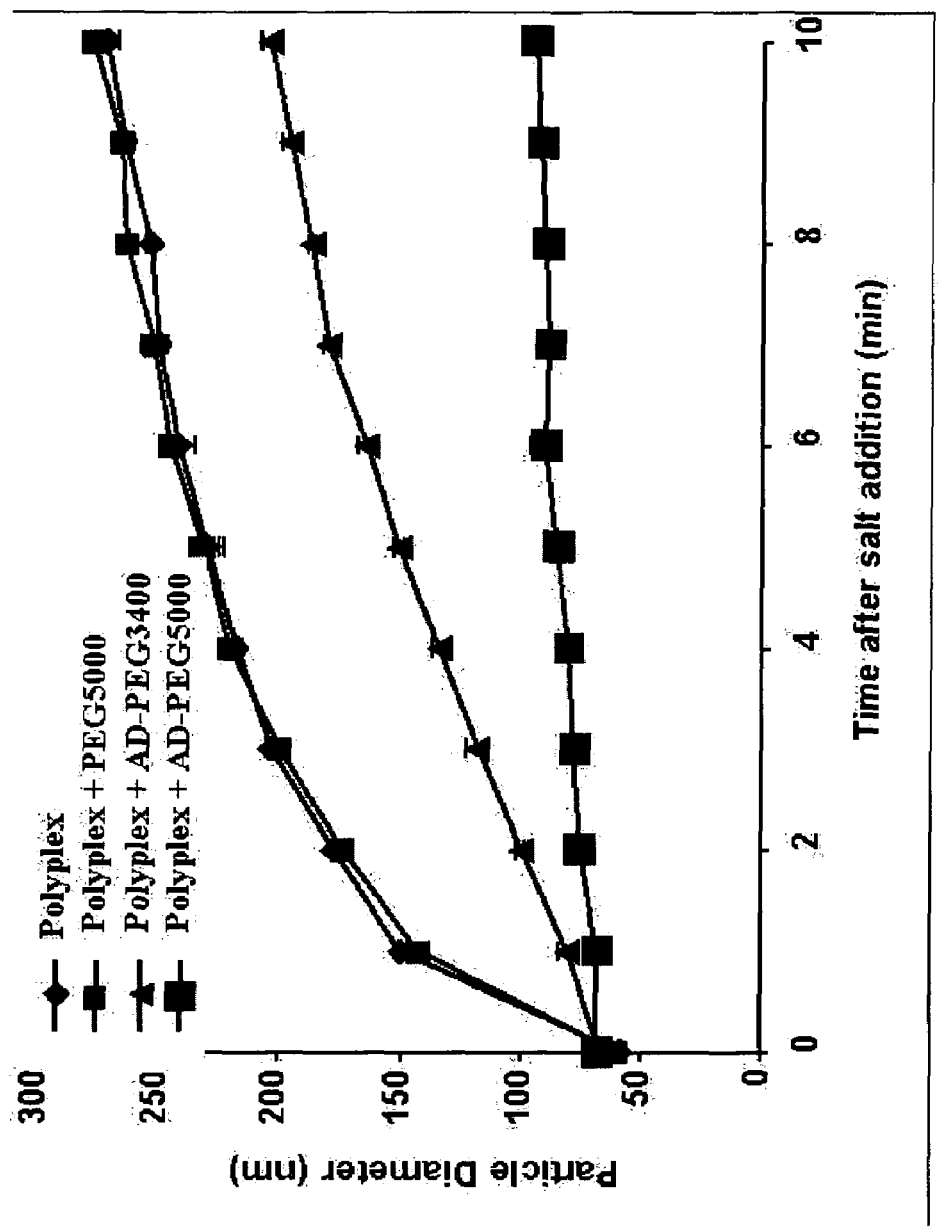
FIG. 33 shows stabilization of polyplex particles in a 50 mM salt solution. Complete stabilization is achieved with AD-PEG5K (PEG5K denotes PEG of 5000 molecular weight). The addition of PEG5K (control) does not provide any stabilization. The increase in size is not from restructuring of particles but rather aggregation of 60 nm starting particles (confirmed by TEM images).
Figure 34:
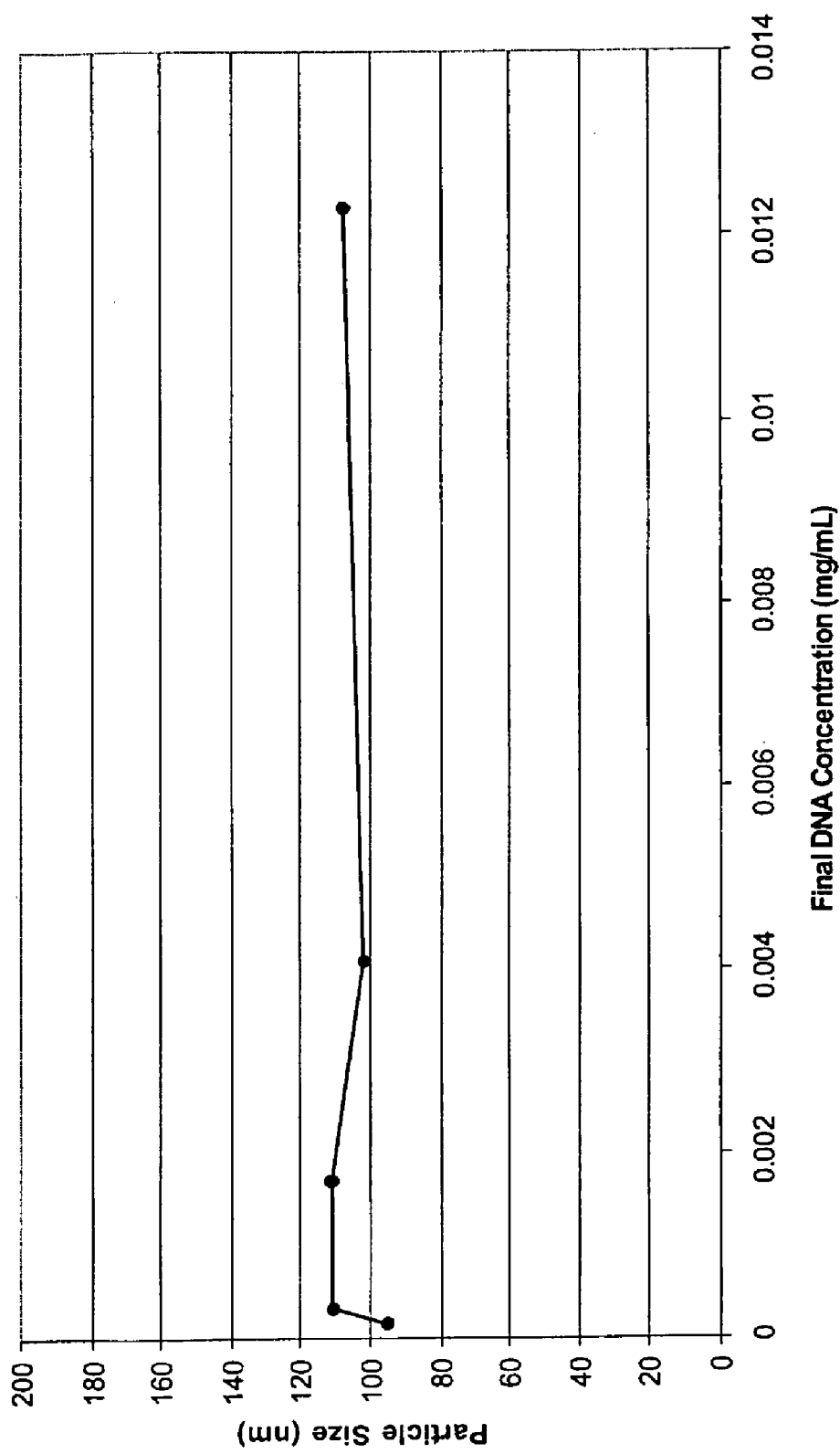
FIG. 34 shows size of particles formed by combining CDP and AD-PEG5000 (AD-PEG5K) before the addition of plasmid DNA (pDNA). Particles were formulated at 1 mg DNA/mL diluted in PBS. Complete stabilization in 150 mM salt with over 1000-fold dilution is achieved with AD-PEG5K.
Figure 35:
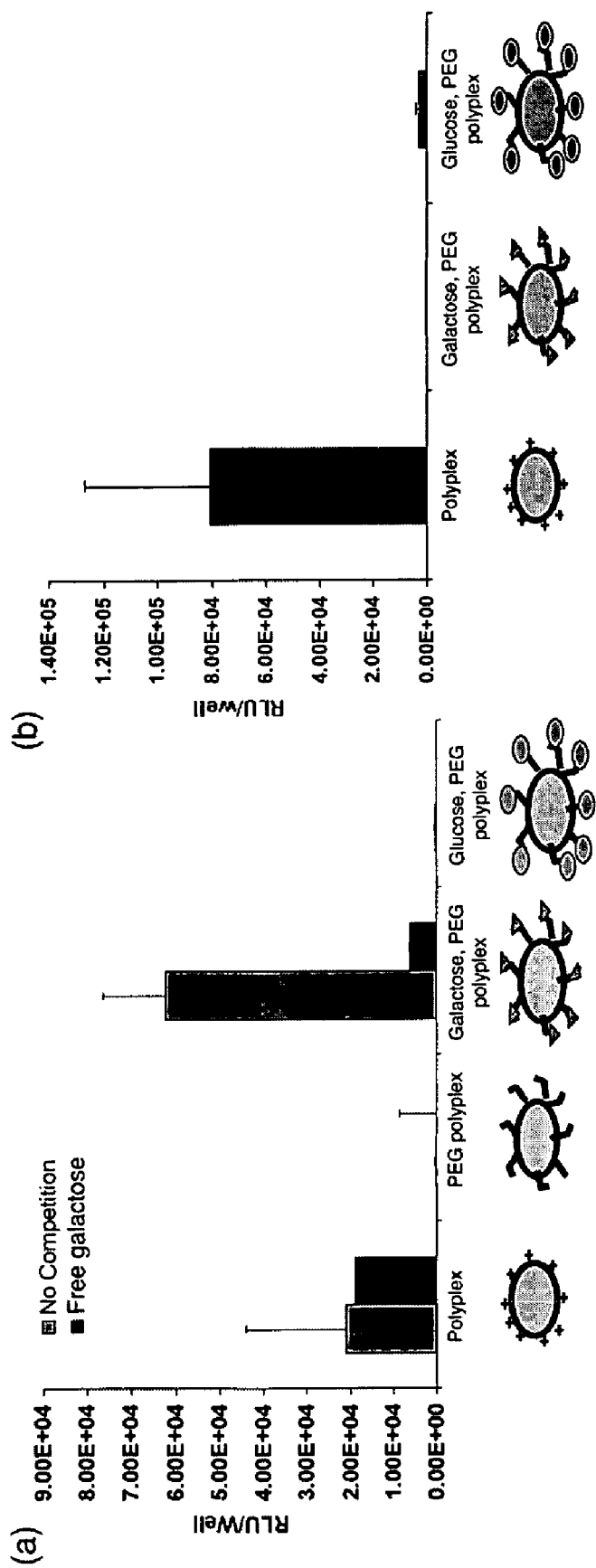
FIG. 35 shows delivery of the luciferase gene using different polyplexes as indicated. (a) HepG2 cells containing the surface asialoglycoprotein (ASGP)-receptor. (b) HeLa cells that do not contain the surface receptor. Cellular uptake can be mediated via surface receptors.
Figure 36:
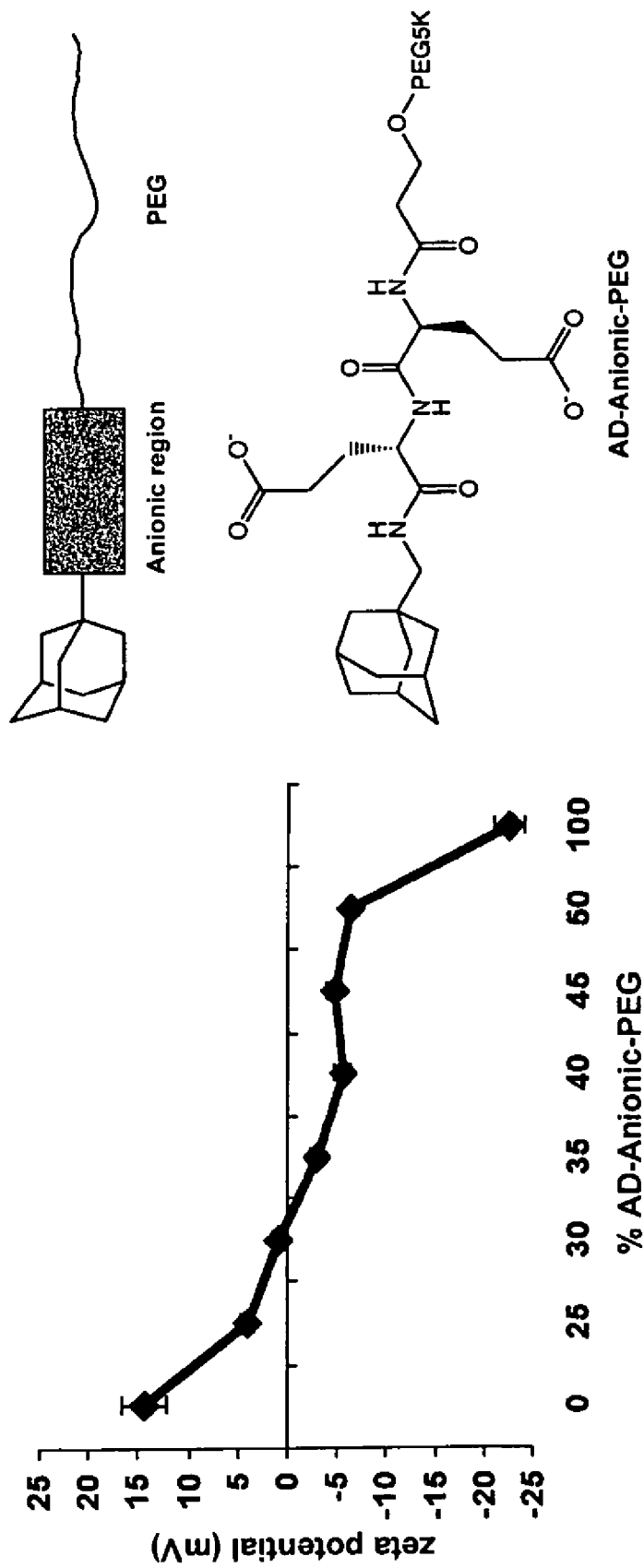
FIG. 36 is an example of tunable surface charge on particles by using an anionic segment in the modifying agent. 100% AD-anionic-PEG represents a 1:1 molar ratio of adamantane (AD) to cyclodextrin (CD) in the system.

The modifying component (examples shown in FIG. 32) has a terminal adamantane (AD) for forming inclusion complexes with surface cyclodextrins, a charged segment, a segment of PEG and a targeting ligand. Pun and Davis have shown that the modifiers decorate the surface of the particles and in so doing allows one to create particles that: (i) are stable at physiological salt conditions (FIGS. 33 and 34) (Pun and Davis (2002)), (ii) can target cell surface receptors (FIG. 35) and (iii) have prescribed surface charge (FIG. 36) and number of targeting ligands (Pun and Davis, 2002).

Figure 37:
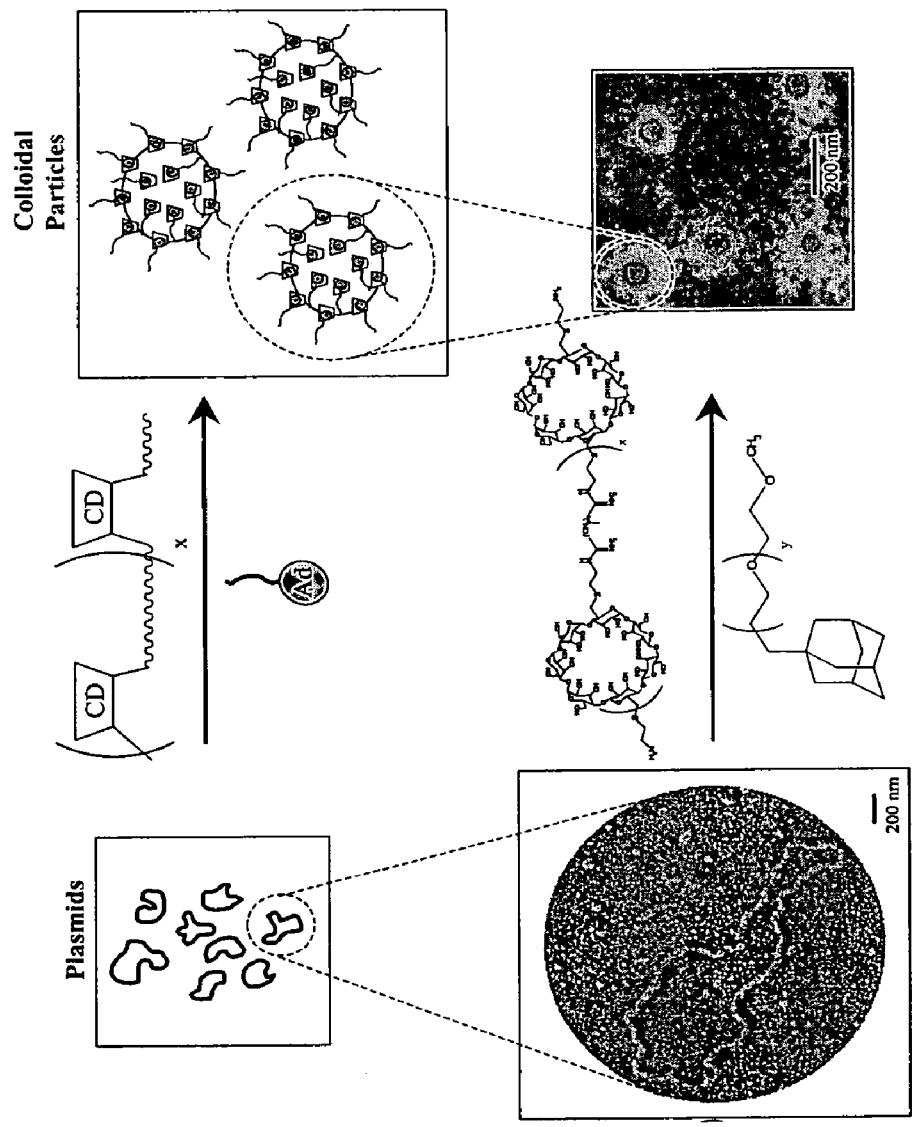
FIG. 37 is a schematic representation of self-assembly of the polyplex particles.

Currently, formulation of stabilized particles is achieved by mixing the polycation and the modifier before adding them to nucleic acids. The entire system spontaneously self-assembles into uniformly sized particles (100% of the nucleic acid is in the particles) within seconds after the three components are mixed together (see FIG. 37), and this formulation can be done with pDNA concentrations as high as 10 mg pDNA/mL.

Figure 38:
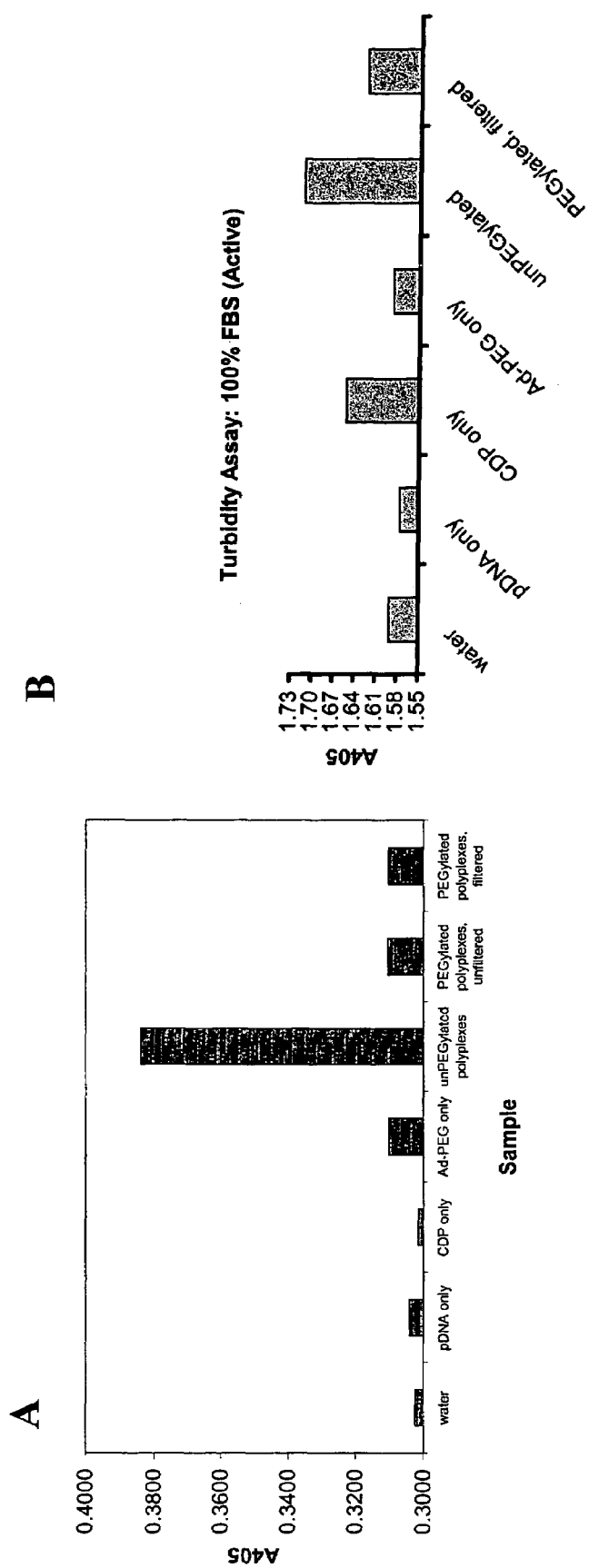
FIG. 38 shows turbidity assay in culture media (A) or 100% FBS (B) of various polyplex particles after 1 hour. UnPEGylated polyplexes aggregate while PEGylated polyplexes as formulated or after the removal of unbound components do not aggregate.

The physicochemical behavior of the gene delivery particles has been tested in model biological fluids. As shown above, the particles are stable in 150 mM NaCl. Additionally, we test for stability in the presence of blood and blood components using a turbidity assay. That is, if aggregation occurs, the aggregated entities scatter more light that can be quantitatively measured. FIG. 38 illustrates this assay and shows that while unPEGylated polyplexes aggregate in culture media (a), or 100% active fetal bovine serum (FBS) (b), the PEGylated particles do not.

Figure 39:
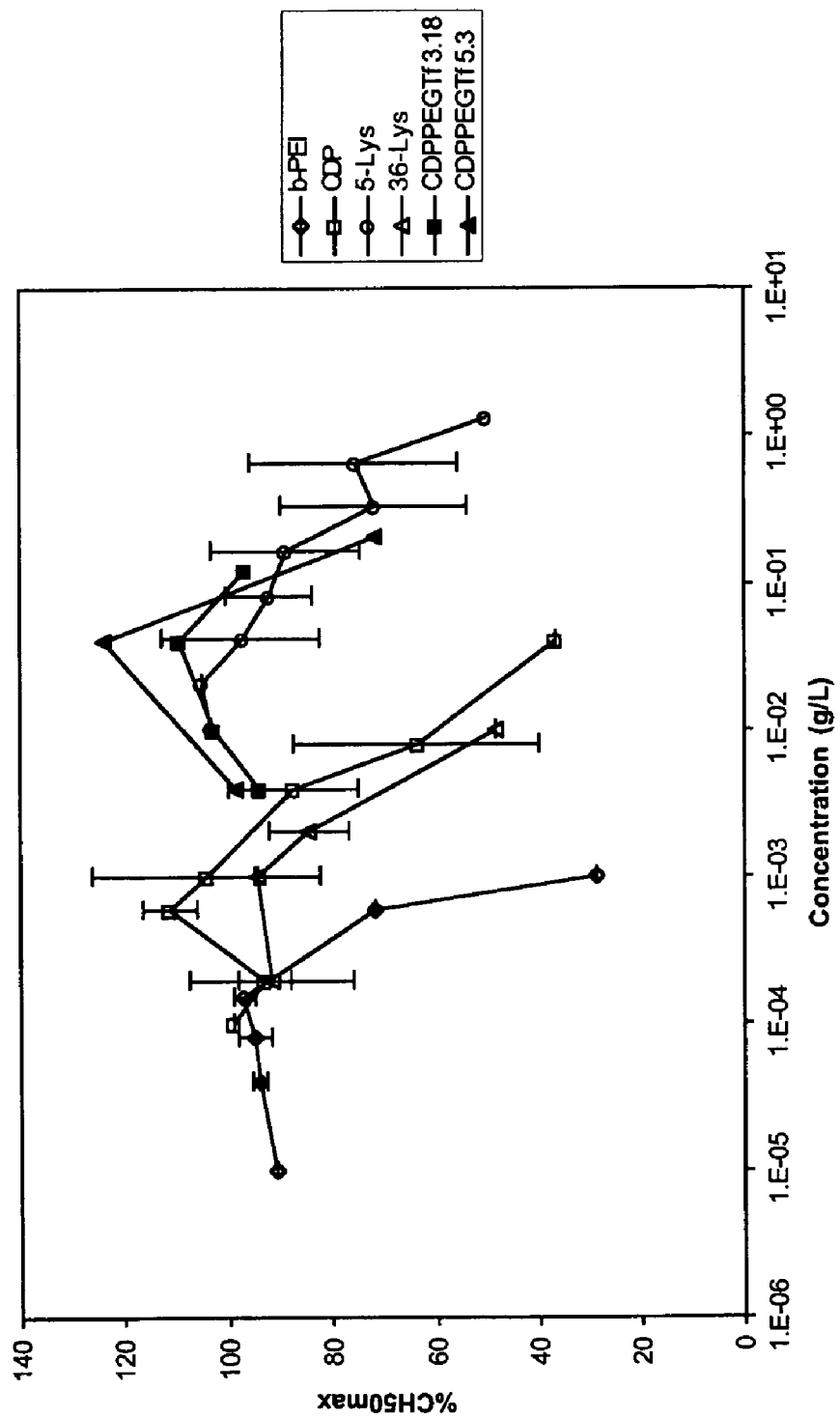
FIG. 39 shows the fully-formulated particles do not activate the complement system. CDPPEGTf denotes fully formulated particle with a charge ratio of either 3.18 or 5.3 (+/−).

Cationic lipids and polymers have been shown to activate the complement system (Plank et al., 1996). FIG. 39 shows that polycations like PEI and the CDP do in fact show complement activation consistent with data reported by Plank et al. (1996). However, fully formulated particles (Tf-PEG-AD, AD-PEG, CDP and pDNA) do not activate complement at the concentrations used in animals even when the free components are not removed (Tf-PEG-AD; transferrin(Tf)-containing PEG-AD where Tf is used for targeting tumors (Pun et al. 2004).

Systemic Delivery of Nucleic Acids in Mice

Galactose Targeting to Liver with siRNA

Naked siRNA is not taken up into cultured cells while the CDP formulated material (50 nm particle diameter; FIG. 23b) enters essentially all the cells (FIG. 40). In our hands, naked siRNA is not stable in serum while the CDP formulations provide protection against nuclease degradation (we have shown protection up to 72 h). Thus, CDP/siRNA formulations are stable in serum and deliver siRNA into cells.

Figure 41:
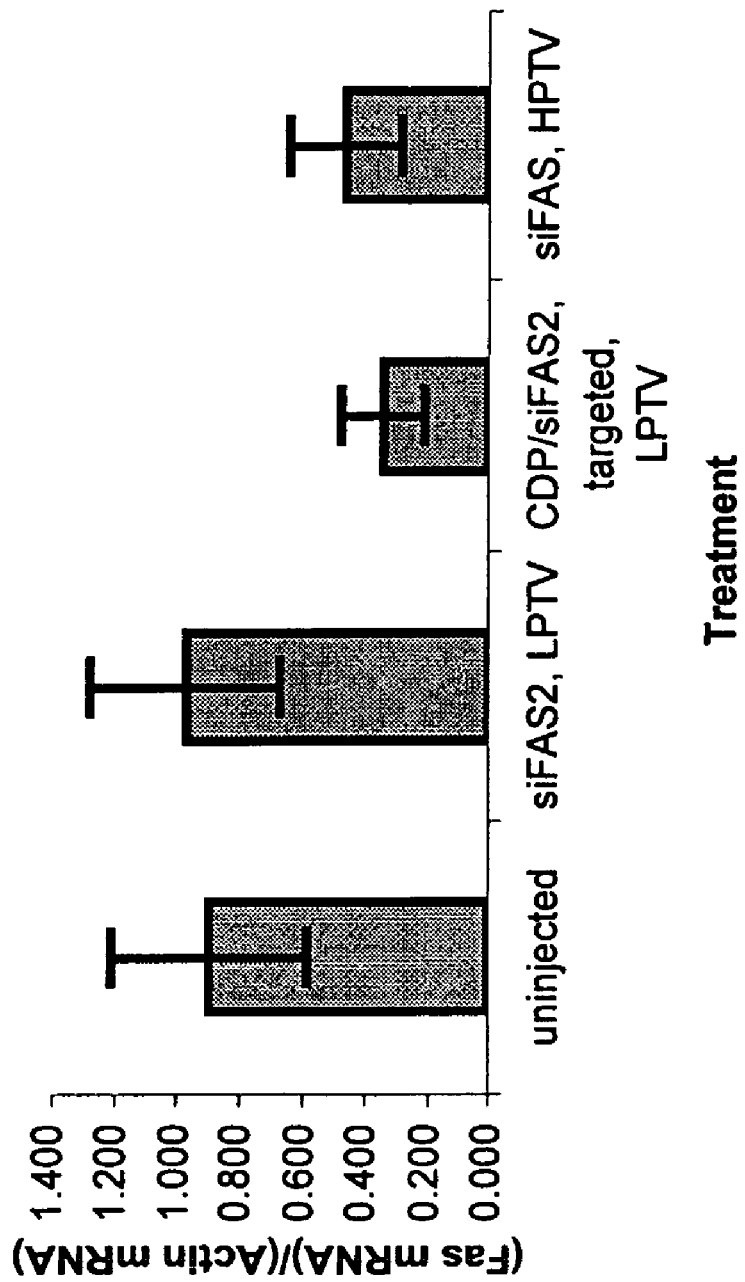
FIG. 41 compares quantitative RT-PCR results from BALB/c mice injected with 50 μg of siRNA in different delivery formulations by high pressure tail vein injection (HPTV; 2 mL volume injected) or low pressure tail vein injection (LPTV; 0.2 mL volume injected).

In a study targeting hepatocytes in mice, we used the siRNA sequence of Song et al. (2003) to down-regulate the FAS gene. Song et al. (2003) showed that hydrodynamic injection (~1 mL of solution rapidly injected in tail vein) reduced FAS mRNA levels. The hydrodynamic injection method is well known to deliver nucleic acids to hepatocytes (Liu et al., 1999; Zhang et al., 1999; Yant et al., 2000) including siRNAs (McCaffrey et al., 2002; Lewis et al., 2002; Song et al., 2003). Using BALB/c mice and 50 μg injections of siRNA, the data shown in FIG. 41 were obtained by quantitative, RT-PCR. As reported by Song et al. (2003), the hydrodynamic injection method (labeled HPTV) reduced FAS mRNA levels while standard, low volume (200 μL) injections of naked siRNA did not. However, galactose-containing, im-CDP formulated particles gave similar FAS mRNA reduction (using a standard low volume (200 μL) injection) to that observed with the HPTV method.

Transferrin Targeting to Tumors with siRNA

To facilitate the delivery of nucleic acids to cancer cells, transferrin (Tf) was incorporated into our delivery system as a targeting ligand (Bellocq et al., 2003a). Transferrin receptors (TfR) are present on the surfaces of malignant cells at levels much higher than on normal cells.

A disseminated tumor model has been created in NOD/scid mice by tail vein injections of TC-71 cells that were transduced with a lentivirus to enable integration of the luciferase gene (TC71-LUC). TC-71 cells are Ewing's sarcoma cells that contain a fusion gene called EWS-FLI1 and have TfR on their surface. The protein product from this fusion gene is known to participate in cell proliferation.

Figure 29:
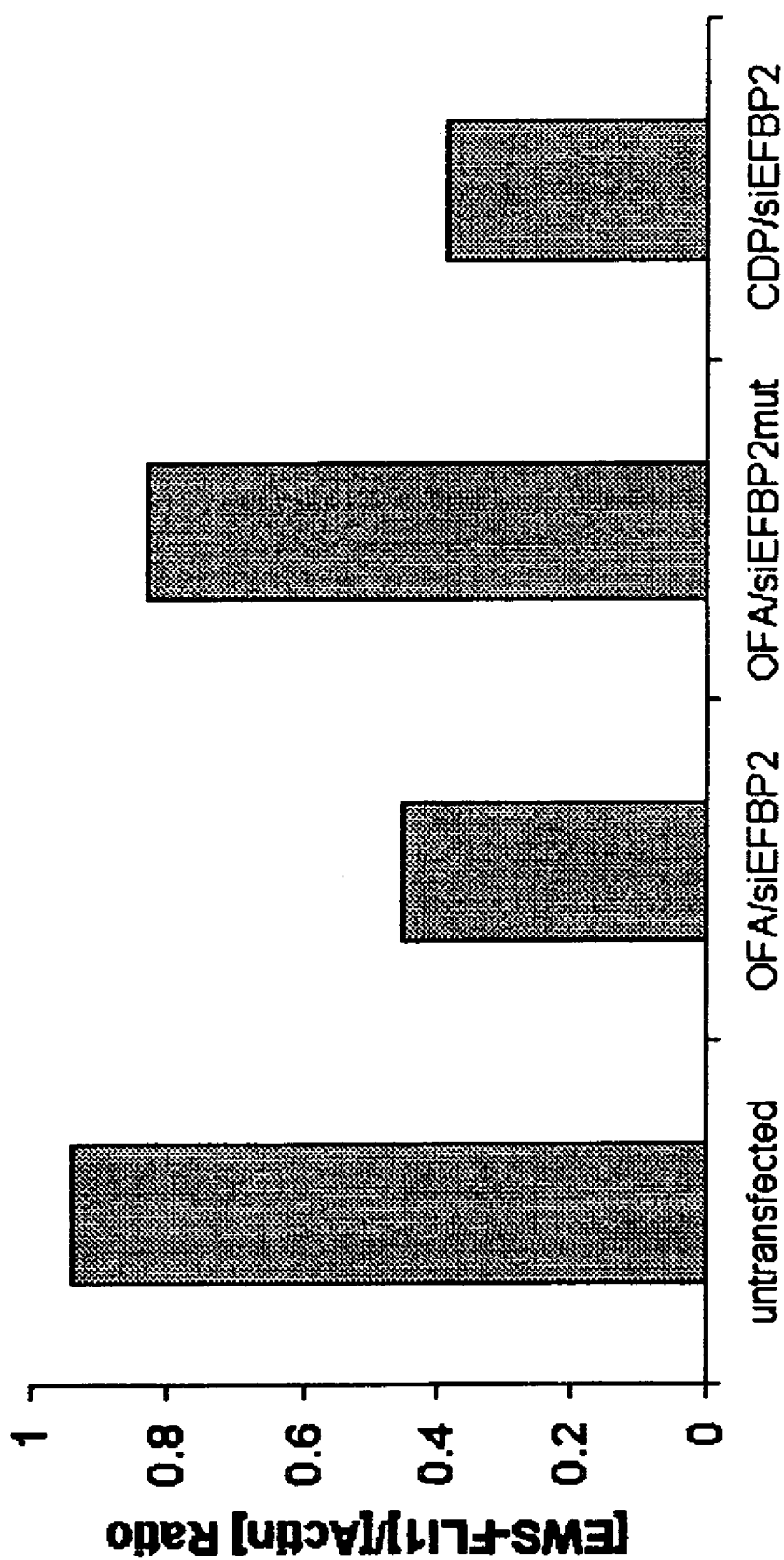
FIG. 29 shows im-CDP as a delivery vehicle for siRNA delivery to cells in vitro. Cultured human Ewing's sarcoma (TC-71) cells were exposed to siEFBP2-containing formulations (sequence for targeting EWS-FLI1 fusion protein) made with Oligofectamine (OFA) or cyclodextrin-containing polycation (im-CDP) for 4 h. At 48 h post-transfection, cells were lysed and total cell protein was denatured, electrophoresed, and transferred to a PVDF membrane that was probed with antibodies to EWS-FLI1 or actin and quantification of Western blot analysis was performed. Average band intensities were determined by densitometry and the ratio of EWS-FLI1 to actin intensities was calculated. siEFBP2mut is a scrambled siEFBP2 siRNA that was used as a negative control.
Figure 43:
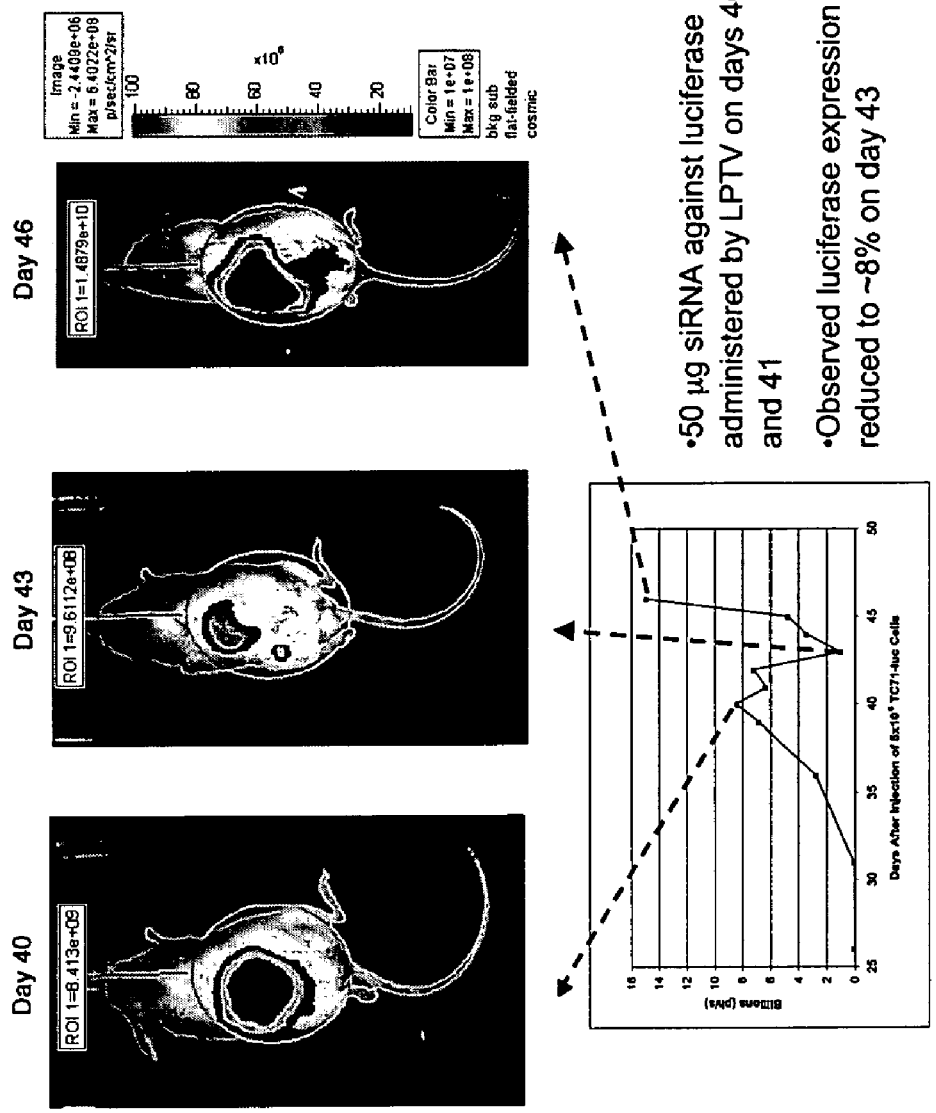
FIG. 43 shows delivery of an siRNA against luciferase by transferrin (Tf)-containing particles.
Figure 44:
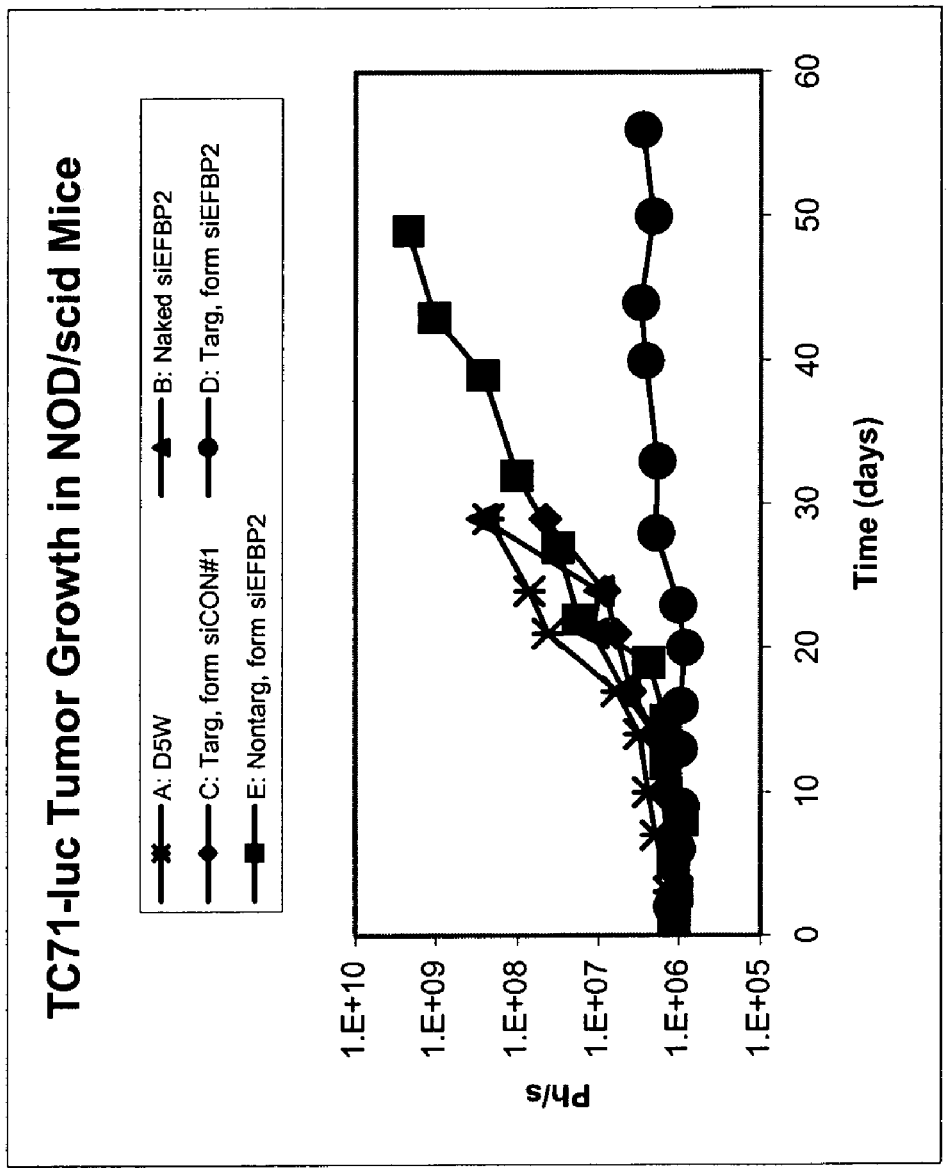
FIG. 44 shows growth curves of engrafted tumors in NOD/scid mice subjected to different treatments as indicated. The median integrated tumor bioluminescent signal (photons/sec) for each treatment group [n=8-10] is plotted versus time after injection (all at 50 μg siRNA). Groups: (A) control D5W, (B) naked siEFBP2, (C) fully formulated with a control sequence (CON#1), (D) fully formulated with siEFBP2 and (E) formulated without transferrin ligand with siEFBP2.
Figure 45:
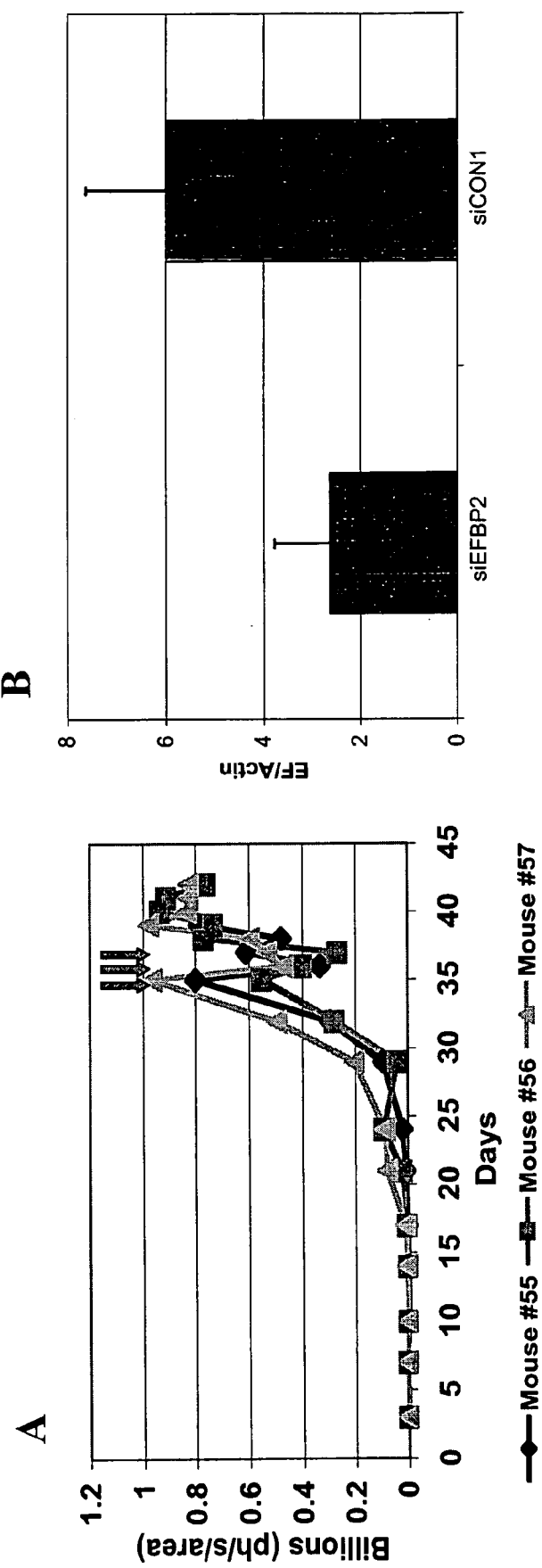
FIG. 45 shows inhibition of tumor growth by an siRNA formulated in Tf-containing particles (left panel) and sequence-specific inhibition of the target mRNA by the siRNA.

First, it was established that functional siRNA can be delivered to tumors using a normal tail vein injection. FIG. 43 shows that a very large reduction in luciferase signal can be obtained from the delivery of siRNA against luciferase using Tf-containing particles (not observed with naked siRNA). Next, we established that delivery of siRNA for EWS-FLI1 (in vitro results shown in FIG. 29) can affect tumor growth (sequence is from the Rossi laboratory; Dohjima et al., 2003) either in established tumors (FIG. 45) or during the establishment of the tumors (FIG. 44) (completely inhibits tumor growth except in the brain; the Tf-containing particles do not cross the blood-brain barrier (Pun et al., 2004)). These data clearly establish that the delivery vehicles do remain intact with targeting ligands in animals. Finally, results from blood chemistry analyses and the pathology of the major organs show that the siRNA is safely delivered without eliciting an immune response (serum IL-12 and interferon alpha not changed) or creating damage to the major organs.

As shown in FIG. 43 (top panel), bioluminescence images were obtained from the NOD/scid mice treated twice-weekly with formulated siRNA for four weeks. Starting immediately after injection of TC71-LUC cells, mice were treated with formulations containing siRNA targeting EWS-FLI1 (siEFBP2) or a non-targeting control sequence (siCON1) twice-weekly for four weeks. The bioluminescence of these mice was monitored twice-weekly.

FIG. 42 illustrates how the siRNA targeting luciferase (siGL3) was formulated and targeted. Components of the delivery system included: cyclodextrin-containing polycation (CDP), which condenses siRNA and protects it from nuclease degradation; adamantane-poly (ethylene glycol) (AD-PEG) conjugate, which stabilizes the particles in physiological fluids via inclusion compound formation; AD-PEG-transferrin (AD-PEG-Tf) conjugate, which confers a targeting ligand to particles, promoting their uptake by cells overexpressing the cell-surface transferrin receptor (TfR). Assembly of the non-targeted and targeted particles: for non-targeted particles, CDP and AD-PEG are combined and added to siRNA to generate stable but non-targeted polyplexes. For targeted particles, CDP, AD-PEG, and AD-PEG-Tf are combined and added to siRNA to generate stable, targeted particles. Prior to addition to siRNA, CDP was mixed with an AD-PEG$_{5000}$ conjugate at a 1:1 AD:β-CD (mol:mol) ratio. Targeted polyplexes also contained transferrin-modified AD-PEG (AD-PEG-Tf) at a 1:1000 AD-PEG-Tf:AD-PEG (w:w) ratio. This mixture was then added to an equal volume of siRNA at a charge ratio (positive charges from CDP to negative charges from siRNA backbone) of 3/1 (+/−). An equal volume of 10% (w/v) glucose in water was added to the resulting polyplexes to give a final polyplex formulation in 5% (w/v) glucose (D5W) suitable for injection.

The formulated siRNA was administered by low-pressure tail-vein (LPTV) injection on two consecutive days (black arrows) after injection of TC71-LUC cells. Integrated bioluminescent flux (photons/sec) is plotted versus time after cell injection. Observed luciferase expression was reduced to ~8% of the pre-treatment (day 40) values on day 43 (FIG. 43). The tumors of mice treated with the targeted, formulated siGL3-containing polyplexes showed a strong decrease (greater than 90%) in lucifrease signal 2-3 days after injection.

REFERENCES CITED

Amarzguioui, M., Holen, T., Babaie, E. and Prydz, H. (2003) Tolerance for mutations and chemical modifications in a siRNA. *Nucleic Acids Res.* 31, 589-595.

Angus, S. P., Wheeler, L. J., Ranmal, S. A., Zhang, X., Markey, M. P., Matthews, C. K. and Knudsen, E. S. (2002). The retinoblastoma tumor suppressor targets dNTP metabolism to regulate DNA replication. *J. Biol. Chem.* 277, 44376-44384.

Baenziger, J. U. and Maynard, Y. (1980) Human Hepatic Lectin—Physicochemical Properties and Specificity. *J. Biol. Chem.* 255, 4607-4613.

Bellocq, N. C., Pun, S. H., Jensen, G. S. and Davis, M. E. (2003a) Transferrrin-Containing, Cyclodextrin Polymer-Based Particles for Tumor-Targeted Gene Delivery. *Bioconjugate Chem.* 14, 1122-1132.

Bellocq, N. C., Davis, M. E., Engler, H., Jensen, G. S., Liu, A., Machemer, T., Maneval, D. C., Quijano, E., Schluep, T. and Wen, S. (2003b). Transferrin-Targeted, Cyclodextrin Polycation-Based Gene Vector for Systemic Delivery. *Mol. Therapy* 3, 750.

Bernstein, E., Denli, A. M. and Hannon, G. J. (2001) The rest is silence. *RNA* 7, 1509-1521.

Caplen, N. J., Taylor, J. P., Statham, V. S., Tanaka, F., Fire, A. and Morgan, R. A. (2002) Rescue of poyglutamine-mediated cytotoxicity by double-stranded RNA-mediated RNA interference. *Hum. Mol. Genet.* 11, 175-184.

Carmell, M. A., Xuan, Z., Zhang, M. Q. and Hannon, G. J. (2002) The Argonaute family: tentacles that reach into RNAi, developmental control, stem cell maintenance, and tumorigenesis. *Gene. Dev.* 16, 2733-2742.

Chen, S., Zhou, B., He, F. and Yen, Y. (2000) Inhibition of Human Cancer Cell Growth by Inducible Expression of Human Ribonucleotide Reductase Antisense cDNA. *Antisense Nucleic A.* 10, 111-116.

Chiu, Y.-L. and Rana, T. M. (2002) RNAi in human cells: basic structural and functional features of small interfering RNA. *Mol. Cell* 10, 549-561.

Connolly, D. T., Townsend, R. R., Kawaguchi, K., Bell, W. R. and Lee, Y. C. (1982) Binding and Endocytosis of Cluster Glycosides by Rabbit Hepatocytes—Evidence for a Short-Circuit Pathway That Does Not Lead to Degradation. *J. Biol. Chem.* 257, 939-945.

Couzin, J. (2003) RNA interference. Mini RNA molecules shield mouse liver from hepatitis. *Science* 299, 995.

Davis, M. E. and Brewster, M. E. Cyclodextrin-based pharmaceutics: past, present, future. *Nat. Rev. Drug Disc.* 3, 1023-1035 (2004).

Davis, M. E., Pun, S. H., Bellocq, N. C., Reineke, T. M., Popielarski, S. R., Mishra, S. and Heidel, J. (2004). Self-Assembling Nucleic Acid Delivery Vehicles via Linear, Water-Soluble, Cyclodextrin-Containing Polymers. *Curr. Med. Chem.* 11, 1241-1253.

Dohjima, T., Lee, N. S., Li, H., Ohno, T. and Rossi, J. J. (2003). Small Interfering RNAs Expressed from a Pol III Promoter Suppress the EWS/Fli-1 Transcript in an Ewing Sarcoma Cell Line. *Mol. Ther.* 7, 811-816.

Duxbury, M. S., Ito, H., Zinner, M. J., Ashley, S. W. and Whang, E. E. (2004a) RNA interference targeting the M2 subunit of ribonucleotide reductase enhances pancreatic adenocarcinoma chemosensitivity to gemcitabine. *Oncogene* 23, 1539-1548.

Duxbury, M. S., Ito, H., Benoit, E., Zinner, M. J., Ashley, S. W. and Whang, E. E. (2004b) Retrovirally mediated RNA interference targeting the M2 subunit of ribonucleotide reductase: A novel therapeutic strategy in pancreatic cancer. *Surgery* 136, 261-269.

Elbashir, S. M., Harborth, J., Lendeckel, W., Yalcin, A., Weber, K. and Tuschl, T. (2001a) Duplexes of 21-nucleotide RNAs mediate RNA interference in cultured mammalian cells. *Nature* 411, 494-498.

Elbashir, S. M., Martinez, J., Patkaniowska, A., Lendeckel, W. and Tuschl, T. (2001b) Functional anatomy of siRNAs for mediating efficient RNAi in *Drosophila melanogaster* embryo lysate. *EMBO J.* 20, 6877-6888.

Engstrom, Y., Eriksson, S., Jildevik, I., Skog, S., Thelander, L. and Tribukait, B. (1985) Cell cycle-dependent expression of mammalian ribonucleotide reductase. *J. Biol. Chem.* 260, 9114-9116.

Fadden, A. J., Holt, O. J. and Drickamer, K. (2003) Molecular characterization of the rat Kupffer cell glycoprotein receptor. *Glycobiology* 13, 529-537.

Fan, H., Villegas, C., Huang, A. and Wright, J. A. (1998) The mammalian ribonucleotide reductase R2 component cooperates with a variety of oncogenes in mechanisms of cellular transformation. *Cancer Res.* 58, 1650-1653.

Fang, J., Sawa, T. and Maeda, H. (2003) Factors and mechanism of "EPR" effect and the enhanced antitumor of macromolecular drugs including SMANCS. *Adv. Exp. Med. Biol.* 519, 29-49.

Garrett, S. W., Davies, O. R., Milroy, D. A., Wood, P. J., Pouton, C. W. and Threadgill, M. D. (2000). Synthesis and Characterisation of Polyamine-Poly(ethylene glycol) Constructs for DNA Binding and Gene Delivery. *Bioorg. Med. Chem.* 8, 1779-1797.

Gerolami, R., Uch, R., Brechot, C., Mannoni, P. and Bagnis, C. (2003) Gene therapy of hepatocarcinoma: a long way from the concept to the therapeutical impact. *Cancer Gene Ther.* 10, 649-660.

Gonzalez, H., Hwang, S. J. and Davis, M. E. (1999). New Class of Polymers for the Delivery of Macromolecular Therapeutics. *Bioconj. Chem.* 10, 1068-1074.

Guyton, A. C. (1981). Medical Physiology, 6th edition. W.B. Saunders Co.

Hannon, G. J. and Rossi, J. J. (2004) Unlocking the potential of the human genome with RNA interference. *Nature* 431, 371-378.

Harborth, J., Elbashir, S. M., Bechert, K., Tuschl, T. and Weber, K. (2001) Identification of essential genes in cultured mammalian cells using small interfering RNAs. *J. Cell Sci.* 114, 4557-4565.

Heale, B. S., Soifer, H. S., Bowers, C. and Rossi, J. J. (2005) siRNA target site secondary structure predictions using local stable substructures. *Nucleic Acids Res.* 33, e30.

Holen, T., Amarzguioui, M., Wiiger, M. T., Babaie, E. and Prysz, H. (2002) Positional effects of short interfering RNAs targeting the human coagulation trigger Tissue Factor. *Nucleic Acids Res.* 30, 1757-1766.

Holen, T., Amarzguioui, M., Babaie, E. and Prydz, H. (2003) Similar behaviour of single-strand and double-strand siRNAs suggests they act through a common RNAi pathway. Nucleic Acids Res. 31, 2401-2407.

Hu-Lieskovan, S., Heidel, J. D., Bartlett, D. W., Davis, M. E. and Triche, T. J. (2005) Sequence-specific knockdown of EWS-FLI1 by targeted, non-viral delivery of siRA inhibits tumor growth in a murine model of metastatic Ewing's sarcoma. *Cancer Res.*, October 1; 65(19):8984-92.

Gonzalez, H., Hwang, S. J. and Davis, M. E. (1999). New Class of Polymers for the Delivery of Macromolecular Therapeutics. *Bioconj. Chem.* 10, 1068-1074.

Jensen, R. A., Page, D. L. and Holt, J. T. (1994) Identification of genes expressed in premalignant breast disease by microscopy-directed cloning. *Proc. Natl. Acad. Sci. USA* 91, 9257-9261.

Jorgensen, K. E. and Moller, J. V. (1979) Use of flexible polymers as probes of glomerular pore-size. *Am. J. Physiol.* 236, F103-F111.

Khvorova, A., Reynolds, A. and Jayasena, S. D. (2003) Functional siRNAs and mRNAs exhibit strand bias. *Cell* 115, 209-216.

Kim, D.-H., Behlke, M. A., Rose, S. D., Chang, M. S., Choi, S. S. and Rossi, J. J. (2005) Synthetic dsRNA Dicer substrates enhance RNAi potency and efficacy. *Nat. Biotech.* 23, 222-226.

Kircheis, R., Wightman, L., Schreiber, A., Robitza, B., Rossler, V., Kursa, M., and Wagner, E. (2001). Polyethylenimine/DNA Complexes Shielded by Transferrin Target Gene Expression to Tumors After Systemic Application. *Gene Ther.* 8, 28-40.

Kitabwalla, M. and Ruprecht, R. M. (2002) RNA interference—a new weapon against HIV and beyond. *New Engl. J. Med.* 347, 1364-1367.

Kolatkar, A. R., Leung, A. K., Isecke, R., Brossmer, R., Drickamer, K. and Weis, W. I. (1998) Mechanism of N-acetylgalactosamine binding to a C-type animal lectin carbohydrate-recognition domain. *J. Biol. Chem.* 273, 19502-19508.

Kwoh, D. Y., Coffin, C. C., Lollo, C. P., Jovenal, J., Banaszczyk, M. G., Mullen, P., Phillips, A., Amini, A., Fabrycki, J., Bartholomew, R. M., Brostoff, S. W. and Carlo, D. J. (1999). Stabilization of Poly-L-Lysine/DNA Polyplexes for In Vivo Gene Delivery to the Liver. *Biochem. Biophys. Acta* 1444, 171-190.

Layzer, J. M., McCaffrey, A. P., Tanner, A. K., Huang, Z., Kay, M. A. and Sullenger, B. A. (2004) In vivo activity of nuclease-resistant siRNAs. *RNA* 10, 766-771.

Lee, R. T. and Lee, Y. C. (1997) Facile synthesis of a high-affinity ligand for mammalian hepatic lectin containing three terminal N-acetylgalactosamine residues. *Bioconjugate Chem.* 8, 762-765.

Lee, Y. C., Townsend, R. R., Hardy, M. R., Lonngren, J., Arnap, J., Haraldsson, M. and Lonn, H. (1983) Binding of Synthetic Oligosaccharides to the Hepatic Gal Galnac Lectin—Dependence on Fine-Structural Features. *J. Biol. Chem.* 258, 199-202.

Lee, Y., Vassilakos, A., Feng, N., Lam, V., Xie, H., Wang, M., Jin, H., Xiong, K., Liu, C., Wright, J. and Young, A. (2003) GTI-2040, an Antisense Agent Targeting the Small Subunit Component (R2) of Human Ribonucleotide Reductase, Shows Potent Antitumor Activity against a Variety of Tumors. *Cancer Res.* 63, 2802-2811.

Lewis, D. L., Hagstrom, J. E., Loomis, A. G., Wolff, J. A. and Herweijer, H. (2002). Efficient Delivery of siRNA for Inhibition of Gene Expression in Postnatal Mice. *Nat. Genet.* 32, 107-108.

Lin, Z. P., Belcourt, M. F., Cory, J. G. and Sartorelli, A. C. (2004) Stable Suppression of the R2 Subunit of Ribonucleotide Reductase by R2-targeted Short Interference RNA Sensitizes p53(−/−) HCT-116 Colon Cancer Cells to DNA-damaging Agents and Ribonecleotide Reductase Inhibitors. *J. Biol. Chem.* 279, 27030-27038.

Liu, F., Song, Y. and Liu, D. (1999). Hydrodynamics-based Transfection in Animals by Systemic Administration of Plasmid DNA. *Gene Ther.* 6, 1258-1266.

Liu, X., Zhou, B., Xue, L., Qiu, W., Shih, J., Zheng, S. and Yen, Y. (2004) Nuclear factor Y regulation and promoter transactivation of human ribonucleotide reductase subunit M2 gene in a Gemcitabine resistant KB clone. *Biochem. Pharm.* 67, 1499-1511.

Martinez, M. A., Clotet, B. and Este, J. A. (2002) RNA interference of HIV replication. *Trends Immunol.* 23, 559-591.

Matre, D. A., Sinkjaer, T., Knardahl, S., Andersen, J. B., Arendt-Nielsen, L. and Duncan, R. (1999) Polymer conjugates for tumour trageting and intracytoplasmic delivery. The EPR effect as a common gateway? *Pharm. Sci. Technol. Today* 2, 441-449.

McCaffrey, A. P., Meuse, L., Pham, T.-T. T., Conklin, D. S., Hannon, G. J. and Kay, M. A. (2002) RNA Interference in Adult Mice. *Nature* 418, 38-39.

Nguyen, H.-K., Lemieux, P., Vinogradov, S. V., Gebhart, C. L., Guerin, N., Paradis, G., Bronich, T. K., Alakhov, V. Y., Kabanov, A. V. (2000). Evaluation of Polyether-Polyethyleneimine Graft Copolymers as Gene Transfer Agents. *Gene Ther.* 7, 129-138.

Nykanen, A., Haley, B., and Zamore, P. D. (2001) ATP requirements and small interfering RNA structure in the RNA interference pathway. *Cell* 107, 309-321.

Orr, R. M. and Dorr, F. A. (2004) Clinical Studies of Antisense Oligonucleotides for Cancer Therapy. From *Methods in Molecular Medicine, Vol. 106: Antisense Therapeutics, Second Edition*, M. I. Phillips, ed., Humana Press.

Ozaki, K., Lee, R. T., Lee, Y. C. and Kawasaki, T. (1995) The Differences in Structural Specificity for Recognition and Binding between Asialoglycoprotein Receptors of Liver and Macrophages. *Glycoconjugate J.* 12, 268-274.

Popielarski, S. and Davis, M. E. (2005) A Nanoperticle-Based Model Delivery System to Guide the Rational Design of Gene Delivery to the Liver. In preparation.

Plank, C., Mechtler, K., Szoka, F. C. and Wagner, E. (1996). Activation of the complement system by synthetic DNA complexes: A potential barrier for intravenous gene delivery. *Hum. Gene Ther.* 7, 1437-1446.

Pun, S. H. and Davis, M. E. (2002). Development of a Non-Viral Gene Delivery Vehicle for Systemic Application. *Bioconjugate Chem.* 13, 630-639.

Pun, S. H., Bellocq, N. C., Cheng, J., Grubbs, B. H., Jensen, G. S., Davis, M. E., Tack, F., Brewster, M., Janicot, M., Janssens, B., Floren, W. and Bakker, A. (2004). Targeted Delivery of RNA-Cleaving DNA Enzyme (DNAzyme) to Tumor Tissue by Transferrin-Modified, Cyclodextrin-Based Particles. *Cancer Biol. Ther.* 3, 641-650.

Putnam, D., Gentry, C. A., Pack, D. W. and Langer, R. (2001). Polymer-Based Gene Delivery with Low Cytotoxicity by a Unique Balance of Side-Chain Termini. *Proc. Natl. Acad. Sci.* 98, 1200-1205.

Randall, G. and Rice, C. M. (2001) Hepatitis C virus cell culture replication systems: their potential use for the development of antiviral therapies. *Curr. Opin. Infect. Dis.* 14, 743-747.

Reineke, T. M. and Davis, M. E. (2003a). Structural Effects of Carbohydrate-Containing Polycations on Gene Delivery. Part 1: Carbohydrate Size and Its Distance from Charge Centers. *Bioconjugate Chem.* 14, 243-254.

Reineke, T. M. and Davis, M. E. (2003b). Structural Effects of Carbohydrate-Containing Polycations on Gene Delivery. Part 2: Charge Center Types. *Bioconjugate Chem.* 14, 255-261.

Rensen, P. C. N., Sliedregt, L. A. J. M., Ferns, M., Kieviet, E., van Rossenberg, S. M. W., van Berkel, T. J. C. and Biessen, E. A. I. (2001). Determination of the Upper Size Limit for Uptake and Processing of Ligands by the Asialoglycoprotein Receptor on Hepatocytes In Vitro and In Vivo. *J. Biol. Chem.* 276, 37577-37584.

Sagara, K. and Kim, S. W. (2002). A New Synthesis of Galactose-Poly(ethylene glycol)-Polyethylenimine for Gene Delivery to Hepatocytes. *J. Control. Rel.* 79, 271-281.

Sarkar, M., Liao, J., Kabat, E. A., Tanabe, T. and Ashwell, G. (1979) Binding-Site of Rabbit Hepatic Lectin. *J. Biol. Chem.* 254, 3170-3174.

Scherer, L. J. and Rossi, J. J. (2003a) Approaches for the sequence-specific knockdown of mRNA. *Nat. Biotech.* 21, 1457-1465.

Scherer, L. J. and Rossi, J. J. (2003b) Recent Applications of RNAi in Mammalian Systems. In: During, H., ed., *Peptide Nucleic Acids, Morpholinos, and Related Antisense Biomolecules*, Landes Bioscience.

Scherr, M., Morgan, M. A. and Eder, M. (2003) Gene Silencing Mediated by Small Interfering RNAs in Mammalian Cells. *Curr. Med. Chem.* 10, 245-256.

Schwarz, D. S., Hutvagner, G., Haley, B. and Zamore, P. D. (2002) Evidence that siRNAs function as guides, not primers in the *Drosophila* and human RNAi pathways. *Mol. Cell* 10, 537-548.

Schwarz, D. S., Hutvagner, G., Du, T., Xu, Z., Aronin, N. and Zamore, P. D. (2003) Asymmetry in the assembly of the RNAi enzyme complex. *Cell* 115, 199-208.

Siolas, D., Lerner, C., Burchard, J., Ge, W., Linsley, P. S., Paddison, P. J., Hannon, G. J. and Cleary, M. A. (2005) Synthetic shRNAs as potent RNAi triggers. *Nat. Biotech.* 23, 227-231.

Song, E., Lee, S. K., Wang, J., Ince, N., Ouyang, N., Min, J., Chen, J., Shankar, P. and Lieberman, J. (2003). RNA Interference Targeting FAS Protects Mice from Fulminant Hepatitis. *Nat. Med.* 9, 347-351.

Soutschek, J., Akinc, A., Bramlage, B., Charisse, K., Constien, R., Donoghue, M., Elbashir, S., Geick, A., Hadwiger, P., Harborth, J., John, M., Kesavan, V., Lavine, G., Pandey, R. K., Racie, T., Rajeev, K. G., Röhl, I., Toudjarska, I., Wang, G., Wuschko, S., Bumcrot, D., Kotellansky, V., Limmer, S., Manoharan, M. and Vornlocher, H.-P. (2004) Therapeutic silencing of an endogenous gene by systemic administration of modified siRNAs. *Nature* 432, 173-178.

Tanaka, T., Shiramoto, S., Miyashita, M., Fujishima, Y. and Kaneo, Y. (2004) Tumor targeting based on the effect of enhanced permeability and retention (EPR) and the mechanism of receptor-mediated endocytosis (RME). *Int. J. Pharm.* 277, 39-61.

Tomari, Y., Matranga, C., Haley, B., Martinez, N. and Zamore, P. D. (2004) A protein sensor for siRNA asymmetry. *Science* 306, 1377-1380.

Westerlind, U., Westman, J., Törnquist, Smith, C. I. E., Oscarson, S., Lahmann, M. and Norberg, T. (2004). Ligands of the asialoglycoprotein receptor for targeted gene delivery, part 1: Synthesis of and binding studies with biotinylated cluster glycosides containing N-acetylgalactosamine. *Glycoconjugate J.* 21, 227-241.

Wilson, J. A., Jayasena, S., Khvorova, A., Sabatinos, S., Rodrigue-Gervais, I. G., Arya, S., Sarangi, F., Harris-Brandts, M., Beaulieu, S. and Richardson, C. D. (2003) RNA interference blocks gene expressin and RNA synthesis from hepatitis C replicons propagated in human liver cells. *Proc. Nat. Acad. Sci. USA* 100, 2783-2788.

Yant, S. R., Meuse, L., Chiu, W., Ivics, Z., Izsvak, Z. and Kay, M. A. (2000). Somatic Integration and Long-term Transgene Expression in Normal and Hemophilic Mice Using a DNA Transposon System. *Nat. Genet.* 25, 35-41.

Yen, Y. (2003) Ribonucleotide Reductase Subunit One as Gene Therapy Target. *Clin. Cancer Res.* 9, 4304-4308.

Zamore, P. D. (2001) RNA interference: listening to the sound of silence. *Nat. Struct. Biol.* 8, 746-750.

Zhang, G. F., Budker, V. and Wolff, J. A. (1999). High Levels of Foreign Gene Expression in Hepatocytes after Tail Vein Injections of Naked Plasmid DNA. *Hum. Gene Ther.* 10, 1735-1737.

Zuber, G., Dauty, E., Nothisen, M., Belguise, P. and Behr, J. P. (2001). Towards Synthetic Viruses. *Adv. Drug Del. Rev.* 52, 245-253.

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference in their entirety.

We claim:

1. A nucleic acid consisting of:
   (i) a first strand consisting of SEQ ID NO. 63 and
   (ii) a second strand consisting of SEQ ID NO. 64,
   wherein at least 12 nucleotides of the first and second strands are complementary to each other and form a double-stranded nucleic acid under physiological conditions, and wherein the double-stranded nucleic acid can reduce the expression of a ribonucleotide reductase subunit 2 (R2) in a cell by an RNA interference mechanism.

2. The nucleic acid of claim 1, wherein the nucleic acid comprises one or more modified backbone or base moieties.

3. The nucleic acid of claim 2, wherein the modified backbone or base moieties are one or more of the following: alkylphosphonates, phosphorothioates, phosphorodithioates, alkylphosphonothioates, phophoramidates, phosphate esters, carbamates, acetamidate, carboxylmethyl esters, carbonates, and phosphate triesters.

4. The nucleic acid of claim 2, wherein the nucleic acid comprises at least one 2'-O-alkylated ribonucleotide.

5. An isolated double-stranded nucleic acid consisting of a first strand consisting of SEQ ID NO: 63 and a second strand consisting of SEQ ID NO: 64, wherein said second strand hybridizes to a region of an R2 transcript corresponding to nucleotides 616-667 of SEQ ID NO: 1 under physiological conditions and decreases the expression of R2 in a cell.

6. A pharmaceutical composition comprising the nucleic acid of claim 1 or 5, and a pharmaceutically acceptable carrier.

7. The pharmaceutical composition of claim 6, wherein the pharmaceutically acceptable carrier includes a cationic polymer.

8. The pharmaceutical composition of claim 6, wherein the pharmaceutically acceptable carrier includes a cyclodextrin polymer.

9. The pharmaceutical composition of claim 6, further comprising a ligand that targets a particular tissue or cell type.

10. The pharmaceutical composition of claim 6, wherein the pharmaceutically acceptable carrier comprises:
    a cyclodextrin-containing cationic polymer, and
    a targeting moiety comprising adamantane-PEG-ligand,
    wherein the polymer and targeting moiety form nanoparticles that encapsulates the nucleic acid.

11. A method for inhibiting the growth of a tumor in a patient having a tumor comprising administering to the patient a therapeutically effective amount of the double-stranded nucleic acid of claim 1 or 5.

12. The method of claim 11, wherein the nucleic acid is formulated with a pharmaceutically acceptable carrier.

13. The method of claim 11, wherein the nucleic acid is formulated with a ligand targeting the cancer cell.

14. The method of claim 11, further including at least one additional anti-cancer chemotherapeutic agent that inhibits cancer cells in an additive or synergistic manner with the nucleic acid.

* * * * *

SEQUENCE LISTING

<160> NUMBER OF SEQ ID NOS: 96

<210> SEQ ID NO 1
<211> LENGTH: 2500
<212> TYPE: DNA
<213> ORGANISM: Homo sapiens

<400> SEQUENCE: 1

| | | | | | |
|---|---|---|---|---|---|
| cccaggcgca | gccaatggga | agggtcggag | gcatggcaca | gccaatggga | agggccgggg | 60 |
| caccaaagcc | aatgggaagg | gccgggagcg | cgcggcgcgg | gagatttaaa | ggctgctgga | 120 |
| gtgaggggtc | gcccgtgcac | cctgtcccag | ccgtcctgtc | ctggctgctc | gctctgcttc | 180 |
| gctgcgcctc | cactatgctc | tccctccgtg | tcccgctcgc | gcccatcacg | gacccgcagc | 240 |
| agctgcagct | ctcgccgctg | aaggggctca | gcttggtcga | caaggagaac | acgccgccgg | 300 |
| ccctgagcgg | gacccgcgtc | ctggccagca | agaccgcgag | gaggatcttc | caggagccca | 360 |
| cggagccgaa | aactaaagca | gctgcccccg | gcgtggagga | tgagccgctg | ctgagagaaa | 420 |
| accccccgccg | ctttgtcatc | ttccccatcg | agtaccatga | tatctggcag | atgtataaga | 480 |
| aggcagaggc | ttccttttgg | accgccgagg | aggttgacct | ctccaaggac | attcagcact | 540 |
| gggaatccct | gaaacccgag | gagagatatt | ttatatccca | tgttctggct | ttctttgcag | 600 |
| caagcgatgg | catagtaaat | gaaaacttgg | tggagcgatt | tagccaagaa | gttcagatta | 660 |
| cagaagcccg | ctgtttctat | ggcttccaaa | ttgccatgga | aaacatacat | tctgaaatgt | 720 |
| atagtcttct | tattgacact | tacataaaag | atcccaaaga | aagggaattt | ctcttcaatg | 780 |
| ccattgaaac | gatgccttgt | gtcaagaaga | aggcagactg | ggccttgcgc | tggattgggg | 840 |
| acaaagaggc | tacctatggt | gaacgtgttg | tagcctttgc | tgcagtggaa | ggcatttttct | 900 |
| tttccggttc | ttttgcgtcg | atattctggc | tcaagaaacg | aggactgatg | cctggcctca | 960 |
| catttctaa | tgaacttatt | agcagagatg | agggtttaca | ctgtgatttt | gcttgcctga | 1020 |
| tgttcaaaca | cctggtacac | aaaccatcgg | aggagagagt | aagagaaata | attatcaatg | 1080 |
| ctgttcggat | agaacaggag | ttcctcactg | aggccttgcc | tgtgaagctc | attgggatga | 1140 |
| attgcactct | aatgaagcaa | tacattgagt | tgtggcaga | cagacttatg | ctggaactgg | 1200 |
| gttttagcaa | ggttttcaga | gtagagaacc | catttgactt | tatggagaat | atttcactgg | 1260 |
| aaggaaagac | taacttcttt | gagaagagag | taggcgagta | tcagaggatg | ggagtgatgt | 1320 |
| caagtccaac | agagaattct | tttaccttgg | atgctgactt | ctaaatgaac | tgaagatgtg | 1380 |
| cccttacttg | gctgattttt | tttttccatc | tcataagaaa | aatcagctga | agtgttacca | 1440 |
| actagccaca | ccatgaattg | tccgtaatgt | tcattaacag | catctttaaa | actgtgtagc | 1500 |
| tacctcacaa | ccagtcctgt | ctgtttatag | tgctggtagt | atcacctttt | gccagaaggc | 1560 |
| ctggctggct | gtgacttacc | atagcagtga | caatggcagt | cttggcttta | aagtgagggg | 1620 |
| tgacccttta | gtgagcttag | cacagcggga | ttaaacagtc | ctttaaccag | cacagccagt | 1680 |
| taaaagatgc | agcctcactg | cttcaacgca | gattttaatg | tttacttaaa | tataaacctg | 1740 |
| gcactttaca | aacaaataaa | cattgttttg | tactcacggc | ggcgataata | gcttgattta | 1800 |
| tttggtttct | acaccaaata | cattctcctg | accactaatg | ggagccaatt | cacaattcac | 1860 |
| taagtgacta | aagtaagtta | aacttgtgta | gactaagcat | gtaattttta | agttttattt | 1920 |
| taatgaatta | aatatttgt | taaccaactt | taaagtcagt | cctgtgtata | cctagatatt | 1980 |
| agtcagttgg | tgccagatag | aagacaggtt | gtgttttat | cctgtggctt | gtgtagtgtc | 2040 |

```
ctgggattct ctgcccctc tgagtagagt gttgtgggat aaaggaatct ctcagggcaa    2100
ggagcttctt aagttaaatc actagaaatt tagggggtgat ctgggccttc atatgtgtga   2160
gaagccgttt catttttattt ctcactgtat tttcctcaac gtctggttga tgagaaaaaa   2220
ttcttgaaga gttttcatat gtgggagcta aggtagtatt gtaaaatttc aagtcatcct   2280
taaacaaaat gatccaccta agatcttgcc cctgttaagt ggtgaaatca actagaggtg   2340
gttcctacaa gttgttcatt ctagtttgt ttggtgtaag taggttgtgt gagttaattc    2400
atttatattt actatgtctg ttaaatcaga aattttttat tatctatgtt cttctagatt   2460
ttacctgtag ttcataaaaa aaaaaaaaa aaaaaaaaa                           2500

<210> SEQ ID NO 2
<211> LENGTH: 969
<212> TYPE: DNA
<213> ORGANISM: Homo sapiens

<400> SEQUENCE: 2
ttagaagtcc cagtcggtgt cggtggtggg ttggtgggtg cccattacgt atgagcttcc     60
ggagccggag aaaaagtcgt ggttctcccc tgcaccgggg tcgagagctg cgcgcacggc    120
cgggttcacc tggcaggtgt cacgatcgaa tgcaggctgg tatcccaggt tggctagcgc    180
cttgttggcg ttgtaacgca tgtagggcaa aacgtcgtcg gtccagccca actcgtcgta    240
caagtcgtgc gcatagtcga tctcgttcgc gtagagcgtg tgcagcagct cgcaggtgta    300
ttcgcggtgg tcggcccgct cggcgtcggt caggtcggcc aaacctcgtt gacatttgta    360
gccgatgtag tagccgtgga cggcttcatc tcggatgatc agccggatca gatcggcggt    420
gttggtgagc ttaccccgcg acgaccagta catgggcagg tagaagccgg agtagaacag    480
gaaggactcc agcattaccg acgatgcttt gcgcttgagc gcgtcgtcac cgcggtagta    540
gtcgacgatg atctgcgctt ttcgctgcag gtaagggttc tgttccgacc agtcgaaggc    600
atcgtcgatc tgcttggtcg agcacagggt cgagaagatc gagctgtagc tcttggcgtg    660
cactgactcc atgaacgcca tgttggtcag gaccgcctct tcgtgggggg tgaccgcgtc    720
gtcgatcatg gccactgctc ccaccgtcgc ctgcgcggtg tcgagcaggg tcaagccggt    780
gaacacccgg atcgtcgtct gctgctcggt ggaactcaac gtttgccaag atgccaggtc    840
gttggagagc ggaatctttt ccggcaacca aaagttaccg gtcaaacgtt cccagacctg    900
caaatcttta gcatcgagca accggttcca attgattgcg tgcacccgct caacgagctt    960
gccggtcat                                                            969

<210> SEQ ID NO 3
<211> LENGTH: 909
<212> TYPE: DNA
<213> ORGANISM: Human Herpes Virus4

<400> SEQUENCE: 3
atgtccaagt tgttgtacgt gcgtgatcat gagggctttg cctgcctaac ggtcgaaacc     60
caccgcaacc gctggttcgc ggctcacatt gtcctcacca aggactgcgg gtgtctcaag    120
ctactcaatg agagggactt ggagttttac aagttcctct ttacgttcct ggccatggcc    180
gagaagcttg tgaactttaa cattgatgaa ctggtcacca gcttcgagag ccacgacatt    240
gatcactact acaccgagca gaaggccatg gagaacgtcc acggggagac ttatgctaac    300 attttaaaaca tgctctttga tggggacagg gcggcgatga acgcctacgc agaggccatc    360
```

-continued

```
atggccgacg aggccctgca agccaagatt tcctggctcc gtgacaaggt ggcggccgcc      420
gtcaccctgc cggagaagat tcttgtgttc ctgctgattg aaggcatctt cttcattagc      480
tccttctaca gcatagccct gctgcgggtc cggggcctaa tgcctggcat ctgcctggcc      540
aataactaca taagtaggga tgagctgctc cacacccgcg ctgcctccct gttatacaat      600
agcatgacag ccaaggctga ccgaccaagg gccacctgga tccaggagct gtttcgcact      660
gcggtggagg tagagactgc cttcatcgag gctcgtggag aggggttac cttggtggat       720 gtgcgagcca taaagcagtt tctggaggcc acggccgatc gcatcctggg tgacattggt      780
caggctccct tgtatggcac caccccccc aaggactgcc cgctcaccta catgactagc       840
atcaagcaaa ctaatttctt tgagcaagag agttccgatt acaccatgct ggtggtagat      900
gacctttga                                                              909
```

<210> SEQ ID NO 4
<211> LENGTH: 11
<212> TYPE: DNA
<213> ORGANISM: Homo sapiens

<400> SEQUENCE: 4
cgaguaccau g                                                            11

<210> SEQ ID NO 5
<211> LENGTH: 11
<212> TYPE: DNA
<213> ORGANISM: Homo sapiens

<400> SEQUENCE: 5
gauuuagcca a                                                            11

<210> SEQ ID NO 6
<211> LENGTH: 11
<212> TYPE: DNA
<213> ORGANISM: Homo sapiens

<400> SEQUENCE: 6
aagaaacgag g                                                            11

<210> SEQ ID NO 7
<211> LENGTH: 21
<212> TYPE: RNA
<213> ORGANISM: Artificial Sequence
<220> FEATURE:
<223> OTHER INFORMATION: siRNA

<400> SEQUENCE: 7
cccaucgagu accaugauau c                                                 21

<210> SEQ ID NO 8
<211> LENGTH: 21
<212> TYPE: RNA
<213> ORGANISM: Artificial Sequence
<220> FEATURE:
<223> OTHER INFORMATION: siRNA

<400> SEQUENCE: 8
uaucauggua cucgaugggg a                                                 21

<210> SEQ ID NO 9
<211> LENGTH: 21
<212> TYPE: RNA
<213> ORGANISM: Artificial Sequence

```
<220> FEATURE:
<223> OTHER INFORMATION: siRNA

<400> SEQUENCE: 9
ggagcgauuu agccaagaag u                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
uucuuggcua aaucgcucca c                                              21

<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
ggcucaagaa acgaggacug a                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA

<400> SEQUENCE: 12
aguccucguu ucuugagcca g                                              21

<210> SEQ ID NO 13
<211> LENGTH: 25
<212> TYPE: RNA
<213> ORGANISM: Artificial Sequence
<220> FEATURE:
<223> OTHER INFORMATION: siRNA

<400> SEQUENCE: 13
cccaucgagu accaugauau cuggc                                          25

<210> SEQ ID NO 14
<211> LENGTH: 27
<212> TYPE: RNA
<213> ORGANISM: Artificial Sequence
<220> FEATURE:
<223> OTHER INFORMATION: siRNA

<400> SEQUENCE: 14
gccagauauc augguacucg auggga                                         27

<210> SEQ ID NO 15
<211> LENGTH: 27
<212> TYPE: RNA
<213> ORGANISM: Artificial Sequence
<220> FEATURE:
<223> OTHER INFORMATION: siRNA

<400> SEQUENCE: 15
aucuucccca ucgaguacca ugauauc                                        27
```

```
<210> SEQ ID NO 16
<211> LENGTH: 25
<212> TYPE: DNA
<213> ORGANISM: Artificial Sequence
<220> FEATURE:
<223> OTHER INFORMATION: siRNA

<400> SEQUENCE: 16
uaucauggua cucgaugggg aagat                                          25

<210> SEQ ID NO 17
<211> LENGTH: 25
<212> TYPE: RNA
<213> ORGANISM: Artificial Sequence
<220> FEATURE:
<223> OTHER INFORMATION: siRNA

<400> SEQUENCE: 17
ggagcgauuu agccaagaag uucag                                          25

<210> SEQ ID NO 18
<211> LENGTH: 27
<212> TYPE: RNA
<213> ORGANISM: Artificial Sequence
<220> FEATURE:
<223> OTHER INFORMATION: siRNA

<400> SEQUENCE: 18
cugaacuucu uggcuaaauc gcuccac                                        27

<210> SEQ ID NO 19
<211> LENGTH: 27
<212> TYPE: RNA
<213> ORGANISM: Artificial Sequence
<220> FEATURE:
<223> OTHER INFORMATION: siRNA

<400> SEQUENCE: 19
cuugguggag cgauuuagcc aagaagu                                        27

<210> SEQ ID NO 20
<211> LENGTH: 25
<212> TYPE: RNA
<213> ORGANISM: Artificial Sequence
<220> FEATURE:
<223> OTHER INFORMATION: siRNA

<400> SEQUENCE: 20
uucuuggcua aaucgcucca ccaag                                          25

<210> SEQ ID NO 21
<211> LENGTH: 25
<212> TYPE: DNA
<213> ORGANISM: Artificial Sequence
<220> FEATURE:
<223> OTHER INFORMATION: siRNA

<400> SEQUENCE: 21
ggcucaagaa acgaggacug agatg                                          25

<210> SEQ ID NO 22
<211> LENGTH: 27
<212> TYPE: RNA
<213> ORGANISM: Artificial Sequence
<220> FEATURE:
<223> OTHER INFORMATION: siRNA
```

```
<400> SEQUENCE: 22
caucucaguc cucguuucuu gagccag                                        27

<210> SEQ ID NO 23
<211> LENGTH: 27
<212> TYPE: RNA
<213> ORGANISM: Artificial Sequence
<220> FEATURE:
<223> OTHER INFORMATION: siRNA

<400> SEQUENCE: 23
uauucuggcu caagaaacga ggacuga                                        27

<210> SEQ ID NO 24
<211> LENGTH: 25
<212> TYPE: DNA
<213> ORGANISM: Artificial Sequence
<220> FEATURE:
<223> OTHER INFORMATION: siRNA

<400> SEQUENCE: 24
aguccucguu ucuugagcca gaata                                          25

<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
ucuuccccau cgaguaccau g                                              21

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
ugguacucga ugggaagau g                                               21

<210> SEQ ID NO 27
<211> LENGTH: 21
<212> TYPE: RNA
<213> ORGANISM: Artificial Sequence
<220> FEATURE:
<223> OTHER INFORMATION: siRNA

<400> SEQUENCE: 27
cuuccccauc gaguaccaug a                                              21

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
augguacucg augggaaga u                                               21

<210> SEQ ID NO 29
```

```
<211> LENGTH: 21
<212> TYPE: RNA
<213> ORGANISM: Artificial Sequence
<220> FEATURE:
<223> OTHER INFORMATION: siRNA

<400> SEQUENCE: 29
uuccccaucg aguaccauga u                                              21

<210> SEQ ID NO 30
<211> LENGTH: 21
<212> TYPE: RNA
<213> ORGANISM: Artificial Sequence
<220> FEATURE:
<223> OTHER INFORMATION: siRNA

<400> SEQUENCE: 30
caugguacuc gaugggaag a                                               21

<210> SEQ ID NO 31
<211> LENGTH: 21
<212> TYPE: RNA
<213> ORGANISM: Artificial Sequence
<220> FEATURE:
<223> OTHER INFORMATION: siRNA

<400> SEQUENCE: 31
uccccaucga guaccaugau a                                              21

<210> SEQ ID NO 32
<211> LENGTH: 21
<212> TYPE: RNA
<213> ORGANISM: Artificial Sequence
<220> FEATURE:
<223> OTHER INFORMATION: siRNA

<400> SEQUENCE: 32 ucauggacu cgaugggaa g                                                21

<210> SEQ ID NO 33
<211> LENGTH: 21
<212> TYPE: RNA
<213> ORGANISM: Artificial Sequence
<220> FEATURE:
<223> OTHER INFORMATION: siRNA

<400> SEQUENCE: 33
ccccaucgag uaccaugaua u                                              21

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
aucaugguac ucgauggga a                                               21

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
```

-continued ccaucgagua ccaugauauc u                    21

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
auaucauggu acucgauggg g                    21

<210> SEQ ID NO 37
<211> LENGTH: 21
<212> TYPE: RNA
<213> ORGANISM: Artificial Sequence
<220> FEATURE:
<223> OTHER INFORMATION: siRNA

<400> SEQUENCE: 37
caucgaguac caugauaucu g                    21

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
gauaucaugg uacucgaugg g                    21

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
aucgaguacc augauaucug g                    21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
agauaucaug guacucgaug g                    21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
ucgaguacca ugauaucugg c                    21

<210> SEQ ID NO 42
<211> LENGTH: 21
<212> TYPE: RNA

-continued

```
<213> ORGANISM: Artificial Sequence
<220> FEATURE:
<223> OTHER INFORMATION: siRNA

<400> SEQUENCE: 42
cagauaucau gguacucgau g                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
cgaguaccau gauaucuggc a                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA

<400> SEQUENCE: 44
ccagauauca ugguacucga u                                              21

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uugguggagc gauuuagcca a                                              21

<210> SEQ ID NO 46
<211> LENGTH: 21
<212> TYPE: RNA
<213> ORGANISM: Artificial Sequence
<220> FEATURE:
<223> OTHER INFORMATION: siRNA

<400> SEQUENCE: 46
ggcuaaaucg cuccaccaag u                                              21

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
ugguggagcg auuuagccaa g                                              21

<210> SEQ ID NO 48
<211> LENGTH: 21
<212> TYPE: RNA
<213> ORGANISM: Artificial Sequence
<220> FEATURE:
<223> OTHER INFORMATION: siRNA

<400> SEQUENCE: 48
uggcuaaauc gcuccaccaa g                                              21
```

<210> SEQ ID NO 49
<211> LENGTH: 21
<212> TYPE: RNA
<213> ORGANISM: Artificial Sequence
<220> FEATURE:
<223> OTHER INFORMATION: siRNA

<400> SEQUENCE: 49
gguggagcga uuuagccaag a							21

<210> SEQ ID NO 50
<211> LENGTH: 21
<212> TYPE: RNA
<213> ORGANISM: Artificial Sequence
<220> FEATURE:
<223> OTHER INFORMATION: siRNA

<400> SEQUENCE: 50
uuggcuaaau cgcuccacca a							21

<210> SEQ ID NO 51
<211> LENGTH: 21
<212> TYPE: RNA
<213> ORGANISM: Artificial Sequence
<220> FEATURE:
<223> OTHER INFORMATION: siRNA

<400> SEQUENCE: 51
guggagcgau uuagccaaga a							21

<210> SEQ ID NO 52
<211> LENGTH: 21
<212> TYPE: RNA
<213> ORGANISM: Artificial Sequence
<220> FEATURE:
<223> OTHER INFORMATION: siRNA

<400> SEQUENCE: 52
cuuggcuaaa ucgcuccacc a							21

<210> SEQ ID NO 53
<211> LENGTH: 21
<212> TYPE: RNA
<213> ORGANISM: Artificial Sequence
<220> FEATURE:
<223> OTHER INFORMATION: siRNA

<400> SEQUENCE: 53
uggagcgauu uagccaagaa g							21

<210> SEQ ID NO 54
<211> LENGTH: 21
<212> TYPE: RNA
<213> ORGANISM: Artificial Sequence
<220> FEATURE:
<223> OTHER INFORMATION: siRNA

<400> SEQUENCE: 54
ucuuggcuaa aucgcuccac c							21

<210> SEQ ID NO 55
<211> LENGTH: 21
<212> TYPE: RNA
<213> ORGANISM: Artificial Sequence
<220> FEATURE:

-continued

```
<223> OTHER INFORMATION: siRNA

<400> SEQUENCE: 55
gagcgauuua gccaagaagu u                                              21

<210> SEQ ID NO 56
<211> LENGTH: 21
<212> TYPE: RNA
<213> ORGANISM: Artificial Sequence
<220> FEATURE:
<223> OTHER INFORMATION: siRNA

<400> SEQUENCE: 56
cuucuuggcu aaaucgcucc a                                              21

<210> SEQ ID NO 57
<211> LENGTH: 21
<212> TYPE: RNA
<213> ORGANISM: Artificial Sequence
<220> FEATURE:
<223> OTHER INFORMATION: siRNA

<400> SEQUENCE: 57
agcgauuuag ccaagaaguu c                                              21

<210> SEQ ID NO 58
<211> LENGTH: 21
<212> TYPE: RNA
<213> ORGANISM: Artificial Sequence
<220> FEATURE:
<223> OTHER INFORMATION: siRNA

<400> SEQUENCE: 58
acuucuuggc uaaaucgcuc c                                              21

<210> SEQ ID NO 59
<211> LENGTH: 21
<212> TYPE: RNA
<213> ORGANISM: Artificial Sequence
<220> FEATURE:
<223> OTHER INFORMATION: siRNA

<400> SEQUENCE: 59
gcgauuuagc caagaaguuc a                                              21

<210> SEQ ID NO 60
<211> LENGTH: 21
<212> TYPE: RNA
<213> ORGANISM: Artificial Sequence
<220> FEATURE:
<223> OTHER INFORMATION: siRNA

<400> SEQUENCE: 60
aacuucuugg cuaaaucgcu c                                              21

<210> SEQ ID NO 61
<211> LENGTH: 21
<212> TYPE: RNA
<213> ORGANISM: Artificial Sequence
<220> FEATURE:
<223> OTHER INFORMATION: siRNA

<400> SEQUENCE: 61
cgauuuagcc aagaaguuca g                                              21
```

```
<210> SEQ ID NO 62
<211> LENGTH: 21
<212> TYPE: RNA
<213> ORGANISM: Artificial Sequence
<220> FEATURE:
<223> OTHER INFORMATION: siRNA

<400> SEQUENCE: 62
gaacuucuug gcuaaaucgc u                                             21

<210> SEQ ID NO 63
<211> LENGTH: 21
<212> TYPE: RNA
<213> ORGANISM: Artificial Sequence
<220> FEATURE:
<223> OTHER INFORMATION: siRNA

<400> SEQUENCE: 63
gauuuagcca agaaguucag a                                             21

<210> SEQ ID NO 64
<211> LENGTH: 21
<212> TYPE: RNA
<213> ORGANISM: Artificial Sequence
<220> FEATURE:
<223> OTHER INFORMATION: siRNA

<400> SEQUENCE: 64
ugaacuucuu ggcuaaaucg c                                             21

<210> SEQ ID NO 65
<211> LENGTH: 21
<212> TYPE: RNA
<213> ORGANISM: Artificial Sequence
<220> FEATURE:
<223> OTHER INFORMATION: siRNA

<400> SEQUENCE: 65
auucuggcuc aagaaacgag g                                             21

<210> SEQ ID NO 66
<211> LENGTH: 21
<212> TYPE: RNA
<213> ORGANISM: Artificial Sequence
<220> FEATURE:
<223> OTHER INFORMATION: siRNA

<400> SEQUENCE: 66
ucguuucuug agccagaaua u                                             21

<210> SEQ ID NO 67
<211> LENGTH: 21
<212> TYPE: RNA
<213> ORGANISM: Artificial Sequence
<220> FEATURE:
<223> OTHER INFORMATION: siRNA

<400> SEQUENCE: 67
uucuggcuca agaaacgagg a                                             21

<210> SEQ ID NO 68
<211> LENGTH: 21
<212> TYPE: RNA
<213> ORGANISM: Artificial Sequence
<220> FEATURE:
<223> OTHER INFORMATION: siRNA
```

```
<400> SEQUENCE: 68
cucguuucuu gagccagaau a                                              21

<210> SEQ ID NO 69
<211> LENGTH: 21
<212> TYPE: RNA
<213> ORGANISM: Artificial Sequence
<220> FEATURE:
<223> OTHER INFORMATION: siRNA

<400> SEQUENCE: 69
ucuggcucaa gaaacgagga c                                              21

<210> SEQ ID NO 70
<211> LENGTH: 21
<212> TYPE: RNA
<213> ORGANISM: Artificial Sequence
<220> FEATURE:
<223> OTHER INFORMATION: siRNA

<400> SEQUENCE: 70
ccucguuucu ugagccagaa u                                              21

<210> SEQ ID NO 71
<211> LENGTH: 21
<212> TYPE: RNA
<213> ORGANISM: Artificial Sequence
<220> FEATURE:
<223> OTHER INFORMATION: siRNA

<400> SEQUENCE: 71
cuggcucaag aaacgaggac u                                              21

<210> SEQ ID NO 72
<211> LENGTH: 21
<212> TYPE: RNA
<213> ORGANISM: Artificial Sequence
<220> FEATURE:
<223> OTHER INFORMATION: siRNA

<400> SEQUENCE: 72
uccucguuuc uugagccaga a                                              21

<210> SEQ ID NO 73
<211> LENGTH: 21
<212> TYPE: RNA
<213> ORGANISM: Artificial Sequence
<220> FEATURE:
<223> OTHER INFORMATION: siRNA

<400> SEQUENCE: 73
uggcucaaga aacgaggacu g                                              21

<210> SEQ ID NO 74
<211> LENGTH: 21
<212> TYPE: RNA
<213> ORGANISM: Artificial Sequence
<220> FEATURE:
<223> OTHER INFORMATION: siRNA

<400> SEQUENCE: 74
guccucguuu cuugagccag a                                              21

<210> SEQ ID NO 75
<211> LENGTH: 21
```

```
<212> TYPE: RNA
<213> ORGANISM: Artificial Sequence
<220> FEATURE:
<223> OTHER INFORMATION: siRNA

<400> SEQUENCE: 75
gcucaagaaa cgaggacuga u                                              21

<210> SEQ ID NO 76
<211> LENGTH: 21
<212> TYPE: RNA
<213> ORGANISM: Artificial Sequence
<220> FEATURE:
<223> OTHER INFORMATION: siRNA

<400> SEQUENCE: 76
caguccucgu uucuugagcc a                                              21

<210> SEQ ID NO 77
<211> LENGTH: 21
<212> TYPE: RNA
<213> ORGANISM: Artificial Sequence
<220> FEATURE:
<223> OTHER INFORMATION: siRNA

<400> SEQUENCE: 77
cucaagaaac gaggacugau g                                              21

<210> SEQ ID NO 78
<211> LENGTH: 21
<212> TYPE: RNA
<213> ORGANISM: Artificial Sequence
<220> FEATURE:
<223> OTHER INFORMATION: siRNA

<400> SEQUENCE: 78
ucaguccucg uuucuugagc c                                              21

<210> SEQ ID NO 79
<211> LENGTH: 21
<212> TYPE: RNA
<213> ORGANISM: Artificial Sequence
<220> FEATURE:
<223> OTHER INFORMATION: siRNA

<400> SEQUENCE: 79
ucaagaaacg aggacugaug c                                              21

<210> SEQ ID NO 80
<211> LENGTH: 21
<212> TYPE: RNA
<213> ORGANISM: Artificial Sequence
<220> FEATURE:
<223> OTHER INFORMATION: siRNA

<400> SEQUENCE: 80
aucaguccuc guuucuugag c                                              21

<210> SEQ ID NO 81
<211> LENGTH: 21
<212> TYPE: RNA
<213> ORGANISM: Artificial Sequence
<220> FEATURE:
<223> OTHER INFORMATION: siRNA

<400> SEQUENCE: 81
```
caagaaacga ggacugaugc c 21

<210> SEQ ID NO 82
<211> LENGTH: 21
<212> TYPE: RNA
<213> ORGANISM: Artificial Sequence
<220> FEATURE:
<223> OTHER INFORMATION: siRNA

<400> SEQUENCE: 82
caucaguccu cguuucuuga g 21

<210> SEQ ID NO 83
<211> LENGTH: 21
<212> TYPE: RNA
<213> ORGANISM: Artificial Sequence
<220> FEATURE:
<223> OTHER INFORMATION: siRNA

<400> SEQUENCE: 83
aagaaacgag gacugaugcc u 21

<210> SEQ ID NO 84
<211> LENGTH: 21
<212> TYPE: RNA
<213> ORGANISM: Artificial Sequence
<220> FEATURE:
<223> OTHER INFORMATION: siRNA

<400> SEQUENCE: 84
gcaucagucc ucguuucuug a 21

<210> SEQ ID NO 85
<211> LENGTH: 25
<212> TYPE: RNA
<213> ORGANISM: Artificial Sequence
<220> FEATURE:
<223> OTHER INFORMATION: siRNA

<400> SEQUENCE: 85
gauuuagcca agaaguucag auuac 25

<210> SEQ ID NO 86
<211> LENGTH: 27
<212> TYPE: RNA
<213> ORGANISM: Artificial Sequence
<220> FEATURE:
<223> OTHER INFORMATION: siRNA

<400> SEQUENCE: 86
guaaucugaa cuucuuggcu aaaucgc 27

<210> SEQ ID NO 87
<211> LENGTH: 21
<212> TYPE: RNA
<213> ORGANISM: Artificial Sequence
<220> FEATURE:
<223> OTHER INFORMATION: siRNA

<400> SEQUENCE: 87
auuuagccaa gaaguucaga u 21

<210> SEQ ID NO 88
<211> LENGTH: 21
<212> TYPE: RNA
<213> ORGANISM: Artificial Sequence

```
<220> FEATURE:
<223> OTHER INFORMATION: siRNA

<400> SEQUENCE: 88
cugaacuucu uggcuaaauc g                                              21

<210> SEQ ID NO 89
<211> LENGTH: 21
<212> TYPE: RNA
<213> ORGANISM: Artificial Sequence
<220> FEATURE:
<223> OTHER INFORMATION: siRNA

<400> SEQUENCE: 89
uuuagccaag aaguucagau u                                              21

<210> SEQ ID NO 90
<211> LENGTH: 21
<212> TYPE: RNA
<213> ORGANISM: Artificial Sequence
<220> FEATURE:
<223> OTHER INFORMATION: siRNA

<400> SEQUENCE: 90
ucugaacuuc uuggcuaaau c                                              21

<210> SEQ ID NO 91
<211> LENGTH: 21
<212> TYPE: RNA
<213> ORGANISM: Artificial Sequence
<220> FEATURE:
<223> OTHER INFORMATION: siRNA

<400> SEQUENCE: 91
uuagccaaga aguucagauu a                                              21

<210> SEQ ID NO 92
<211> LENGTH: 21
<212> TYPE: RNA
<213> ORGANISM: Artificial Sequence
<220> FEATURE:
<223> OTHER INFORMATION: siRNA

<400> SEQUENCE: 92
aucugaacuu cuuggcuaaa u                                              21

<210> SEQ ID NO 93
<211> LENGTH: 21
<212> TYPE: RNA
<213> ORGANISM: Artificial Sequence
<220> FEATURE:
<223> OTHER INFORMATION: siRNA

<400> SEQUENCE: 93
uagccaagaa guucagauua c                                              21

<210> SEQ ID NO 94
<211> LENGTH: 21
<212> TYPE: RNA
<213> ORGANISM: Artificial Sequence
<220> FEATURE:
<223> OTHER INFORMATION: siRNA

<400> SEQUENCE: 94
aaucugaacu ucuuggcuaa a                                              21
```

```
<210> SEQ ID NO 95
<211> LENGTH: 21
<212> TYPE: RNA
<213> ORGANISM: Artificial Sequence
<220> FEATURE:
<223> OTHER INFORMATION: siRNA

<400> SEQUENCE: 95
agccaagaag uucagauuac a                                              21

<210> SEQ ID NO 96
<211> LENGTH: 21
<212> TYPE: RNA
<213> ORGANISM: Artificial Sequence
<220> FEATURE:
<223> OTHER INFORMATION: siRNA

<400> SEQUENCE: 96
uaaucugaac uucuuggcua a                                              21
```